United States Patent
Greenstein et al.

(10) Patent No.: US 11,389,432 B2
(45) Date of Patent: **\*Jul. 19, 2022**

(54) METHODS OF TREATING CANCER COMPRISING ADMINISTRATION OF A GLUCOCORTICOID RECEPTOR MODULATOR AND A CANCER CHEMOTHERAPY AGENT

(71) Applicant: Corcept Therapeutics Incorporated, Menlo Park, CA (US)

(72) Inventors: Andrew Greenstein, Menlo Park, CA (US); Stacie Shepherd, Menlo Park, CA (US); Andreas G. Moraitis, Menlo Park, CA (US)

(73) Assignee: Corcept Therapeutics Incorporated, Menlo Park, CA (US)

( \* ) Notice: Subject to any disclaimer, the term of this patent is extended or adjusted under 35 U.S.C. 154(b) by 309 days.

This patent is subject to a terminal disclaimer.

(21) Appl. No.: 16/719,701

(22) Filed: Dec. 18, 2019

(65) Prior Publication Data

US 2020/0197373 A1    Jun. 25, 2020

Related U.S. Application Data

(60) Provisional application No. 62/854,768, filed on May 30, 2019, provisional application No. 62/847,772, filed on May 14, 2019, provisional application No. 62/782,120, filed on Dec. 19, 2018.

(51) Int. Cl.

| | | |
|---|---|---|
| *A61K 31/437* | (2006.01) | |
| *A61K 31/337* | (2006.01) | |
| *A61K 31/573* | (2006.01) | |
| *C12Q 1/6886* | (2018.01) | |
| *A61P 35/00* | (2006.01) | |

(52) U.S. Cl.
CPC .......... *A61K 31/437* (2013.01); *A61K 31/337* (2013.01); *A61K 31/573* (2013.01); *A61P 35/00* (2018.01); *C12Q 1/6886* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,963,558 | A | 10/1990 | Hotten et al. |
| 5,696,127 | A | 12/1997 | Jones et al. |
| 6,583,180 | B2 | 6/2003 | Link et al. |
| 6,680,310 | B2 | 1/2004 | Belanoff et al. |
| 7,576,076 | B2 | 8/2009 | Clark et al. |
| 7,678,813 | B2 | 3/2010 | Clark et al. |
| 7,790,745 | B2 | 9/2010 | Yang et al. |
| 7,799,782 | B2 | 9/2010 | Munson et al. |
| 7,928,237 | B2 | 4/2011 | Clark et al. |
| 8,003,689 | B2 | 8/2011 | Veverka |
| 8,173,674 | B2 | 5/2012 | Keil et al. |
| 8,324,203 | B2 | 12/2012 | Clark et al. |
| 8,461,172 | B2 | 6/2013 | Clark et al. |
| 8,557,839 | B2 | 10/2013 | Clark et al. |
| 8,598,154 | B2 | 12/2013 | Clark et al. |
| 8,658,128 | B2 | 2/2014 | Altschul et al. |
| 8,685,973 | B2 | 4/2014 | Clark et al. |
| 8,710,035 | B2 | 4/2014 | Pan et al. |
| 8,859,774 | B2 | 10/2014 | Hunt et al. |
| 8,889,867 | B2 | 11/2014 | Clark et al. |
| 8,969,557 | B2 | 3/2015 | Harriman et al. |
| 9,114,147 | B2 | 8/2015 | Altschul et al. |
| 9,149,485 | B2 | 10/2015 | Pan et al. |
| 9,273,047 | B2 | 3/2016 | Hunt et al. |
| 9,289,436 | B2 | 3/2016 | Szmulewitz et al. |
| 9,314,473 | B2 | 4/2016 | Altschul et al. |
| 9,320,747 | B1 | 4/2016 | Altschul et al. |
| 9,422,323 | B2 | 8/2016 | Houpis et al. |
| 9,623,032 | B2 | 4/2017 | Pan et al. |
| 9,707,223 | B2 | 7/2017 | Hunt et al. |
| 9,801,893 | B2 | 10/2017 | Szmulewitz et al. |
| 9,829,495 | B2 | 11/2017 | Moraitis |
| 9,943,505 | B2 | 4/2018 | Hunt et al. |
| 9,956,216 | B2 | 5/2018 | Hunt et al. |
| 10,047,082 | B2 | 8/2018 | Hunt et al. |
| 10,071,130 | B2 | 9/2018 | Conzen |
| 10,117,852 | B2 | 11/2018 | Hunt et al. |
| 10,213,414 | B2 | 2/2019 | Hunt et al. |
| 10,300,076 | B2 | 5/2019 | Szmulewitz et al. |
| 10,323,034 | B2 | 6/2019 | Hunt et al. |
| 10,413,540 | B2 | 9/2019 | Hunt |
| 10,441,596 | B2 | 10/2019 | Pan et al. |
| 10,449,178 | B2 | 10/2019 | Hunt et al. |
| 10,456,392 | B2 | 10/2019 | Hunt et al. |

(Continued)

FOREIGN PATENT DOCUMENTS

| | | |
|---|---|---|
| EP | 0145121 A2 | 6/1985 |
| EP | 0375210 A1 | 6/1990 |

(Continued)

OTHER PUBLICATIONS

Drebert; Journal of Steroid Biochemistry & Molecular Biology 149 (2015) 92-105. (Year: 2015).\*

(Continued)

*Primary Examiner* — Daniel R Carcanague
(74) *Attorney, Agent, or Firm* — Kilpatrick Townsend & Stockton LLP

(57) ABSTRACT

Novel methods for treating cancer include: administering a glucocorticoid receptor modulator (GRM) to a patient, and determining whether or not the expression level of a gene is decreased in comparison with baseline levels of the gene measured in the patient prior to the GRM administration, thereby identifying a patient as being likely to benefit from cancer chemotherapy in conjunction with GRM administration where the expression level of a gene following GRM administration is decreased in comparison with corresponding gene baseline levels; and administering to said identified patient a combination of a GRM and cancer chemotherapy, whereby the cancer is treated in the patient.

The GRM may be selected from relacorilant, CORT125281, CORT122928, and CORT113176. The cancer chemotherapy agent may be a taxane. The gene expression level measured may be selected from 50 identified genes, and may be selected from COX2, DUSP1, GSK3b, MCL-1, PIK3CG, RGS-2, SGK1, and STAT3.

19 Claims, 19 Drawing Sheets

(56) References Cited

U.S. PATENT DOCUMENTS

| | | | |
|---|---|---|---|
| 10,568,880 B2 | 2/2020 | Hunt | |
| 10,646,474 B2 | 5/2020 | Hunt et al. | |
| 10,729,699 B2 | 8/2020 | Szmulewitz et al. | |
| 10,787,449 B2 | 9/2020 | Hunt et al. | |
| 10,898,478 B2 | 1/2021 | Hunt | |
| 11,234,971 B2 * | 2/2022 | Greenstein | A61K 31/4545 |
| 2002/0115613 A1 | 8/2002 | Kumar | |
| 2004/0102422 A1 | 5/2004 | Gaston | |
| 2005/0124533 A1 | 6/2005 | Schatzberg et al. | |
| 2006/0063748 A1 | 3/2006 | Belanoff | |
| 2006/0223852 A1 | 10/2006 | Gillespie et al. | |
| 2007/0128627 A1 | 6/2007 | Simons, Jr. et al. | |
| 2007/0281928 A1 | 12/2007 | Clark et al. | |
| 2008/0070950 A1 | 3/2008 | Benjamin et al. | |
| 2008/0287419 A1 | 11/2008 | Bruncko et al. | |
| 2009/0156672 A1 | 6/2009 | Budunova et al. | |
| 2010/0135956 A1 | 6/2010 | Gant et al. | |
| 2010/0179115 A1 | 7/2010 | Belanoff | |
| 2010/0292477 A1 | 11/2010 | Clark et al. | |
| 2011/0166110 A1 | 7/2011 | Clark et al. | |
| 2011/0269728 A1 | 11/2011 | Pan et al. | |
| 2012/0022121 A1 | 1/2012 | Dalton et al. | |
| 2012/0220565 A1 | 8/2012 | Clark et al. | |
| 2012/0238549 A1 | 9/2012 | Cusack et al. | |
| 2013/0225633 A1 | 8/2013 | Hunt et al. | |
| 2014/0038926 A1 | 2/2014 | Hunt et al. | |
| 2014/0186367 A1 | 7/2014 | Pan et al. | |
| 2014/0271455 A1 | 9/2014 | Pfeifer et al. | |
| 2014/0315866 A1 | 10/2014 | Pan et al. | |
| 2014/0341849 A1 | 11/2014 | Pan et al. | |
| 2015/0010503 A1 | 1/2015 | Szmulewitz et al. | |
| 2015/0080389 A1 | 3/2015 | Hunt et al. | |
| 2015/0118244 A1 | 4/2015 | Shahabi et al. | |
| 2015/0148341 A1 | 5/2015 | Hunt et al. | |
| 2015/0346210 A1 | 12/2015 | Nitta et al. | |
| 2016/0151388 A1 | 6/2016 | Szmulewitz et al. | |
| 2016/0215049 A1 | 7/2016 | Feldhaus et al. | |
| 2017/0020860 A1 | 1/2017 | Hunt et al. | |
| 2017/0182066 A1 | 6/2017 | Pan et al. | |
| 2017/0273972 A1 | 9/2017 | Hunt et al. | |
| 2018/0036318 A1 | 2/2018 | Szmulewitz et al. | |
| 2018/0064679 A1 | 3/2018 | Pierce et al. | |
| 2018/0071255 A1 | 3/2018 | Hunt et al. | |
| 2018/0193313 A1 | 7/2018 | Hunt et al. | |
| 2018/0280378 A1 | 10/2018 | Hunt | |
| 2019/0076424 A1 | 3/2019 | Hunt | |
| 2021/0369700 A1 * | 12/2021 | Hunt | A61P 35/00 |

FOREIGN PATENT DOCUMENTS

| | | |
|---|---|---|
| EP | 375210 B1 | 5/1995 |
| EP | 3074011 B1 | 7/2019 |
| JP | 322220 B | 4/1957 |
| JP | 04368384 A | 12/1992 |
| JP | 09505030 A | 5/1997 |
| JP | 2002506032 A | 2/2002 |
| JP | 2002544271 A | 12/2002 |
| JP | 2014530812 A | 11/2014 |
| JP | 2015517580 A | 6/2015 |
| WO | 9410150 A1 | 5/1994 |
| WO | 9504734 A1 | 2/1995 |
| WO | 9945925 A1 | 9/1999 |
| WO | 0069846 A1 | 11/2000 |
| WO | 03015692 A2 | 2/2003 |
| WO | 03061651 A1 | 7/2003 |
| WO | 2004065351 A1 | 8/2004 |
| WO | 2005087769 A1 | 9/2005 |
| WO | 2009058944 A2 | 5/2009 |
| WO | 2009064738 A2 | 5/2009 |
| WO | 2010132445 A1 | 11/2010 |
| WO | 2012027702 A1 | 3/2012 |
| WO | 2012094618 A1 | 7/2012 |
| WO | 2013039916 A1 | 3/2013 |
| WO | 2013052652 A1 | 4/2013 |
| WO | 2013177559 A2 | 11/2013 |
| WO | 2013177559 A3 | 1/2014 |
| WO | 2015061752 A1 | 4/2015 |
| WO | 2015070060 A1 | 5/2015 |
| WO | 2015077414 A1 | 5/2015 |
| WO | 2015077530 A1 | 5/2015 |
| WO | 2015095811 A2 | 6/2015 |
| WO | 2015100282 A1 | 7/2015 |
| WO | 2016055533 A1 | 4/2016 |
| WO | 2016141365 A1 | 9/2016 |
| WO | 2017023694 A1 | 2/2017 |
| WO | 2017151613 A1 | 9/2017 |
| WO | 2017216772 A2 | 12/2017 |
| WO | 2018049255 A1 | 3/2018 |

OTHER PUBLICATIONS

Orqueda; Biochemical Pharmacology 89 (2014) 526-535. (Year: 2014).*

Sundahl; Pharmacology & Therapeutics 152 (2015) 28-41. (Year: 2015).*

"Amorphous Materials: How Some Solids Flow Like Liquids", Science Daily, CNRS, Available online at http://www.sciencedaily.com/releases/2008/07/080704153507.htm, Jul. 7, 2008, pp. 1-3.

"Amorphous Solid", Wikepedia, Available Online at: http://en.wikipedia.org/wiki/Amorphous_solid, Jan. 16, 2014, 3 pages.

"Database Crossfile Beilstein", Beilstein Institut Zur Foerderung der Chemischen Wissenschaft, Accession No. 101172-52-5 (BRN), Jun. 27, 1988, 3 pages.

"Highlights of Prescribing Information", KORLYM® (Mifepristone), Corcept Therapeutics Incorporated, 2017, 7 pages.

"Study of Drug 1 (Enzalutamide) Plus Drug 2 (Relacorilant) for Patients With Prostate Cancer", ClinicalTrials.gov, Available online at: www.clinicaltrials.gov/ct2/show/NCT03674814, 9 pages.

"Study of Relacorilant in Combination with Nab-Paclitaxel for Patients with Recurrent Platinum-Resistant Ovarian, Fallopian Tube, or Primary Peritoneal Can", ClinicaiTrials.gov, Available online at www.clinicaltrials.gov/ct2/show/NCT03776812, 11 pages.

"Study to Evaluate Corti125134 in Combination with Nab-Paclitaxel in Patients with Solid Tumors", ClinicalTrials.gov, Available online at: www.clinicaltrials.gov/ct2/show/NCT02762981, 7 pages.

U.S. Appl. No. 12/777,340, "Declaration Under 37 CFR 1.132", Solid Forms and Process for Preparing, Feb. 2013, 5 pages.

Aherne, "Finding the Needle in the Haystack: Why Highthroughput Screening is Good for Your Health", Breast Cancer Research, vol. 4, Issue 4, 2002, pp. 148-154.

Antonarakis et al., "Emerging Therapeutic Approaches in the Management of Metastatic Castration Resistant Prostate Cancer", Prostate Ca. & Prostatic Dis., vol. 14, 2011, pp. 206-218.

Arora et al., "Glucocorticoid Receptor Confers Resistance to Antiandrogens by Bypassing Androgen Receptor Blockade", Cell, vol. 155, No. 6, Dec. 5, 2013, pp. 1309-1322.

Attard et al., "Translating Scientific Advancement into Clinical Benefit for Castration-Resistant Prostate Cancer Patients", Clin. Cancer. Res., vol. 1, Issue 12, Jun. 2011, pp. 3867-3875.

AU2013266110, "First Examiner Report", dated Sep. 19, 2016, 2 pages.

AU2014352915, "First Examiner/Examination Report", dated Feb. 6, 2018, 2 pages.

AU2017323636, "First Examination Report", dated Jul. 22, 2019, 4 pages.

AU2017323636, "Second Examination Report", dated Nov. 18, 2019, 3 pages.

Barth et al., "Structural and Stereoelectronic Requirements for the Inhibition of Mammalian 2,3-Oxidosqualene Cyclase by Substituted Isoquinoline Derivatives", J. Med. Chem., vol. 39, No. 12, American Chemical Society, Jun. 7, 1996, pp. 2302-2312.

Belanoff et al., "Selective Glucocorticoid Receptor {Type II} Antagonists Prevent Weight Gain Caused by Olanzapine in Rats", European Journal of Pharmacology, vol. 655, Issue 1-3, Mar. 25, 2011, pp. 117-120.

(56) References Cited

OTHER PUBLICATIONS

Belova et al., "Glucocorticoid Receptor Expression in Breast Cancer Associates with Older Patient Age", Breast Cancer Research and Treatment, vol. 116, Issue 3, Aug. 2009, pp. 441-447.
Benagiano et al., "Selective Progesterone Receptor Modulators 3: Use in Oncology, Endocrinology and Psychiatry", Expert Opin. Pharmacother, vol. 9, Issue 14, Oct. 2008, pp. 2487-2496.
Block et al., "Glucocorticoid Receptor Expression In 20 Solid Tumor Types Using Immunohistochemistry Assay", Cancer Management and Research, vol. 9, Mar. 6, 2017, pp. 65-72.
Bolton et al., "Cell- and Gene-Specific Regulation of Primary Target Genes by the Androgen Receptor", Genes Development, vol. 21, No. 16, Aug. 15, 2007, pp. 2005-2017.
Chan et al., "Prognostic Significance of Gleason Score 3+4 versus Gleason Score 4+3 Tumor at Radical Prostatectomy", Adult Urology, vol. 56, No. 5, Nov. 2000, pp. 823-827.
Check et al., "Evidence that Mifepristone, A Progesterone Receptor Antagonist, Can Cross the Blood Brain Barrier and Provide Palliative Benefits for Glioblastoma Multiforme Grade IV", Anticancer Research, vol. 34, No. 5, May 2014, pp. 2385-2388.
Check et al., "Mifepristone Causing Complete Remission of Rapidly Advancing Leukemia with Measurement of Progesterone-induced Blocking Factor", Anticancer Research, vol. 34, No. 5, May 2014, pp. 2413-2416.
Chen et al., "Androgen and Glucocorticoid Receptor Heterodimer Formation", J. Biol. Chem., vol. 272, No. 22, May 30, 1997, pp. 14087-14092.
Chen et al., "Mechanism of the Reversal Effect of Mifepristone on Drug Resistance of the Human Cervical Cancer Cell Line HELA/MMC", Genetics and Molecular Research, vol. 13, No. 1, 2014, pp. 1288-1295.
Chi et al., "Castration-Resistant Prostate Cancer: From New Pathophysiology to New Treatment Targets", Eur. Urol., vol. 56, Issue 4, Oct. 2009, pp. 594-605.
Cho et al., "Role of Activation Function Domain-1, DNA Binding, and Coactivator GRIP1 in the Expression of Partial Agonist Activity of Glucocorticoid Receptor-Antagonist Complexes", Biochemistry, vol. 44, Issue 9, 2005, pp. 3547-3561.
Christoffers et al., "Absolute Configuration of Methyl (+)-1,2,3,4,6,7,8,8a-Octahydro-6-isoquinolone-8a-carboxylate and Stereochemistry of a Copper-Catalyzed Asymmetric Michael Reaction", Zeitschrift Fuer Naturforschung B Chemical Sciences, vol. 59, No. 4, Apr. 1, 2004, pp. 375-379.
Christoffers et al., "Copper-Catalyzed Asymmetric Michael Reactions with α-Amino Acid Amides: Synthesis of an Optically Active Piperidine Derivative", Wiley Online Library, vol. 2002, No. 9, May 2002, pp. 1505-1508.
Christoffers et al., "Synthesis of an Optically Active Decahydro-6-Isoquinolone Scaffold with a Quaternary Stereocenter", Wiley Online Library, vol. 2004, No. 12, Jun. 2004, pp. 2701-2706.
Christoffers, "Transformation of an Optically Active Decahydro-6-isoquinolone Scaffold: Perfect Felkin-Anh Diastereoselectivity", Organic Letters, vol. 6, No. 7, American Chemical Society, Feb. 3, 2004, pp. 1171-1173.
Chu , "Connecting via Winsock to SIN at PTO-STN on Port 23", STN-12691012, STN International, Mar. 19, 2012, 62 pages.
Chu et al., "Successful Long-Term Treatment of Refractory Cushing's Disease with High-Dose Mifepristone (RU 486)", The Journal of Clinical Endocrinology & Metabolism, vol. 86, No. 8, Aug. 1, 2001, pp. 3568-3573.
Clark et al., "1H-Pyrazolo[3,4-g]Hexahydro-Isoquinolines as Selective Glucocorticoid Receptor Antagonists with High Functional Activity", Bioorganic & Medicinal Chemistry Letters, vol. 18, No. 4, Feb. 15, 2008, pp. 1312-1317.
Clark et al., "2-Benzenesulfonyl-8a-Benzyl-Hexahydro-2h-Isoquinolin-6-ones as Selective Glucocorticoid Receptor Antagonists", Bioorganic & Medicinal Chemistry Letters, vol. 17, No. 20, Oct. 15, 2007, pp. 5704-5708.
Clark , "Glucocorticoid Receptor Antagonists", Current Topics in Medicinal Chemistry, vol. 8, Issue 9, Jun. 1, 2008, pp. 813-838.

Cleutjens et al., "Both Androgen Receptor and Glucocorticoid Receptor Are Able to Induce Prostate-Specific Antigen Expression, but Differ in Their Growth-Stimulating Properties of LNCaP Cells", Endocrinology, vol. 138, Issue 12, Dec. 1, 1997, pp. 5293-5300.
Colleoni et al., "Response to Primary Chemotherapy in Breast Cancer Patients with Tumors Not Expressing Estrogen and Progesterone Receptors", Annals of Oncology, vol. 11, Issue 8, Aug. 1, 2000, pp. 1057-1059.
Cossu et al., "The Role of Mifepristone in Meningiomas Management: A Systematic Review of the Literature", BioMed Research International, vol. 2015, Article ID 267831, Jul. 2015, pp. 1-11.
Damia et al., "Contemporary Pre-clinical Development of Anticancer Agents—What are the Optimal Preclinical Models", European Journal of Cancer, vol. 45, No. 16, Nov. 2009, pp. 2768-2781.
Davies et al., "Association of Glucocorticoid Receptors with Prostate Nuclear Sites for Androgen Receptors and with Androgen Response Elements", J. Mol. Endocrin., vol. 5, Issue 2, Oct. 1990, pp. 117-127.
De Bono et al., "Abiraterone and Increased Survival in Metastatic Prostate Cancer", New England Journal of Medicine, vol. 364, No. 21, May 26, 2011, 19 pages.
Dennis, "Off by a Whisker", Nature, vol. 442, Aug. 7, 2006, pp. 739-741.
Desmedt et al., "Strong Time Dependence of the 76-Gene Prognostic Signature for Node-Negative Breast Cancer Patients in the TRANSBIG Multicenter Independent Validation Series", Clinical Cancer Research, vol. 13, Issue 11, Jun. 2007, pp. 3207-3214.
Di Lorenzo et al., "Castration-Resistant Prostate Cancer", Drugs, vol. 70, Issue 8, May 2010, pp. 983-1000.
Dibas et al., "Glucocorticoid Therapy and Ocular Hypertension", European Journal of Pharmacology, vol. 787, Sep. 15, 2016, pp. 57-71.
Donovan et al., "Androgen Receptor Expression is Associated with Prostate Cancer-Specific Survival in Castrate Patients with Metastatic Disease", BJU International, vol. 105, Issue 4, Feb. 2010, pp. 462-467.
Efstathiou et al., "Molecular Characterization of Enzalutamide-treated Bone Metastatic Castration-resistant Prostate Cancer", Eur. Uro., vol. 67, 2015, pp. 53-60.
Elmore, "Nonsteroidal Selective Glucocorticoid Modulatores: The Effect of C-5 Alkyl Substitution on the Transcriptional Activation/Repression Profile of 2,5-Dihydro-10-Methoxy-2,2,4-Trimethyl-1H-[1]Benzopyrano[3,4-f]Quinolines", American Chemical Society, J. Med. Chem., vol. 44, No. 25, Dec. 1, 2001, pp. 4481-4491.
EP13751132.5, "Extended European Search Report", dated Mar. 21, 2016, 14 pages.
EP13751132.5, "Partial Supplementary European Search Report", dated Sep. 7, 2015, 6 pages.
EP13793417.0, "Extended European Search Report", dated Jan. 4, 2016, 7 pages.
EP14863514.7, "Extended European Search Report", dated May 4, 2017, 6 pages.
EP16183642.4, "Extended European Search Report", dated Dec. 1, 2016, 12 pages.
EP17760608.4, "Extended European Search Report", dated Oct. 9, 2019, 10 pages.
EP17849673.3, "Extended European Search Report", dated Mar. 26, 2020, 11 pages.
EP18154256.4, "Extended European Search Report", dated Mar. 26, 2018, 6 pages.
EP19177963.6, "Extended European Search Report", dated Jul. 25, 2019, 5 pages.
EP19188885.8, "Extended European Search Report", dated Oct. 28, 2019, 6 pages.
Fakih et al., "Glucocorticoids and Treatment of Prostate Cancer: A Preclinical and Clinical Review", Urology, vol. 60, Issue 4, Oct. 2002, pp. 553-561.
Fiorentino et al., "Blood and Tissue Biomarkers in Prostate Cancer: State of the Art", Urol Clin. North. Am., vol. 37, Issue 1, Feb. 2010, pp. 1-14.
Fradet, "PSA and Beyond: Biomarkers in Prostate Cancer Diagnosis and Prognosis", Curr. Opin. Urol., vol. 19, Issue 3, May 2009, pp. 243-246.

(56) References Cited

OTHER PUBLICATIONS

Gaddy et al., "Mifepristone Induces Growth Arrest, Caspase Activation, and Apoptosis of Estrogen Receptor-Expressing, Antiestrogen-Resistant Breast Cancer Cells", Clinical Cancer Research, vol. 10, Issue 15, Aug. 1, 2004, pp. 5215-5225.
Gasparini et al., "Peripheral Markers in Testing Pathophysiological Hypotheses and Diagnosis Alzheimer's Disease", FASEB. J., vol. 12, 1998, pp. 17-34.
Gauthier et al., "Alzheimer's Disease: Current Knowledge, Management and Research", Can. Med. Assoc. J., vol. 157, No. 8, Oct. 15, 1997, pp. 1047-1052.
Genck, "Make the Most of Antisolvent Crystallization; A Number of Factors can Affect Solids' Formation", Available Online at: https://www.chemicalprocessing.com/articles/2010/210/, Nov. 8, 2010, 8 pages.
Greicius et al., "Presenile Dementia Syndrome: An Update on Taxonomy and Diagnosis", Journal of Neurol, Neurosurg, Psychiatry, vol. 72, 2002, pp. 691-700.
Grover et al., "The Initiation of Breast and Prostate Cancer", Carcinogenesis, vol. 23, Issue 7, Jul. 1, 2002, pp. 1095-1102.
Gulliver, "Xenobiotics and the Glucocorticoid Receptor", Toxicology and Applied Pharmacology, vol. 319, Mar. 15, 2017, pp. 69-79.
Guo et al., "A Novel Androgen Receptor Splice Variant Is Up-Regulated During Prostate Cancer Progression and Promotes Androgen Depletion-Resistant Growth", Cancer Res., vol. 69, Issue 6, Mar. 15, 2009, pp. 2305-2313.
Guo et al., "A Novel Androgen Receptor Splice Variant Is Up-regulated during Prostate Cancer Progression and Promotes Androgen Depletion-Resistant Growth", Cancer Res., vol. 69, No. 6, 2009, 21 pages.
Gupta et al., "Studies on Carboxylation in Heterocyclic Systems", J. Sci. Industr., Res., vol. 20B, Aug. 1961, pp. 394-397.
Gura, "Systems for Identifying New Drugs are Often Faulty", Science, vol. 278, No. 5340, Cancer Models, Nov. 7, 1997, pp. 1041-1042.
Han et al., "Biochemical (Prostate Specific Antigen) Recurrence Probability Following Radical Prostatectomy for Clinically Localized Prostate Cancer", J. Urol., vol. 169, Issue 2, Feb. 2003, pp. 517-523.
He et al., "Discovery of a Highly Potent Glucocorticoid for Asthma Treatment", Cell Discovery, vol. 1, No. 15035, 2015, 13 pages.
Hein et al., "Click Chemistry, A powerful Tool for Pharmaceutical Sciences", Pharmaceutical Research, vol. 25, Issue 10, Oct. 2008, pp. 2216-2230.
Henderson et al., "Estrogens as a Cause of Human Cancer: the Richard and Hinda Rosenthal Foundation Award Lecture", Cancer Research, vol. 48, Issue 2, Jan. 15, 1988, pp. 246-253.
Hinrichs et al., "Glucocorticoids Do Not Inhibit Antitumor Activity of Activated CD8+ T Cells," J Immunother. (2005) 28(6):517-524.
Ho et al., "A Complex Response Element in Intron 1 of the Androgen-Regulated 20-kDa Protein Gene Displays Cell Type-Dependent Androgen Receptor Specificity", J. Biol. Chem., vol. 268, No. 36, Dec. 25, 1993, pp. 27226-27235.
Hsin et al., "Stereoselective Synthesis of Morphine Fragments Trans- and Cisoctahydro- 1H-Benzo[4,5]Furo[3,2-e]Isoquinolines", Elsevier Ltd., Tetrahedron, vol. 61, No. 2, Jan. 10, 2005, pp. 513-520.
Huang et al., "Reversal Effect of Mifepristone on Adriamycin Resistance in Human Breast Cancer Cell Line MCF-7/ADM in Vitro and in Vivo", Journal of Central South University, Medical Sciences, vol. 35,No. 6, Jun. 2010, pp. 576-583.
Hunt et al., "Identification of the Clinical Candidate (R)-(1-(4-Fluorophenyl)-6-((1-Methyl-1H-Pyrazol-4-yl)Sulfonyl)-4,4a,5,6,7,8-Hexahydro-1H-Pyrazolo[3,4-g]Isoquinolin-4a-yl)(4-(Trifluoromethyl)Pyridin-2-yl)Methanone (CORT125134): A Selective Glucocorticoid Receptor", Journal of Medicinal Chemistry, vol. 60, No. 8, Apr. 27, 2017, pp. 3405-3421.
Hunt et al., "Preclinical Efficacy of the Selective GR antagonist, CORT125134", American Association for Cancer Research, 2017, 1 page.
Iams et al., "PD-1 Inhibition and PD-1 Inhibitors", My Cancer Genome, Nov. 24, 2015, pp. 1-5.
Isikbay et al., "Glucocorticoid Receptor Activity Contributes to Resistance to Androgen-Targeted Therapy in Prostate Cancer", Horm. Canc.vol. 5, 2014, pp. 72-89.
Jemal et al., "Cancer Statistics", CA: A Cancer Journal for Clinicians, vol. 60, Issue 5, Sep.-Oct. 2010, pp. 277-300.
Johnson et al., "Relationships Between Drug Activity in NCI Preclinical in Vitro and in Vivo Models and Early Clinical Trials", British Journal of Cancer, vol. 84, No. 10, May 18, 2001, pp. 1424-1431.
Kach et al., "Glucocorticoid Receptor Signaling in Breast and Prostate Cancers: Emergence as a Therapeutic Target", Science Translational Medicine, vol. 7, No. 305, Sep. 16, 2015, pp. 1-9.
Kach et al., "Selective Glucocorticoid Receptor Modulators (SGRMs) Delay Castrate-Resistant Prostate Cancer Growth", Molecular Cancer Therapeutics, vol. 16, No. 8, Aug. 2017, pp. 1680-1692.
Kadmiel et al., "Glucocorticoid Receptor Signaling in Health and Disease", Trends in Pharmacological Sciences, vol. 34, No. 9, Sep. 2013, pp. 518-530.
Karantanos et al., "Understanding the Mechanisms of Androgen Deprivation Resistance in Prostate Cancer at the Molecular Level", Eur. Urol., vol. 67, No. 1, 2015, pp. 470-479.
Keen et al., "The Biology of Breast Carcinoma", Cancer, vol. 97, No. 3, Feb. 1, 2003, pp. 825-833.
Kim et al., "Current Treatment Strategies for Castration-Resistant Prostate Cancer", Korean Journal of Urology, vol. 52, No. 3, Mar. 2011, pp. 157-165.
Klein et al., "Analyzing Survival Curves at a Fixed Point in Time", Stat. Med., vol. 26, Issue 24, Oct. 30, 2007, pp. 4505-4519.
Klijn et al., "Antiprogestins a New Form of Endocrine Therapy for Human Breast Cancer", Cancer Research, vol. 49, Issue 11, Jun. 1, 1989, pp. 2851-2856.
Kondo et al., "A Case of Ectopic Adrenocorticotropic Hormone-Producing Pancreatic Neuroendocrine Tumor with Multiple Liver Metastases", Endocr J., vol. 57, No. 3, Apr. 2010, pp. 229-236.
Koochekpour, "Androgen Receptor Signaling and Mutations in Prostate Cancer", Asian J. Androl., vol. 12, Issue 5, Sep. 2010, pp. 639-657.
Kriaucionis et al., "The Nuclear DNA Base 5-Hydroxymethylcytosine is Present in Brain and Enriched in Purkinje Neurons", Science, vol. 324, No. 5929, May 15, 2009, 5 pages.
Kugita, "Studies on the Syntheses of Hydrogenated Quinolines and Isoquinolines as Analgesics", Pharmaceutical Bulletin, vol. 4, No. 1, Feb. 1956, pp. 29-34.
Lee et al., "A New Addition to the PD-1 Checkpoint Inhibitors for Non-Small Cell Lung Cancer—The Anti-PDL1 Antibody—MEDI4736", Translational Lung Cancer Research, vol. 3, No. 6, Dec. 2014, pp. 408-410.
Li et al., "High Level of Androgen Receptor is Associated with Aggressive Clinicopathologic Features and Decreased Biochemical Recurrence-Free Survival in Prostate: Cancer Patients Treated with Radical Prostatectomy", Am. J. Surg. Pathol., vol. 28, No. 7, Jul. 2004, pp. 928-934.
Loi et al., "Definition of Clinically Distinct Molecular Subtypes in Estrogen Receptor-Positive Breast Carcinomas Through Genomic Grade", Journal of Clinical Oncology, vol. 25, No. 10, Apr. 1, 2007, pp. 1239-1246.
Loi et al., "Predicting Prognosis Using Molecular Profiling in Estrogen Receptor-Positive Breast Cancer Treated With Tamoxifen", BMC Genomics, vol. 9, No. 239, May 22, 2008, pp. 1-12.
Lotan et al., "Up-Regulation of MKK4, MKK6 and MKK7 During Prostate Cancer Progression: An Important Role for SAPK Signalling in Prostatic Neoplasia", J. Pathol., vol. 212, Issue 4, Aug. 2007, pp. 386-394.
Lucci et al., "Modification of Ceramide Metabolism Increases Cancer Cell Sensitivity to Cytotoxics", Int J. Onco., vol. 15, Issue 3, Sep. 1999, pp. 541-546.
Ma et al., "IL-21 Activates Both Innate and Adaptive Immunity to Generate Potent Antitumor Responses that Require Perforin but Are Independent of IFN-Gamma", J. Jmmunol, vol. 171, Issue 2, Jul. 15, 2003, pp. 608-615.

(56) References Cited

OTHER PUBLICATIONS

Magee et al., "Construction of Cis- and Trans- Decahydroisoquinolines via Heterogeneous Catalytic Hydrogenation", J. Org. Chem., American Chemical Society, vol. 64, No. 7, Mar. 16, 1999, pp. 2549-2554.

Mahmood et al., "3D-QSAR Comfa, Comsia Studies on Pyrazolo-Fused Azadecalins Derivatives as Selective Glucocorticoid Receptor Antagonists", Pharma Science Monitor, vol. 3, Issue 3, Jul. 2012, pp. 2027-2055.

Makarov et al., "Updated Nomogram to Predict Pathologic Stage of Prostate Cancer Given Prostate-Specific Antigen Level, Clinical Stage, and Biopsy Gleason Score (Partin Tables) Based on Cases from 2000 to 2005", Urology, vol. 69, Issue 6, Jun. 2007, pp. 1095-1101.

Melhem et al., "Administration of Glucocorticoids to Ovarian Cancer Patients is Associated with Expression of the Anti-apoptotic Genes SGK1 and MKP1/DUSP1 in Ovarian Tissues", Clinical Cancer Research, vol. 15, No. 9, May 1, 2009, pp. 3196-3204.

Mikosz et al., "Glucocorticoid Receptor-Mediated Protection from Apoptosis is Associated with Induction of the Serine/Threonine Survival Kinase Gene, sgk-1", The Journal of Biological Chemistry, vol. 276, No. 20, Feb. 13, 2001, pp. 16649-16654.

Minn et al., "Genes that Mediate Breast Cancer Metastasis to Lung", Nature, vol. 436, No. 7050, Jul. 28, 2005, pp. 518-524.

Mohler et al., "Androgen and Glucocorticoid Receptors in the Stroma and Epithelium of Prostatic Hyperplasia and Carcinoma", Clin. Cancer Res., vol. 2, Issue 5, May 1996, pp. 889-895.

Moller et al., "Impact of New Technologies for Cellular Screening along the Drug Value Chain", Drug Discovery Today, vol. 14, No. 9-10, May 2010, pp. 384-390.

Montgomery et al., "Impact of Baseline Corticosteroids on Survival and Steroid Androgens in Metastatic Castration-Resistant Prostate Cancer: Exploratory Analysis from COU-AA-301", Eur. Urology, vol. 67, No. 5, 2014, 8 pages.

Moran et al., "The Glucocorticoid Receptor Mediates a Survival Signal in Human Mammary Epithelial Cells", Cancer Research, vol. 60, Issue 4, Feb. 15, 2000, pp. 867-872.

Moses et al., "The Growing Applications of Click Chemistry", Chem Soc Rev., vol. 36, Issue 8, May 2007, pp. 1249-1262.

Mottet et al., "EAU Guidelines on Prostate Cancer. Part II: Treatment of Advanced, Relapsing, and Castration-Resistant Prostate Cancer", Eur. Urol., vol. 59, Jan. 2011, pp. 572-583.

Munster et al., "A Phase 1/2 Study of Relacorilant + Nab-Paclitaxel (Nabpac) in Patients (Pts) with Solid Tumors: The Dose-Finding Phase", Journal of Clinical Oncology, vol. 36, No. 15, May 20, 2018, 4 pages.

Munster et al., "A Phase 1/2 Study of Relacorilant + Paclitaxel in Patients with Solid Tumors: The Dose-Finding Phase", American Association for Cancer Research, 2018, 1 page.

Nakawatase et al., "Alzheimer's Disease and Related Dementia", Cecil's Textbook of Medicine, Twenty-First Edition, vol. 1. W. B. Saunders Company, 2000, pp. 2042-2045.

Niemeier et al., "Androgen Receptor in Breast Cancer: Expression in Estrogen Receptor-Positive Tumors and in Estrogen Receptor-Negative Tumors with Apocrine Differentiation", Modern Pathology, vol. 23, No. 2, 2010, pp. 205-212.

Nocentini et al., "A New Member of the Tumor Necrosis Factorynerve Growth Factor Receptor Family Inhibits T Cell Receptor-Induced Apoptosis", Proc. Natl. Acad. Sci., vol. 94, Jun. 1997, pp. 6216-6221.

Norman et al., "Functional Glucocorticoid Receptor Modulates Pancreatic Carcinoma Growth through an Autocrine Loop", J. Surg. Res., vol. 57, No. 1, Jul. 1994, pp. 33-38.

Novotny et al., "Cancer Therapy: New Targets for Chemotherapy", Hematology, vol. 8, No. 3, Jun. 2003, pp. 129-137.

Ocana et al., "Preclined Development of Molecular-Targeted Agents for Cancer", Nature Reviews Clinical Oncology Review, vol. 8, No. 4, Apr. 2011, pp. 200-209.

Ohlmann et al., "Novel Options for the Treatment of Castration-Resistant Prostate Cancer", World J. Urol., vol. 30, No. 4, Aug. 2012, pp. 495-503.

Pan et al., "Activation of the Glucocorticoid Receptor is Associated with Poor Prognosis in Estrogen Receptor-Negative Breast Cancer", Cancer Research, vol. 71, No. 20, Oct. 15, 2011, 21 pages.

Pan et al., "Identification of Glucocorticoid Receptor (GR) Signatures in Primary Human Breast Cancer: Association with Relapse-Free Survival Time", Poster Presented by S.D. Conzen as a Short Talk, presented at Nuclear Receptors: Signaling, Gene Regulation and Cancer, Keystone Symposia on Molecular and Cellular Biology, Keystone Resort, Keystone, Colorado, Mar. 25, 2010, 1 page.

Pang et al., "Dexamethasone Decreases Xenograft Response to Paclitaxel Through Inhibition of Tumor Cell Apoptosis", Cancer Biology & Therapy, vol. 5, Issue 8, Aug. 2006, pp. 933-940.

PCT/US13/27720, "International Search Report and Written Opinion", dated Jun. 17, 2013, 9 pages.

PCT/US2005/008049, "International Search Report and Written Opinion", dated Jun. 15, 2005, 8 pages.

PCT/US2010/034382, "International Search Report and Written Opinion", dated Jul. 9, 2010, 7 pages.

PCT/US2011/049408, "International Search Report and Written Opinion", dated Jan. 30, 2012, 10 pages.

PCT/US2013/027150, "International Preliminary Report on Patentability", dated Sep. 4, 2014, 7 pages.

PCT/US2013/027150, "International Search Report and Written Opinion", dated Apr. 29, 2013, 9 pages.

PCT/US2013/027720, "International Search Report and Written Opinion", dated Jun. 17, 2013, 8 pages.

PCT/US2014/066759, "International Preliminary Report on Patentability", dated Jun. 9, 2016, 6 pages.

PCT/US2014/066759, "International Search Report and Written Opinion", dated Feb. 6, 2015, 9 pages.

PCT/US2017/019948, "International Preliminary Report on Patentability", dated Sep. 13, 2018, 6 pages.

PCT/US2017/019948, "International Search Report and Written Opinion", dated May 25, 2017, 12 pages.

PCT/US2017/050812, "International Preliminary Report on Patentability", dated Mar. 21, 2019, 12 pages.

PCT/US2017/050812, "International Search Report and Written Opinion", dated Dec. 26, 2017, 17 pages.

PCT/US2018/025547, "International Preliminary Report on Patentability", dated Oct. 10, 2019, 10 pages.

PCT/US2018/025547, "International Search Report and Written Opinion", dated Aug. 9, 2018, 13 pages.

PCT/US2019/067138, "International Search Report and Written Opinion", dated Apr. 24, 2020, 10 pages.

Peeters et al., "Differential Effects of the New Glucocorticoid Receptor Antagonist ORG 34517 and RU486 (Mifepristone) on Glucocorticoid Receptor Nuclear Translocation in the AtT20 Cell Line", Ann. NY Acad. Sci., vol. 1148, Issue 1, Dec. 2008, pp. 536-541.

P'Eng et al., "Glucocorticoid Receptors in Hepatocellular Carcinoma and Adjacent Liver Tissue", Cancer, vol. 62, No. 10, Nov. 15, 1988, pp. 2134-2138.

Petrylak et al., "Evaluation of Prostate-Specific Antigen Declines for Surrogacy in Patients Treated on SWOG 99-16", J. Natl. Cancer Inst., vol. 98, Issue 8, Apr. 19, 2006, pp. 516-521.

Pike et al., "Estrogens, Progestogens, Normal Breast Cell Proliferation, and Breast Cancer Risk", Epidemiologic Rev., vol. 15, Issue 1, Jan. 1, 1993, pp. 17-30.

Pound et al., "Natural History of Progression after PSA Elevation Following Radical Prostatectomy", JAMA, vol. 281, No. 17, May 5, 1999, pp. 1591-1597.

Ramsay, "Immune Checkpoint Blockade Immunotherapy to Activate Anti-Tumour T-Cell Immunity", British Journal of Haematology, vol. 162, No. 3, Aug. 2013, pp. 313-325.

Rauhala et al., "Dual-Specificity Phosphatase 1 and Serum/Glucocorticoid-Regulated Kinase are Downregulated in Prostate Cancer", Int. J. Cancer, vol. 117, Issue 5, Dec. 10, 2005, pp. 738-745.

Reagan-Shaw et al., "Dose Translation from Animal to Human Studies Revisited", The Faseb Journal, vol. 22, Mar. 2007, pp. 659-661.

(56) References Cited

OTHER PUBLICATIONS

Rehn et al., "Antiinflammatory Action of Glucocorticoids—New Mechanisms for Old Drugs", The New England Journal of Medicine, vol. 353, No. 16, Oct. 20, 2005, pp. 1711-1723.
Ring et al., "Mechanisms of Tamoxifen Resistance", Endocrine-Related Cancer, vol. 11, Issue 4, Dec. 2004, pp. 643-658.
Robinson et al., "Octahydrophenanthrene-2,7-diol Analogues as Dissociated Glucocorticoid Receptor Agonists: Discovery and Lead Exploration", J. Med. Chem., vol. 52, No. 6, 2009, pp. 1731-1743.
Rosner et al., "Higher Tumor to Benign Ratio of the Androgen Receptor mRNA Expression Associates with Prostate Cancer Progression after Radical Prostatectomy", Urology, vol. 70, Issue 6, Dec. 2007, pp. 1225-1229.
Sahoo et al., "Coordinate Expression of the PI3-Kinase Downstream Effectors Serum and Glucocorticoid-Induced Kinase (SGK-1) and Akt-1 in Human Breast Cancer", European Journal of Cancer, vol. 41, Issue 17, Nov. 2005, pp. 2754-2759.
Sahu et al., "FoxA1 Specifies Unique Androgen and Glucocorticoid Receptor Binding Events in Prostate Cancer Cells", Cancer Res., vol. 73, Issue 5, Mar. 2013, pp. 1570-1580.
Sausville et al., "Contributions of Human Tumor Xenografts to Anticancer Drug Development", Cancer Research, vol. 66, No. 7, Apr. 2006, pp. 3351-3354.
Schenone et al., "Target Identification and Mechanism of Action in Chemical Biology and Drug Discovery", Nature Chemical Biology, vol. 9, Issue 4, 2013, pp. 232-240.
Scher et al., "Antitumour Activity of Mdv3100 in Castration-Resistant Prostate Cancer: A Phase 1-2 Study", Lancet, vol. 375, No. 9724, Apr. 24, 2010, pp. 1437-1446.
Scher et al., "Biology of Progressive, Castration-Resistant Prostate Cancer: Directed Therapies Targeting the Androgen-Receptor Signaling Axis", Journal of Clinical Oncology, vol. 23, No. 32, Nov. 10, 2005, pp. 8253-8261.
Scher et al., "End Points and Outcomes in Castration-Resistant Prostate Cancer: From Clinical Trials to Clinical Practice", J. Clin. Oncol., vol. 29, No. 27, Sep. 20, 2011, pp. 3695-3704.
Schlossmacher et al., "Glucocorticoid Receptor-Mediated Apoptosis: Mechanisms of Resistance In Cancer Cells", Journal of Endocrinology, vol. 211, No. 1, Oct. 2011, pp. 17-25.
Schultz et al., "Heteroatom Directed Photoarylation. Synthetic Potential of the Heteroatom Oxygen", Journal of the American Chemical Society, vol. 100, No. 7, Mar. 29, 1978, pp. 2150-2162.
Schultz et al., "Studies Directed at a Synthesis of the Morphine Alkaloids. A Photochemical Approach", J. Org. Chem., American Chemical Society, vol. 50, No. 2, Jan. 1985, pp. 217-231.
Segovia-Mendoza et al., "Antihormonal Agents as a Strategy to Improve the Effect of Chemo-Radiation in Cervical Cancer: In Vitro and in Vivo Study", BMC Cancer, vol. 15, No. 21, 2015, pp. 1-11.
Seruga et al., "Drug Resistance in Metastatic Castration-Resistant Prostate Cancer", Nature Reviews Clinical Oncology, vol. 8, No. 1, Jan. 2011, pp. 12-23.
Shanmugam et al., "Serum/Glucocorticoid-Induced Protein Kinase-1 Facilitates Androgen Receptor-Dependent Cell Survival", Cell Death Differ, vol. 14, No. 12, Oct. 12, 2007, pp. 2085-2094.
Sharma et al., "Cell Line-Based Platforms to Evaluate the Therapeutic Efficacy of Candidate Anticancer Agents", Nature Reviews Cancer, vol. 10, No. 4, Apr. 2010, pp. 241-253.
Sherk et al., "Development of a Small Molecule Serum and Glucocorticoid-Regulated Kinase 1 Antagonist and its Evaluation as a Prostate Cancer Therapeutic", Cancer Res., vol. 68, Issue 18, Sep. 2008, 20 pages.
Sims et al., "The Removal of Multiplicative, Systematic Bias Allows Integration of Breast Cancer Gene Expression Datasets—Improving Meta-Analysis and Prediction of Prognosis", BMC Medical Genomics, vol. 1, No. 42, Sep. 21, 2008, pp. 1-14.
Skor et al., "Glucocorticoid Receptor Antagonism as a Novel Therapy for Triple-Negative Breast Cancer", Clinical Cancer Research, vol. 19, No. 22, Nov. 15, 2013, pp. 6163-6172.
Smith et al., "Expression of Glucocorticoid and Progesterone Nuclear Receptor Genes in Archival Breast Cancer Tissue", Breast Cancer Research, vol. 5, Issue 1, 2003, pp. R9-R12.
Smith et al., "Progesterone, Glucocorticoid, but not Estrogen Receptor mRNA is Altered in Breast Cancer Stroma", Cancer Letters, vol. 255, Issue 1, Sep. 18, 2007, pp. 77-84.
Song et al., "Dihydrotestosterone Enhances Castration-Resistant Prostate Cancer Cell Proliferation through STAT5 Activation via Glucocorticoid Receptor Pathway", The Prostate, vol. 74, Issue 12, Sep. 2014, pp. 1240-1248.
Sorlie et al., "Gene Expression Patterns of Breast Carcinomas Distinguish Tumor Subclasses with Clinical Implications", Proc. Nat. Acad. Sci., vol. 98, No. 19, Sep. 11, 2001, pp. 10869-10874.
Sotiriou et al., "Gene Expression Profiling in Breast Cancer: Understanding the Molecular Basis of Histologic Grade to Improve Prognosis", Journal of the National Cancer Institute, vol. 98, No. 4, Feb. 15, 2006, pp. 262-272.
Spitz et al., "Mifepristone (RU 486)—A Modulator of Progestin and Glucocorticoid Action", The New England Journal of Medicine, Massachusetts Medical Society, vol. 329, No. 6, Aug. 5, 1993, pp. 404-412.
Srinivas et al., "Phase II Study Evaluating Oral Triamcinolone in Patients with Androgen-Independent Prostate Cancer", Adult Urology, vol. 67, No. 5, May 1, 2006, pp. 1001-1006.
Srinivas et al., "Proteomics for Cancer Biomarker Discovery", Clinical Chemistry, vol. 48, Issue 8, Aug. 2002, pp. 1160-1169.
Stephenson et al., "Preoperative Nomogram Predicting the 10-Year Probability of Prostate Cancer Recurrence After Radical Prostatectomy", J. Natl. Cancer Inst., vol. 98, No. 10, May 17, 2006, 7 pages.
Sterbis et al., "Higher Expression of the Androgen-Regulated Gene PSA-HK3 mRNA in Prostate Cancer Tissues Predicts Biochemical Recurrence-Free Survival", Clin. Cancer Res., vol. 14, Issue 3, Feb. 2008, pp. 758-763.
Stringer-Reasor et al., "Glucocorticoid Receptor Activation Inhibits Chemotherapy-Induced Cell Death in High-Grade Serous Ovarian Carcinoma", Gynecologic Oncology, vol. 138, Issue 3, Sep. 2015, pp. 656-662.
Sui et al., "Estrogen Receptor α Mediates Breast Cancer Cell Resistance to Paclitaxel through Inhibition of Apoptotic Cell Death", Cancer Research, vol. 67, Issue 11, Jun. 1, 2007, pp. 5337-5344.
Sun et al., "Castration Resistance in Human Prostate Cancer is Conferred by a Frequently Occurring Androgen Receptor Splice Variant", J. Clin. Invest., vol. 120, No. 8, 2010, pp. 2715-2730.
Sun et al., "Castration Resistance in Human Prostate Cancer is Conferred by a Frequently Occurring Androgen Receptor Splice Variant", J Clin Invest., vol. 120, Issue 8, Aug. 2, 2010, pp. 2715-2730.
Sundahl et al., "Selective Glucocorticoid Receptor-Activating Adjuvant Therapy in Cancer Treatments", Oncoscience, vol. 3, No. 7-8, Jul. 2016, pp. 188-202.
Szmulewitz et al., "Serum/Glucocorticoid-Regulated Kinase 1 Expression in Primary Human Prostate Cancers", Prostate, vol. 72, Issue 2, Feb. 1, 2018=2, pp. 157-164.
Tannock et al., "Docetaxel Plus Prednisone or Mitoxantrone Plus Prednisone for Advanced Prostate Cancer", The New England Journal of Medicine, vol. 351, No. 15, Oct. 7, 2004, pp. 1502-1512.
Taplin et al., "A Phase II Study of Mifepristone (Ru-486) in Castration-Resistant Prostate Cancer, with a Correlative Assessment of Androgen-Related Hormones", BJU International, vol. 101, Issue 9, May 1, 2008, pp. 1084-1089.
Tessier et al., "Serum and Glucocorticoid-Regulated Protein Kinases: Variations on a Theme", Journal of Cellular Biochemistry, vol. 98, Issue 6, Aug. 15, 2006, pp. 1391-1407.
Touat et al., "Successful Treatment of Multiple Intracranial Meningiomas with the Antiprogesterone Receptor Agent Mifepristone (RU486)", Acta Neurochirurgica, vol. 156, No. 10, Oct. 2014, pp. 1831-1835.
Twiddy et al., "Cholesterol as a Potential Target for Castration-Resistant Prostate Cancer", Pharm. Res., vol. 28, Issue 3, Mar. 2011, pp. 423-437.
Uchida et al., "An Efficient Access to the Optically Active Manzamine Tetracyclic Ring System", Tetrahedron Letters, vol. 40, Issue 1, Jan. 1, 1999, pp. 113-116.

(56) References Cited

OTHER PUBLICATIONS

Venkatesh et al., "Role of the Development Scientist in Compound Lead Selection and Optimization", Journal of Pharmaceutical Sciences, vol. 89, Issue 2, Feb. 2000, pp. 145-154.

Von Hoff et al., "Increased Survival in Pancreatic Cancer with Nab-Paclitaxel Plus Gemcitabine", The New England Journal of Medicine, vol. 369, 2013, pp. 1691-1703.

Wang et al., "Gene-Expression Profiles to Predict Distant Metastasis of Lymph-Node-Negative Primary Breast Cancer", The Lancet, vol. 365, Issue 9460, Feb. 19-25, 2005, pp. 671-679.

Ward et al., "Rising Prostate-Specific Antigen after Primary Prostate Cancer Therapy", Nat. Clin. Pract. Urol., vol. 2, No. 4, Apr. 1, 2005, pp. 174-182.

West et al., "Abstract PD3-02: Second-Generation Selective Glucocorticoid Receptor Modulators in Triple-Negative Breast Cancer", Cancer Research, vol. 76, No. 4, Feb. 2016, 2 pages.

White, "Sygnature Discovery Delivers Clinical Candidate CORT125134 to Corcept", Sygnature Discovery News, https://www.drugtargetreview.com/news/5589/sygnature-discovery-delivers-clinical-candidate-cort125134-to-corcept/, Jul. 30, 2015, pp. 1-2.

Wright et al., "Differences in Prostate Cancer Outcomes Between Cases With Gleason 4+3 and Gleason 3+4 Tumors in a Population Based Cohort", J. Urol., vol. 182, Issue 6, Dec. 2009, pp. 2702-2707.

Wu et al., "Glucocorticoid Receptor Activation Signals through Forkhead Transcription Factor 3a in Breast Cancer Cells", Mol. Endocrinol, vol. 20, No. 10, Oct. 1, 2006, pp. 2304-2314.

Wu et al., "Microarray Analysis Reveals Glucocorticoid-Regulated Survival Genes that are Associated with Inhibition of Apoptosis in Breast Epithelial Cells", Cancer Research, vol. 64, Issue 5, Mar. 1, 2004, pp. 1757-1764.

Wu et al., "Prevalent Expression of the Immunostimulatory MHC Class I Chain-Related Molecule Is Counteracted by Shedding in Prostate Cancer", J. Clin. Invest., vol. 114, Issue 4, Aug. 16, 2004, pp. 560-568.

Xie et al., "The Expression of Glucocorticoid Receptor is Negatively Regulated by Active Androgen Receptor Signaling in Prostate Tumors", Int. J. Cancer, vol. 136, 2015, pp. E27-E38.

Yan et al., "Relationship between Glucocorticoid Receptor Signal Pathway and Androgen-Independent Prostate Cancer", Urologia Internationalis, vol. 81, Issue 2, 2008, pp. 228-233.

Yemelyanov et al., "Differential Targeting of Androgen and Glucocorticoid Receptors Induces ER Stress and Apoptosis in Prostate Cancer Cells", Cell Cycle, vol. 11, Issue 2, Jan. 15, 2012, pp. 395-406.

Yemelyanov et al., "Tumor Suppressor Activity of Glucocorticoid Receptor in the Prostate", Oncogene, vol. 26, No. 13, Mar. 22, 2007, pp. 1885-1896.

Yu et al., "Systems Pharmacology of Mifepristone (RU486) Reveals its 47 Hub Targets and Network: Comprehensive Analysis and Pharmacological Focus on FAK-Src-Paxillin complex", Scientific Reports, vol. 5, No. 7830, 2015, pp. 1-10.

Zegarra-Moro et al., "Disruption of Androgen Receptor Function Inhibits Proliferation of Androgen-refractory Prostate Cancer Cells", Cancer Res., vol. 62, Issue 4, Feb. 2002, pp. 1008-1013.

Zhang et al., "Corticosteroid Co-Treatment Induces Resistance to Chemotherapy in Surgical Resections, Xenografts and Established Cell Lines of Pancreatic Cancer", BMC Cancer, vol. 6, No. 61, Mar. 15, 2006, pp. 1-14.

Zhao et al., "Glucocorticoid Receptor in Prostate Epithelia is not required for Corticosteroid-Induced Epithelial Hyperproliferation in the Mouse Prostate", The Prostate, vol. 74, 2014, pp. 1068-1078.

Zou et al., "Androgen-Induced Coactivator ANCCA Mediates Specific Androgen Receptor Signaling in Prostate Cancer", Cancer Res., vol. 69, Issue 8, Apr. 2009, pp. 3339-3346.

Provisional U.S. Appl. No. 61/317,182, filed Mar. 24, 2010, pp. 1-63.

Neckers et al., "Heat-Shock Protein 90 Inhibitors As Novel Cancer Chemotherapeutic Agents", Expert Opinion on Emerging Drugs, vol. 7, No. 2, Oct. 2002, pp. 277-288.

PCT/US2019/067138, "International Preliminary Report on Patentability", dated Jul. 1, 2021, 6 pages.

\* cited by examiner

Segment I Continuous-Dosing Regimen

Part 1: Dose-Finding

Part 2: Dose-Extension

Abbreviations: Nab-Pac, nab-paclitaxel; PK, pharmacokinetic.

Normalized DUSP1 mRNA counts at baseline and C1D15 in all patients and patient subsets.

Genes with a significant change from baseline in patients who benefited from relacorilant + nab-paclitaxel.

(Dotted Line Indicates an Adjusted p value of 0.05)

METHODS OF TREATING CANCER COMPRISING ADMINISTRATION OF A GLUCOCORTICOID RECEPTOR MODULATOR AND A CANCER CHEMOTHERAPY AGENT

CROSS-REFERENCE TO RELATED APPLICATIONS

This application claims the benefit of, and priority to, U.S. Provisional Patent Application 62/782,120, filed Dec. 19, 2018; U.S. Provisional Patent Application 62/847,772, filed May 14, 2019; and U.S. Provisional Patent Application 62/854,768, filed May 30, 2019, the entire contents of all of which applications is hereby incorporated by reference in their entireties.

BACKGROUND

The glucocorticoid receptor (GR) is a is a nuclear hormone receptor that controls the transcription of multiple genes. The GR is found in most bodily tissues, and plays important roles in the body's response to stress, metabolism, glucose regulation, blood pressure, immune response, muscle and bone health, memory, mood, and other systems and responses. GR action is triggered by binding of glucocorticoids (GC) to GR, forming complex comprising the GR and the GC, leading to activation of the GR, its translocation to the cell nucleus, and interaction of the complex with nuclear genetic material. A GC is a GR agonist, and the binding of a GC to GR activates the GR. In humans and many other mammals, the primary GC is cortisol; however, in rodents, for example, corticosterone plays that role. Other GCs include, for example, dexamethasone, prednisone, hydrocortisone, beclamethasone, and other natural and synthetic compounds. Some transcriptional effects of GCs have been described in healthy patients (Olnes et al., 2016). Some transcriptional effects of mifepristone, a steroidal glucocorticoid and progesterone receptor antagonist, have also been described in breast cancer patients (Maranville et al., 2014). However, the transcriptional effects of a selective nonsteroidal glucocorticoid receptor modulator in patients with other cancers, such as, e.g., pancreatic, ovarian, cervical, vulvar, or other solid tumor types have not been described. Further, a relationship between GR-mediated transcriptional response and tumor progression has not been described.

Cancer patients may be treated surgically to remove, as much as possible, cancerous tissue. Cancer patients may receive medical treatment, such as chemotherapy or radiation treatment. Cancer patients may receive both surgical and medical treatment for cancer.

As noted above, the GR is found in most tissues of the body in normal subjects, and also in solid tumor malignancies (Block et al. Cancer Management Res. 9:65-72 (2017)). It has been proposed that activation of GR in cancer cells may have anti-cancer effect. However, the relationship, if any, to GR expression in cancer, in the response to cancer, and in response to cancer chemotherapy, remains uncertain: see, e.g.: Maranville et al. Gene expression of peripheral blood cells reveals pathways downstream of glucocorticoid receptor antagonism and nab-paclitaxel treatment. *Pharmacogenet Genomics*. September; 24(9):451-8, 2014. Olnes et al. Effects of Systemically Administered Hydrocortisone on the Human Immunome. *Scientific Reports*. 14; 6:23002, 2016. Thus, the role of GR in cancer and in its treatment is unclear.

Accordingly, methods for identifying patients most likely to benefit from treatment, and methods for treating cancer patients so identified, are lacking in the art and are required.

SUMMARY

Novel methods for treating cancer are disclosed. In embodiments, the cancer may comprise a solid tumor. In embodiments, the novel methods for treating cancer include methods of administering a glucocorticoid receptor (GR) modulator (GRM) along with a cancer chemotherapeutic agent, effective to treat cancer. In embodiments, the GRM is a GR antagonist (GRA). In embodiments, the GRM may be a heteroaryl ketone fused azadecalin GRM or an octahydro fused azadecalin GRM. In preferred embodiments, the GRM is relacorilant.

Applicant describes herein the effects of administration of a GRM such as relacorilant on the expression of multiple genes in human subjects, and describes differences in that gene expression between normal subjects and cancer patients. The transcriptional effects of a selective nonsteroidal glucocorticoid receptor modulator in patients with pancreatic, ovarian, cervical, vulvar, or other solid tumor types have not previously been described. It is notable that systemic transcriptional effects on gene expression have not been described for other steroid hormone systems (e.g., androgen receptor (AR) antagonists or estrogen receptor (ER) antagonists). As described below, administration of the AR antagonist enzalutamide does not cause significant effects on gene expression such as those reported here following administration of the GRM relacorilant. Thus, the whole-blood transcriptional effects of GR antagonism disclosed herein were surprising and unexpected. Further, a relationship between GR-mediated transcriptional response and tumor progression previously has not been described. The novel treatment methods disclosed herein utilize these differences in gene expression, and these relationships between GR-mediated transcriptional response and tumor progression, providing improved cancer treatments.

Applicant discloses herein methods for identifying cancer patients likely to benefit from treatments that include GRM administration, and in particular that include relacorilant administration, by measuring transcription of specific genes isolated from blood. Applicant discloses herein that relacorilant administration led to decreases in the expression levels of several genes in cancer patients who derived benefit from combined treatment with a GRM and a cancer chemotherapeutic agent. Similar cancer patients, who received the same combined treatment with a GRM and a cancer chemotherapeutic agent, did not show relacorilant-related decreased gene expression levels, and did not experience benefit from the combined therapy.

Applicant discloses herein that a decrease in gene expression levels, following treatment with a GRM, such as relacorilant, of the following genes are indicative of patients who are likely to benefit from combined treatment with a GRM and a cancer chemotherapeutic agent: APC, CLEC4E, ENTPD1, ICAM3, RELN, BID, CLEC7A, ESYT1, IL10RA, RICTOR, CCL5, COL6A3, F2RL1, IL32, RPL7A, CCR5, COX2, FBP1, IL7R, SELP, CD27, CXCL1, FCGR3A/B, ITGA6, THBD, CD300A, CXCL2, FCGRT, KLRB1, TMEM173, CD3E, CXCR3, GIMAP6, LCK, TNFRSF9, CD3G, CXCR6, GOT2, LDHB, TNKS, CD40LG, EDN1, GZMK, MRE11, TP53, CEACAM3, EIF2B4, ICAM2, MYC, and TREM1. In embodiments, the at least one gene is selected from the group of genes consisting of ICAM3, TREM1, FCGRT, GIMAP6, IL10RA, IL7R, CEACAM3, and COL6A3. In embodiments, the at least one gene is selected from the group of genes consisting of IL32, EDN1, CD3G, CCL5, RICTOR, and BID. In embodiments, the at least one gene is selected from the group of genes consisting of CXCL2, FBP1, CD27, TNKS, CD40LG, CXCR3, LDHB, THBD, TNFRSF9, and RPL7A. In embodiments, the at least one gene is selected from the group of genes consisting of EIF2B4, MRE11, CD3E, GOT2, ICAM2, TP53, CLEC7A, and COX2. In embodiments, the at least one gene is selected from the group of genes consisting of GZMK, CD300A, TMEM173, MYC, ENTPD1, CXCR6, RELN, CXCL1, CLEC4E, CCR5, ITGA6, APC, and F2RL1. In embodiments, the expression levels of at least two of said genes are measured, and wherein said GRM (e.g., relacorilant) and said cancer chemotherapy agent are administered to the patient if the first expression levels of the two genes are greater than the second expression levels of the two genes. In embodiments, the expression levels of at least three genes are measured, and wherein said GRM (e.g., relacorilant) and said cancer chemotherapy agent are administered to the patient if the first expression level of said at least three genes is greater than the first expression level of said at least three genes. In embodiments, the expression levels of at least four, or five, or more genes are measured, and wherein said GRM (e.g., relacorilant) and said cancer chemotherapy agent are administered to the patient if the first expression level of said at least four, or five, or more genes is greater than the first expression level of said at least four, or five, or more genes.

In embodiments, the same GRM is used to identify a patient likely to benefit from combined treatment with a GRM and a cancer chemotherapeutic agent, and is used in the combined GRM and cancer chemotherapeutic agent of that patient. In embodiments, relacorilant is used for identifying a patient for such treatment, and is used in the combined GRM and cancer chemotherapeutic agent of that patient. In embodiments, the cancer chemotherapy agent comprises a taxane, which may be selected from, e.g., paclitaxel, nab-paclitaxel, docetaxel, larotaxel, tesetaxel, cabazitaxel, and ortataxel. In embodiments, the gene expression levels are measured in a blood sample obtained from the patient. In embodiments, the gene expression levels mRNA levels.

Applicant discloses herein that a decrease in gene expression levels, following treatment with a GRM, such as relacorilant, of the following genes are indicative of patients who are likely to benefit from combined treatment with a GRM and a cancer chemotherapeutic agent: COX2; DUSP1; GSK3b; MCL-1; PIK3CG; RGS-2; SGK1; and STAT3. Applicant further discloses herein that a decrease in gene expression levels of GSK3b or MCL-1, or both; or in COX2 and DUSP1, or both; or in any two, or three, or all four of GSK3b, MCL-1, COX2, and DUSP1, in a patient following treatment with a GRM such as relacorilant is indicative that the patient is likely to benefit from combined treatment with a GRM (e.g., relacorilant) and a cancer chemotherapeutic agent. Applicant further discloses herein that patients in whom gene expression levels of these genes does not decrease, following treatment with a GRM (e.g., relacorilant), are likely not to benefit from such combined treatment with a GRM and a cancer chemotherapeutic agent. In embodiments, the gene expression levels are mRNA expression levels.

The methods disclosed herein are useful to treat cancer patients likely to benefit from cancer chemotherapy combined with administration of a GRM (e.g., relacorilant) to the cancer patient. In preferred embodiments, the GRM of the present methods is relacorilant. The methods are useful to identify cancer patients likely to benefit from cancer chemotherapy combined with administration of a GRM. The methods include: administering a GRM (e.g., relacorilant) to a patient, and determining whether or not the expression level of a gene is decreased in comparison with baseline expression levels of the gene measured in the patient prior to the GRM administration. The treatment methods include: administering a GRM (e.g., relacorilant) to a patient, determining whether or not the expression level of a gene is decreased in comparison with baseline expression levels of the gene measured in the patient prior to the GRM administration, and treating the patient with a combination of a GRM and a cancer chemotherapy agent. In embodiments of the treatment methods, the GRM of the combination of a GRM and a cancer chemotherapy agent is relacorilant. The methods further include identifying a patient in whom the expression level of a gene is decreased in comparison with corresponding gene baseline levels as a patient likely to benefit from chemotherapy combined with administration of a GRM. The methods further include administering cancer chemotherapy and a GRM to a patient identified by such methods as a patient likely to benefit from cancer chemotherapy combined with administration of a GRM, whereby the cancer is treated in the patient. In embodiments, the cancer chemotherapy comprises administration of a taxane, and the methods further include administering taxane cancer chemotherapy in conjunction with GRM administration to a patient identified by such methods as a patient likely to benefit from cancer chemotherapy combined with administration of a GRM. In embodiments, the taxane is selected paclitaxel, nab-paclitaxel, docetaxel, larotaxel, tesetaxel, cabazitaxel, and ortataxel.

In embodiments, the gene expression level is a mRNA level measured from a blood sample taken from the patient. In embodiments, the gene for which the expression level is measured is a gene selected from COX2, DUSP1, GSK3b, MCL-1, PIK3CG, RGS-2, SGK1, and STAT3. In some preferred embodiments, the gene for which the expression level is measured is GSK3b, or MCL-1, or both GSK3b and MCL-1. In some preferred embodiments, the gene for which the expression level is measured is COX2, or DUSP1, or both COX2 and DUSP1. In embodiments, the level of expression of the gene prior to administration of a GRM is compared to the level of expression of the gene following administration of the GRM, and, a patient whose gene expression level decreases following administration of the GRM is identified as a patient likely to benefit from administration of a GRM and a cancer therapeutic agent. In embodiments where the level of expression of the gene is not decreased after GRM administration as compared to the level of expression of the gene prior to administration of the GRM, the patient is identified as a patient not likely to benefit from administration of a GRM and a cancer therapeutic agent.

In embodiments, the expression levels of two, or three, or four, or five, or more genes are measured from a blood sample taken from the patient. In embodiments, the mRNA levels of two, three, four, five, or more genes are measured from a blood sample taken from the patient. In embodiments, the genes for which the expression levels of two, or three, or four, or five, or more genes are measured are genes selected from COX2, DUSP1, GSK3b, MCL-1, PIK3CG, RGS-2, SGK1, and STAT3. In preferred embodiments, the genes for which the expression levels of two genes are measured are GSK3b and MCL-1. In preferred embodiments, the genes for which the expression levels of three genes are measured include GSK3b and MCL-1. In preferred embodiments, the genes for which the expression levels of four, five, or more genes are measured include GSK3b and MCL-1. In preferred embodiments, the genes for which the expression levels of two genes are measured are COX2 and DUSP1. In preferred embodiments, the genes for which the expression levels of three genes are measured include COX2 and DUSP1. In preferred embodiments, the genes for which the expression levels of four, five, or more genes are measured include COX2 and DUSP1.

In embodiments, the levels of expression of each of the two, or three, or four, or five, or more genes prior to administration of a GRM is compared to the levels of expression of these genes following administration of the GRM, and, a patient whose gene expression levels decrease following administration of the GRM is identified as a patient likely to benefit from administration of a GRM and a cancer therapeutic agent. In embodiments where the level of expression of any one of the two, or three, or four, or five, or more genes is decreased after GRM administration as compared to the level of expression of that gene prior to administration of the GRM, the patient is identified as a patient likely to benefit from administration of a GRM and a cancer therapeutic agent. In embodiments where the levels of expression of some of the two, or three, or four, or five, or more genes is decreased after GRM administration as compared to the levels of expression of these genes prior to administration of the GRM, the patient is identified as a patient likely to benefit from administration of a GRM and a cancer therapeutic agent. In embodiments where the levels of expression of each of the two, or three, or four, or five, or more genes is decreased after GRM administration as compared to the levels of expression of these genes prior to administration of the GRM, the patient is identified as a patient likely to benefit from administration of a GRM and a cancer therapeutic agent. The methods further include administering cancer chemotherapy and a GRM to a patient identified by such methods, e.g., identifying a patient as likely to benefit from such treatments where the levels of expression of each of the two, or three, or four, or five, or more genes is decreased after GRM administration as compared to the levels of expression of these genes prior to administration of the GRM, whereby the cancer is treated in the patient. In embodiments where the levels of expression of none of these genes is decreased after GRM administration as compared to the levels of expression of these genes prior to administration of the GRM, the patient is identified as a patient not likely to benefit from administration of a GRM and a cancer therapeutic agent.

In embodiments, the GRM is a glucocorticoid receptor antagonist (GRA). In embodiments of the methods disclosed herein, the GRM is a non-steroidal GRM, and may be a heteroaryl ketone fused azadecalin GRM, and may be an octahydro fused azadecalin GRM. In embodiments of the methods disclosed herein, the GRM is relacorilant.

By identifying patients likely to benefit from cancer chemotherapy combined with GRM administration, administration of cancer treatment is improved and treatment outcomes are improved, by a) providing appropriate chemotherapy, including cancer chemotherapy combined with GRM administration, to patients likely to derive benefit from that therapy, and b) avoiding administering unnecessary or inappropriate therapy to patients unlikely to derive benefit therefrom, thus allowing or directing those patients to receive alternative therapy better adapted to their clinical situation. The present methods provide methods for treating cancer patients with cancer chemotherapy combined with GRM administration, determined to be a therapy from which the patient is likely to derive benefit, thereby improving cancer treatment improving cancer treatment outcomes.

The methods disclosed herein provide improved treatment regimens for cancer patients, the regimens comprising administration of a cancer chemotherapy agent and GRM. The methods disclosed herein also provide improved methods for identifying cancer patients likely to benefit from treatments comprising a cancer chemotherapy agent and GRM. Identifying patients likely to respond to a specific therapy improves treatment, improves the efficiency of clinical trials, and avoids unnecessary exposure of patients to non-beneficial therapies.

Other objects, features, and advantages of the methods disclosed herein will be apparent to one of skill in the art from the following detailed description and figures.

DESCRIPTION OF THE FIGURES

FIG. 7A shows that transcriptional effects of relacorilant+nab-paclitaxel (Abx) are pronounced in patients with SD, PR, or CR vs PD. Genes expression in patients with progressive disease (PD) are indicated by squares. Genes expression in patients with stable disease (SD), partial response (PR), or complete response (CR) are indicated by circles. The transcriptional changes (mRNA measurements) in whole blood from baseline to C1D15 were compared between patients and separated by best overall response. Inset details genes downregulated in SD/PR/CR (92 genes) vs PD (30 genes) patients. Dotted line represents an adjusted p-value of 0.05 (markers above that line have adjusted p<0.05).

FIG. 7B shows that no significant transcriptional effects of enzalutamide were observed after 28 days of enzalutamide administration. The small circular markers indicate the change in gene expression for individual genes. None of the gene expression levels changes following enzalutamide (as compared to baseline levels) reach significance (all adjusted p-values are greater than 0.5).

FIG. 10B shows the fraction of xenograft tumors (as %) whose volume remained below 400 mm$^3$ on the days indicated along the horizontal axis. Tumor-bearing mice were treated with vehicle, relacorilant (30 mg/kg every day), paclitaxel (three doses of 7.5 mg/kg paclitaxel, one dose administered on each of the days indicated in FIG. 10A), and the combination relacorilant (30 mg/kg every day) with paclitaxel (7.5 mg/kg doses of paclitaxel each administered on days 8, 12, and 16 post implantation). The tumor sizes in mice administered vehicle (DMSO) are indicated by the darkest line (extreme left); in mice daily administered 300 nM relacorilant by the lighter gray line, nearly superimposed on the vehicle line at left; in mice administered paclitaxel (7.5 mg/kg paclitaxel dosed on days 8, 12, and 16 after tumor implantation) are indicated by the dark gray line between the other lines; and in mice administered daily 300 nM relacorilant and the same three doses of paclitaxel (right-most light gray line). Addition of 300 nM relacorilant to the paclitaxel doses delayed the time to progression (p<0.0001) compared to paclitaxel alone (right-most light gray line).

DETAILED DESCRIPTION

I. Introduction

Figure 1:
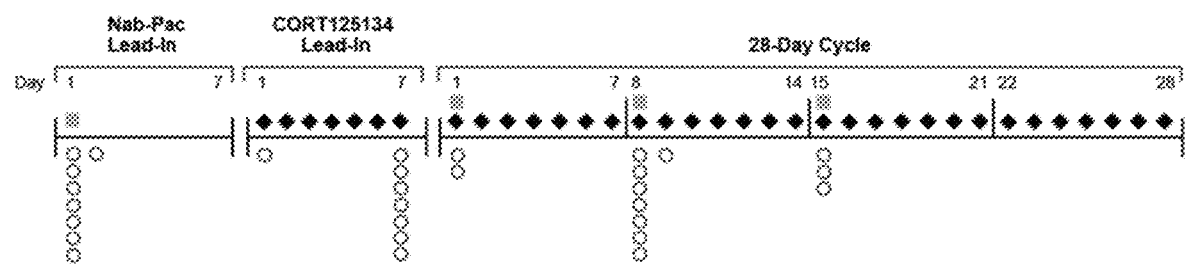
FIG. 1: Segment I Continuous-Dosing Regimen
Figure 1:
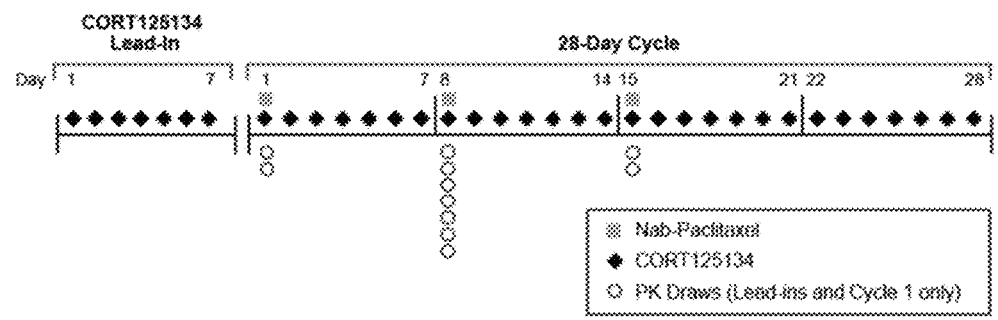

Provided herein are methods for treating a cancer patient by methods comprising combined administration of a glucocorticoid receptor (GR) modulator (GRM) and a cancer chemotherapeutic agent. In embodiments, the GRM is a GR antagonist (GRA). In embodiments, the methods include identifying cancer patients likely to benefit from combined administration of a GRM and a cancer chemotherapeutic agent, and administering a GRM and a cancer chemotherapeutic agent to the patient. Identification of cancer patients likely to benefit from such combined administration of a GRM and a cancer chemotherapeutic agent includes determining gene expression levels in the cancer patient following administration of a GRM to the cancer patient. In embodiments, the GRM administered to the patient in combination with a cancer chemotherapeutic agent is the same GRM as was used to determine gene expression levels in the cancer patient.

Accordingly, Applicant discloses herein methods of treating cancer in a patient suffering from cancer, the methods comprising: Measuring a first expression level of a gene in a sample obtained from said patient; Administering an effective amount of a glucocorticoid receptor modulator (GRM) to said patient; then Measuring a second expression level of a gene in a sample obtained from said patient; and Administering a GRM and a cancer chemotherapy agent to the patient if the second expression level is less than said first expression level, Whereby said cancer is treated. In embodiments, the measured gene expression levels are mRNA levels. In embodiments, the measured genes include genes selected from COX2, DUSP1, GSK3b, MCL-1, PIK3CG, RGS-2, SGK1, and STAT3. In some preferred embodiments, the genes for which the gene expression levels are measured include GSK3b and MCL-1. In some preferred embodiments, the genes for which the gene expression levels are measured include COX2 and DUSP. In preferred embodiments, the GRM is relacorilant.

Applicant further discloses herein methods of identifying a cancer patient likely to benefit from combined administration of a glucocorticoid receptor modulator (GRM) and a cancer chemotherapy agent, the method comprising: Measuring a first expression level of a gene in a sample obtained from said patient; Administering an effective amount of a glucocorticoid receptor modulator (GRM) to said patient; then Measuring a second expression level of a gene in a sample obtained from said patient; and Identifying the patient as likely to benefit from combined administration of a GRM and a cancer chemotherapy agent if the second expression level is less than said first expression level, Whereby said patient likely to benefit from combined administration of a GRM and a cancer chemotherapy agent is identified. In embodiments, the measured gene expression levels are mRNA levels. In embodiments, the measured genes include genes selected from COX2, DUSP1, GSK3b, MCL-1, PIK3CG, RGS-2, SGK1, and STAT3. In some preferred embodiments, the genes for which the gene expression levels are measured include GSK3b and MCL-1. In some preferred embodiments, the genes for which the gene expression levels are measured include COX2 and DUSP-1. In preferred embodiments, the GRM is relacorilant.

In embodiments of the methods disclosed herein, said expression levels of said gene are measured in a blood sample obtained from the patient. In embodiments of the methods disclosed herein, the gene expression levels of are mRNA levels. In embodiments of the methods disclosed herein, the gene expression levels are mRNA levels measured in a blood sample obtained from the patient. In embodiments of the methods disclosed herein, the gene is selected from the group of genes consisting of COX2, DUSP1, GSK3b, MCL-1, PIK3CG, RGS-2, SGK1, and STAT3. In embodiments of the methods disclosed herein, the gene may be selected from the group of genes consisting of COX2, DUSP1, GSK3b, and MCL-1. In preferred embodiments, the genes for which the gene expression levels are measured include GSK3b and MCL-1.

In embodiments of the methods disclosed herein, at least two gene expression levels are measured in a sample obtained from a patient; the sample may be a blood sample, and the gene expression levels may be mRNA levels. In preferred embodiments of the methods in which expression of at least two genes is measured, the genes include GSK3b and MCL-1. In embodiments of the methods disclosed herein, at least three, or at least four, or at least five, or at least six, or at least seven, or at least eight gene expression levels are measured in a sample obtained from a patient; the sample may be a blood sample, and the gene expression levels may be mRNA levels.

Accordingly, Applicant discloses herein methods of treating cancer in a patient suffering from cancer, the methods comprising: Measuring a first expression level of each of two or more genes in a sample obtained from said patient; Administering an effective amount of a glucocorticoid receptor modulator (GRM) to said patient; then Measuring a second expression level of each of said two or more genes in a sample obtained from said patient; and Administering a GRM and a cancer chemotherapy agent to the patient if, for at least one of said two or more genes, the second expression level is less than said first expression level, Whereby said cancer is treated. In embodiments, a GRM and a cancer chemotherapy agent is administered to the patient if, for each of said two or more genes, the second expression level is less than said first expression level, Whereby said cancer is treated. In embodiments, a GRM and a cancer chemotherapy agent is administered to the patient if, where three or more gene expression levels are measured, for the majority of the three or more genes, the second expression level is less than said first expression level, Whereby said cancer is treated. In embodiments, the genes may be selected from the group of genes consisting of COX2, DUSP1, GSK3b, and MCL-1. In preferred embodiments, the genes for which the gene expression levels are measured include GSK3b and MCL-1. In preferred embodiments, the GRM is relacorilant.

Accordingly, Applicant discloses herein methods of identifying a cancer patient likely to benefit from combined administration of a glucocorticoid receptor modulator (GRM) and a cancer chemotherapy agent, the methods comprising: Measuring a first expression level of each of two or more genes in a sample obtained from said patient; Administering an effective amount of a glucocorticoid receptor modulator (GRM) to said patient; then Measuring a second expression level of each of said two or more genes in a sample obtained from said patient; and Identifying the patient as likely to benefit from combined administration of a GRM and a cancer chemotherapy agent if, for at least one of said two or more genes, the second expression level is less than said first expression level, Whereby said patient likely to benefit from combined administration of a GRM and a cancer chemotherapy agent is identified. In embodiments, a patient likely to benefit from combined administration of a GRM and a cancer chemotherapy agent is identified if, for each of said two or more genes, the second expression level is less than said first expression level. In embodiments, a patient likely to benefit from combined administration of a GRM and a cancer chemotherapy agent is identified if, where three or more gene expression levels are measured, for the majority of the three or more genes, the second expression level is less than said first expression level.

In embodiments of the methods disclosed herein, where more than one gene expression level is measured, the genes are selected from the group of genes consisting of COX2, DUSP1, GSK3b, MCL-1, PIK3CG, RGS-2, SGK1, and STAT3. In embodiments of the methods disclosed herein, where more than one gene expression level is measured, the genes may be selected from the group of genes consisting of COX2, DUSP1, GSK3b, MCL-1, PIK3CG, RGS-2, SGK1, and STAT3. In embodiments of the methods disclosed herein, at least two genes are selected from the group of genes consisting of COX2, DUSP1, MCL-1, and GSK3b. In preferred embodiments, the genes for which the gene expression levels are measured include GSK3b and MCL-1. In preferred embodiments, the GRM is relacorilant.

In embodiments, gene expression levels are quantified by polymerase chain reaction. In embodiments, gene expression levels are quantified by sequencing techniques, by use of microarrays, by NanoString technology, or by a comparable technology known in the art. In embodiments, gene expression levels are determined by identifying and measuring the amounts of the protein or amino acid sequences encoded by mRNA in the blood sample.

In embodiments, an average or weighted average of gene levels is calculated based on the levels of multiple genes. For example, in embodiments, an average or weighted average of gene levels is calculated based on the levels of multiple genes selected from COX2, DUSP1, GSK3b, MCL-1, PIK3CG, RGS-2, SGK1, and STAT3. In other embodiments, an average or weighted average of gene levels is calculated based on the levels of multiple genes selected from COX2, DUSP1, MCL-1, and GSK3b. In preferred embodiments, the genes for which the gene expression levels are measured include GSK3b and MCL-1.

In embodiments of the methods disclosed herein, the cancer comprises a solid tumor. In embodiments, the cancer comprises a metastatic tumor. In embodiments, the cancer comprises a cancer selected from the group of cancers consisting of cancer of the bone, breast, prostate, ovary, skin, brain, bladder, cervix, liver, pancreas, lung, colon, stomach, intestine, adrenal gland, kidney, blood, or other organ or tissue.

In embodiments of the methods disclosed herein, the cancer chemotherapy agent comprises a taxane. In embodiments, the cancer chemotherapy agent comprises a taxane selected from paclitaxel, nab-paclitaxel, docetaxel, larotaxel, tesetaxel, cabazitaxel, and ortataxel. In embodiments, the cancer chemotherapy agent comprises paclitaxel. In embodiments, the cancer chemotherapy agent comprises nab-paclitaxel.

In embodiments of the methods disclosed herein, the cancer chemotherapy agent is administered to the patient at least once per month. In embodiments, administration of said cancer chemotherapy agent comprises administration of said cancer chemotherapy agent according to a 28-day cycle of administration. In embodiments, administration of said cancer chemotherapy agent comprises administration of said cancer chemotherapy agent at least twice per month. In embodiments, administration of said cancer chemotherapy agent at least three times per month.

In embodiments, the GRM is a non-steroidal compound, and may be administered orally to the patient. In embodiments, the GRM administration comprises administration of said GRM at least once per week. In embodiments, the GRM administration comprises administration of said GRM at least twice per week. In embodiments, the GRM administration comprises administration of said GRM at least three times per week. In embodiments, the GRM doses are selected from 10 milligrams (mg) to about 1000 mg. In embodiments, the GRM is administered once every other day, or once every third day. In embodiments, the GRM dose is a daily dose. In embodiments, the GRM is administered twice per day, or is administered three times per day. In embodiments, the GRM dose is administered once per day (i.e., is a once-daily dose). In embodiments, the GRM is administered once per day at about the same time of day each day. In embodiments, the GRM is administered with food. In embodiments, the GRM is administered to a patient without food. In embodiments, the GRM is administered without food in the morning to a patient prior to the patient's morning meal.

In embodiments of the methods disclosed herein, the glucocorticoid receptor modulator (GRM) is a glucocorticoid receptor antagonist (GRA); and may be a non-steroidal GRM. In embodiments, the GRM is a non-steroidal GRM having a backbone structure selected from a cyclohexylpyrimidine backbone, a fused azadecalin backbone, a heteroaryl ketone fused azadecalin backbone, and an octahydro fused azadecalin backbone. In embodiments, the GRM is a heteroaryl ketone fused azadecalin GRM.

In preferred embodiments, the GRM is relacorilant: (R)-(1-(4-fluorophenyl)-6-((1-methyl-1H-pyrazol-4-yl)sulfonyl)-4,4a, 5,6,7,8-hexahydro-1H-pyrazolo[3,4-g]isoquinolin-4a-yl)(4-(trifluoromethyl)pyridin-2-yl)methanone (also termed "CORT125134"), which has the following structure:

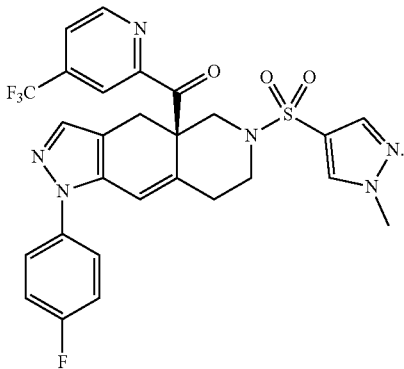 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

II. Definitions

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "tumor" and "cancerous tumor" as used herein refer to, masses of abnormal tissue; such abnormal tissue comprises neoplasmic tissue (i.e., tumor, as used herein, refers to a neoplasm). Unless explicitly termed "non-cancerous", the term "tumor" as used herein refers to a cancerous tumor. Tumors include, but are not limited to, carcinoma, adenocarcinoma, adenoma, neuroendocrine, neuroepithelial, neuroblastoma, glioblastoma, and other cancerous masses of any form or origin. A tumor may be of any size, including, e.g., measuring less than about 5 millimeters (mm) in diameter, or measuring less than about 10 millimeters (mm) in diameter, or measuring greater than about 10 mm in diameter but less than about 1 centimeter (cm) in diameter, or measuring greater than about 10 mm in diameter but less than about 2 centimeters (cm) in diameter, or measuring greater than about 2 cm in diameter. A tumor may be a primary tumor (e.g., a tumor which remains in the general location in which it originated in the body), and may be a metastatic tumor (e.g., a tumor which grew from cancerous cells or tissues that have migrated from a different location in the body). A tumor may be, for example, a tumor of the bone, breast, prostate, ovary, skin, brain, bladder, cervix, liver, pancreas, lung, colon, stomach, intestine, adrenal gland, kidney, blood, or other organ or tissue. A tumor, such as a metastatic tumor, or cells that lead to a metastatic tumor, may be a blood-borne.

The term "solid tumor" as used herein refers to a cancerous tumor in which cancerous cells adhere to each other, to form a continuous, or at least partially continuous, tissue comprising cancerous cells. A solid tumor may also include pre-cancerous cells and tissue, and may also include non-cancerous cells and tissue. A solid tumor may include fluid, including fluid-filled spaces or cavities.

"Patient," "individual" or "subject" is used interchangeably to refer to a human subject. In some cases, the individual is suspected of having adrenal insufficiency.

As used herein, the terms "did not experience benefit", "patients experiencing no benefit", and "patients not experiencing benefit" refer to cancer patients suffering from progressive disease, i.e., whose tumors progress in size, or metastasize, or otherwise progress during the study period.

The term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, epicutaneous, subcutaneous, intraperitoneal, intraventricular, and intracranial. Other modes of delivery include, but are not limited to, the use of liposomal formulations, intravenous infusion, transdermal patches, etc.

The term "sample" refers to a biological sample obtained from a human subject. Such samples are typically removed from the subject, and, when obtained, become entirely separate from the subject (i.e., are in vitro samples). The sample can be any cell, tissue or fluid sample obtained from a human subject. The sample may be, e.g., a blood sample, a saliva sample, a urine sample, or other sample obtained from the patient. Samples can be subject to various treatment, storage or processing procedures before being analyzed according to the methods described herein. Generally, the terms "sample" or "samples" are not intended to be limited by their source, origin, manner of procurement, treatment, processing, storage or analysis, or any modification. Thus, in embodiments, samples are in vitro samples and may be analyzed using in vitro methods. The methods disclosed herein are in vitro methods when used with samples obtained from, and removed from, the human subject.

The term "glucocorticoid" ("GC") includes any compound known in the art that is referred to as a glucocorticoid receptor agonist, glucocorticoid, glucocorticosteroid, corticoid, corticosteroid, or steroid that binds to and activates a glucocorticoid receptor. "Glucocorticosteroid" refers to a steroid hormone or steroidal molecule that binds to the glucocorticoid receptor. Glucocorticosteroids are GCs. Glucocorticosteroids are typically characterized by having 21 carbon atoms, an α,β-unsaturated ketone in ring A, and an α-ketol group attached to ring D. They differ in the extent of oxygenation or hydroxylation at C-11, C-17 and C-19 (Rawn, "Biosynthesis and Transport of Membrane Lipids and Formation of Cholesterol Derivatives," in Biochemistry, Daisy et al. (eds.), 1989, pg. 567). GCs include, for example, dexamethasone, prednisone, prednisolone, triamcinolone, and hydroxycortisone.

"Glucocorticoid receptor" ("GR") refers to the type II GR which specifically binds to cortisol and/or cortisol analogs such as dexamethasone (See, e.g., Turner & Muller, *J Mol Endocrinol*, 2005 35 283-292). The GR is also referred to as the cortisol receptor. The term includes isoforms of GR, recombinant GR and mutated GR. Inhibition constants ($K_i$) against the human GR receptor type II (Genbank: P04150) are between 0.0001 nM to 1,000 nM; preferably between 0.0005 nM to 10 nM, and most preferably between 0.001 nM to 1 nM.

The term "glucocorticoid receptor modulator" or "GRM" refers to a composition or compound which binds to GR and changes ("modulates") the binding of a GC to GR, or modulates the effects of such GR binding. GCs (GR agonists) include cortisol and cortisol analogs, synthetic or natural, as discussed above. Thus, a GRM alters the effect of GR agonist binding that would occur in the absence of the GRM.

The term "glucocorticoid receptor antagonist" or "GRA" refers to any composition or compound which partially or completely inhibits (antagonizes) the binding of a glucocorticoid receptor (GR) agonist, such as cortisol, or cortisol analogs, synthetic or natural, to a GR. A GRA is a GRM which provides antagonistic modulation of the effect of GR agonist binding that would occur in the absence of the GRA. A "specific glucocorticoid receptor antagonist" refers to any composition or compound which inhibits any biological response associated with the binding of a GR to an agonist. By "specific," the drug preferentially binds to the GR rather than other nuclear receptors, such as mineralocorticoid receptor (MR), androgen receptor (AR), or progesterone receptor (PR). It is preferred that the specific glucocorticoid receptor antagonist bind GR with an affinity that is 10× greater ($1/10^{th}$ the $K_d$ value) than its affinity to the MR, AR, or PR, both the MR and PR, both the MR and AR, both the AR and PR, or to the MR, AR, and PR. In a more preferred embodiment, the specific glucocorticoid receptor antagonist binds GR with an affinity that is 100× greater ($1/100^{th}$ the $K_d$ value) than its affinity to the MR, AR, or PR, both the MR and PR, both the MR and AR, both the AR and PR, or to the MR, AR, and PR.

Non-steroidal GRM compounds include glucocorticoid receptor antagonists having a heteroaryl ketone fused azadecalin backbone, or an octahydro fused azadecalin backbone. Exemplary GRMs having a heteroaryl ketone fused azadecalin backbone include those described in U.S. Pat. Nos. 8,859,774; 9,273,047; 9,707,223; and 9,956,216. Exemplary GRMs having an octohydro fused azadecalin backbone include those described in U.S. Pat. No. 10,047,082.

All patents, patent applications, patent publications, and published articles cited herein, both supra and infra, are hereby incorporated by reference in their entireties, including all compounds and compositions disclosed in the patents, patent applications, patent publications, and published articles cited herein.

As used herein, the term "relacorilant" (also known as CORT125134) refers to the heteroaryl ketone fused azadecalin compound (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone (Example 18 of U.S. Pat. No. 8,859,774), which has the following structure:

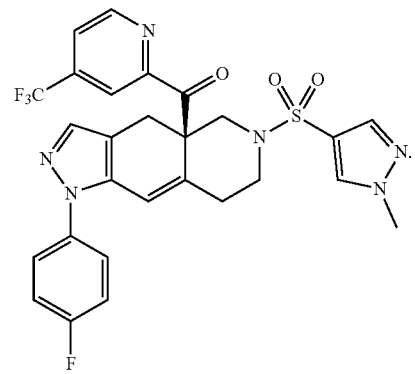 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

As used herein, the term "CORT122928" refers to the heteroaryl ketone fused azadecalin compound (R)-(1-(4-fluorophenyl)-6-((4-(trifluoromethyl)phenyl)sulfonyl)-4,4a,5,6,-7,8-hexahydro-1H-pyrazolo[3,4-g]isoquinolin-4a-yl)(thiazol-2-yl)methanone (Example 1C of U.S. Pat. No. 8,859,774), which has the following structure:

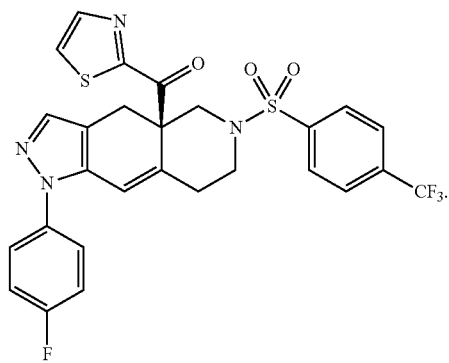 [SMILES: O=C(c1nccs1)[C@]12Cc3cnn(-c4ccc(F)cc4)c3C=C1CCN(S(=O)(=O)c1ccc(C(F)(F)F)cc1)C2]

As used herein, the term "CORT113176" refers to the heteroaryl ketone fused azadecalin compound (R)-(1-(4-fluorophenyl)-6-((4-(trifluoromethyl)phenyl) sulfonyl)-4,4a,5,6,7,8-hexahydro-1-H-pyrazolo P,4-g]isoquinolin-4a-yl) (pyridin-2-yl)methanone (Example 1 of U.S. Pat. No. 8,859,774) which has the following structure:

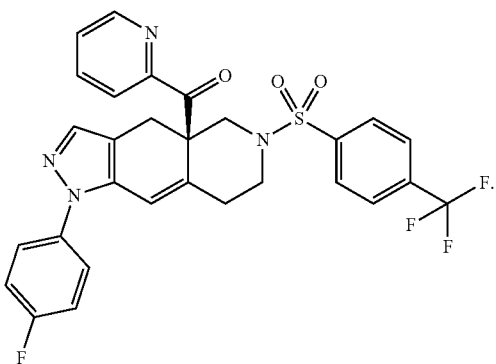 [SMILES: O=C(c1ccccn1)[C@]12Cc3cnn(-c4ccc(F)cc4)c3C=C1CCN(S(=O)(=O)c1ccc(C(F)(F)F)cc1)C2]

As used herein, the term "CORT125281" refers to the octahydro fused azadecalin compound ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone (Example 2C of U.S. Pat. No. 10,047,082), which has the structure:

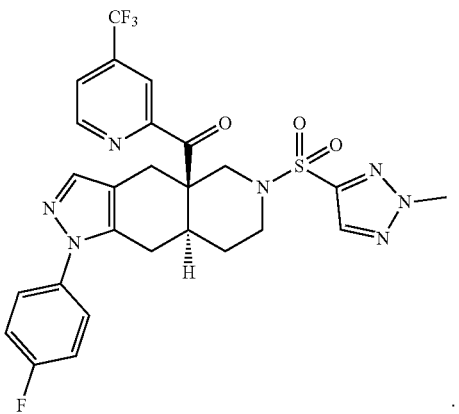 [SMILES: Cn1ncc(S(=O)(=O)N2CC[C@H]3Cc4c(cnn4-c4ccc(F)cc4)C[C@]3(C(=O)c3cc(C(F)(F)F)ccn3)C2)n1]

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

In addition to, or along with, the methods disclosed herein, cancers may be treated with cancer chemotherapeutic agents. As used herein, the terms "cancer chemotherapeutic", "cancer chemotherapeutic agent", "cancer therapeutic", and "cancer chemotherapy agent" refer to compounds and compositions used to treat cancer. Cancer chemotherapeutic agents and treatments by such agents include hormones and hormone modifiers used in "anti-hormonal" cancer treatments, antibody treatments, chemotoxic compounds and formulations that are typically toxic to cancer cells (and often non-cancerous cells as well), antiproliferative agents (reducing cancer cell growth or replication), agents that are anti-metastatic (reducing metastases), and other agents and treatments that inhibit, stop, or reverse the growth or spread of cancer in a cancer patient.

Cancer chemotherapeutic agents include, but are not limited to, doxorubicin, vincristine, cyclophosphamide, fluorouracil (e.g., 5-fluorouracil (5-FU)), topotecan, interferons, platinum derivatives, taxanes (e.g., paclitaxel, nab-paclitaxel, docetaxel, larotaxel, tesetaxel, cabazitaxel, and ortataxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, trimetrexate, metoprine, cyclosporine, daunorubicin, teniposide, amphotericin, alkylating agents (e.g., chlorambucil), 5-fluorouracil, camptothecin, cisplatin, metronidazole, and imatinib mesylate, among others.

As used herein, an "antiproliferative agent" is a compound or composition used to reduce the growth or spread of cancer in a patient. As used herein, antiproliferative agents are cancer chemotherapeutic agents. Antiproliferative agents typically slow or arrest the growth or replication of cancer cells. Chemotherapeutic or antiproliferative agents may also include biologic agents such as, e.g., bevacizumab, panitumumab, pertuzumab, lapatinib.

Chemotherapeutic agents as defined herein include "anti-hormonal agents" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors include anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; luteinizing hormone-releasing hormone agonists, including leuprolide (LUPRON® and ELIGARD®), goserelin, buserelin, and triptorelin; sex steroids, including progestins such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; anti-androgens such as, e.g., enzalutamide, darolutamide, and apalutamide; and pharmaceutically acceptable salts, acids or derivatives of any of the above; as well as combinations of two or more of the above.

Cancer chemotherapeutic agents, such as antiproliferative agents and chemotoxic compounds and formulations include, e.g., abarelix, aldesleukin, alemtuzumab, alitretinoin, allopurinol, altretamine, amifostine, anastrozole, arsenic trioxide, asparaginase, azacitidine, BCG live, bevacuzimab, fluorouracil, bexarotene, bleomycin, bortezomib, busulfan, calusterone, capecitabine, camptothecin, carboplatin, carmustine, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, erlotinib, enzalutamide, estramustine, etoposide phosphate, etoposide, exemestane, filgrastim, floxuridine, fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, and zoledronic acid.

The terms "cancer chemotherapeutic" and "cancer chemotherapeutic agent", "cancer therapeutic", and "cancer chemotherapy agent" thus include chemical compounds useful in the treatment of cancer. Examples of cancer chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethyl enethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin γ1I and calicheamicin Ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), "Abx", albumin-engineered nanoparticle formulations of paclitaxel also known as nab-paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

As used herein, the terms "cancer chemotherapeutic" and "cancer chemotherapy agent" also include (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene 4-hydroxytamoxifen, trioxifene, keoxifene, LY117018, onapristone, and FARESTON® (toremifene citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) antiandrogens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

As used herein, the terms "cancer chemotherapeutic" and "cancer chemotherapy agent" also include antibodies such as alemtuzumab (Campath), bevacizumab (AVASTIN®), Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/1695, Wyeth Research and Abbott Laboratories) which is a recombinant exclusively human-sequence, full-length $IgG_1$ λ antibody genetically modified to recognize interleukin-12 p40 protein.

As used herein, the terms "cancer chemotherapeutic" and "cancer chemotherapy agent" also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quin-azolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoli-ne, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol)-; (R)-6-(4-hydroxyphenyl)-4-[(1-phenylethyl)amino]-7H-pyrrolo[2,3-d]pyrimi-dine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(-dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl) ethyl]amino]methyl]-2-furanyl]-4-quinazolinamine).

As used herein, the terms "cancer chemotherapeutic" and "cancer chemotherapy agent" also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from GlaxoSmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

The terms "cancer chemotherapeutic" and "cancer chemotherapy agent" also include interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

The terms "cancer chemotherapeutic" and "cancer chemotherapy agent" also include immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu); miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Methods of measuring gene expression levels are known in the art. For example, gene expression levels may be measured using polymerase chain reaction methods (PCR), including real-time PCR, quantitative PCR (qPCR), reverse-transcription PCR (RT-PCR), and other PCR methods; by sequencing techniques, by use of microarrays, by NanoString technology (e.g., NanoString XT expression assay (Nanostring Technologies, Seattle Wash., USA), or by a comparable technology known in the art; see, e.g., *Molecular Cloning: A Laboratory Manual* (written by Green and Sambrook, published by Cold Spring Harbor Laboratory, 2012); *DNA MicroArrays: A Molecular Cloning Manual*, by Bowtell and Sambrook, published by Cold Spring Harbor Laboratory, 2003); Shalon, et al., "A DNA microarray system for analyzing complex DNA samples using two-color fluorescent probe hybridization". Genome Res. 6 (7): 639-645 (1996); Pollack et al., "Genome-wide analysis of DNA copy-number changes using cDNA microarrays". Nat Genet. 23 (1): 41-46 (1999). In addition, gene expression levels may be determined by identifying and measuring amounts of the protein or amino acid sequences encoded by mRNA in the blood sample. See, e.g., *Proteins and Proteomics*, by Simpson, Cold Spring Harbor Laboratories, 2003; *Proteomics in Practice*, by Westheimer, Naven, and Hopker, Wiley-Blackwell, 2008.

As used herein, the terms "experienced benefit" and "patients experiencing benefit" refer to cancer patients who exhibit stable disease (SD), or exhibit a partial response (PR), or exhibit a complete response (CR), during or pursuant to the treatment. Stable disease refers to those patients whose tumors do not grow, and do not exhibit metastases, during the study period, although the tumor does not shrink in size. A patient in remission has stable disease. A partial response is seen in those patients whose tumors shrink, during the study period, although the tumor does not disappear. A complete response refers to those patients whose tumors shrink to such a size as to become negligible, or no longer palpable or visible under standard examination.

Methods of Treatment and Differential Diagnosis
Glucocorticoid Receptor Antagonists The methods of the present invention generally provide administering a glucocorticoid receptor modulator (GRM), which may be a glucocorticoid receptor antagonist (GRA).

In embodiments, the GRM has a heteroaryl ketone fused azadecalin backbone or has an octohydro fused azadecalin backbone. Exemplary GRMs having a heteroaryl ketone fused azadecalin backbone include those described in U.S. Pat. No. 8,859,774. Exemplary GRMs having an octohydro fused azadecalin backbone include those described in U.S. Pat. No. 10,047,082, entitled Octahydro Fused Azadecalin Glucocorticoid Receptor Modulators. In embodiments, the GRM is selected from relacorilant (also known as CORT125134), CORT122928, CORT113176, and CORT125281. In preferred embodiments, the GRM is relacorilant.

Pharmaceutical Compositions of Glucocorticoid Receptor Modulators

The GRM administered in the practice of the methods disclosed herein can be prepared in any suitable form, including in a wide variety of oral, parenteral and topical dosage forms. Oral preparations of either include tablets, pills, powder, dragees, capsules, liquids, lozenges, cachets, gels, syrups, slurries, suspensions, etc., suitable for ingestion by the patient. The GRM compositions of the present invention can also be administered by injection, that is, intravenously, intramuscularly, intracutaneously, subcutaneously, intraduodenally, or intraperitoneally. Also, the GRM compositions described herein can be administered by inhalation, for example, intranasally. Additionally, the GRM compositions of the present invention can be administered transdermally. The GRM compositions of this invention can also be administered by intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995). Accordingly, the present invention provides pharmaceutical compositions of a GRM including a pharmaceutically acceptable carrier or excipient and a GRM compound as disclosed herein.

For preparing pharmaceutical compositions from the GRM compound as disclosed herein, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving one or more compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compounds of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Glucocorticoid Receptor Modulator and Cancer Chemotherapeutic Agent Administration The GRM or the cancer chemotherapeutic agent may be administered once, or twice, or more times during a day. The GRM may be administered at a different time than the cancer chemotherapeutic agent is administered; or, in embodiments, and on one or more days, the GRM may be administered on the same day that the cancer chemotherapeutic agent is administered. The GRM may be administered for one day; for two days; for three days; or for more days. The GRM may be administered on a day, or on days, in which a cancer chemotherapeutic agent is also administered to the patient. In embodiments, the GRM is administered on a day, or on days, other than a day in which a cancer chemotherapeutic agent is also administered to the patient. In embodiments, a GRM is administered on a daily basis to a patient, while a cancer chemotherapeutic agent is administered on an intermittent basis, such as, e.g., administration of a cancer chemotherapeutic agent once every week, or administration of a cancer chemotherapeutic agent once every other week, or administration of a cancer chemotherapeutic agent once every three weeks, or administration of a cancer chemotherapeutic agent once every month, for a period of time selected from: one, two, or three weeks, or one, two, three, four, five, or six months.

The GRM compounds, or the cancer chemotherapeutic agents, or both, can be delivered by any suitable means, including oral, parenteral (e.g., intravenous injection or intramuscular injection) and topical methods. The GRM, or the cancer chemotherapeutic agent, or both, can be administered orally. For example, the GRM can be administered as a pill, a capsule, or liquid formulation as described herein. Alternatively, GRMs can be provided via parenteral administration. For example, the GRM, or the cancer chemotherapeutic agent, or both, can be administered intravenously (e.g., by injection or infusion into a vein). the GRM, or the cancer chemotherapeutic agent, or both, can be administered intra-arteriorly (e.g., by injection or infusion into an artery or arteriole). In embodiments, the GRM, or the cancer chemotherapeutic agent, or both, can be administered by injection or infusion into a lymphatic vessel, lymph node, a body cavity, or into the peritoneum, or elsewhere. Transdermal administration methods, by a topical route, can be formulated as applicator sticks, solutions, suspensions, emulsions, gels, creams, ointments, pastes, jellies, paints, powders, and aerosols. Additional methods of administration of the compounds described herein, and pharmaceutical compositions or formulations thereof, are described herein.

The GRM, or the cancer chemotherapeutic agent, or both, may be administered at any time during the day or night. In embodiments of the methods provided herein, a GRM, or cancer chemotherapeutic agent, or both, may be administered in the morning; and may be administered in the morning prior to the morning meal ("fasted" administration) or may be administered in the morning within about 30 minutes or within about one hour after the patient begins eating the morning meal ("fed" administration).

The GRM and the cancer chemotherapeutic agent may be provided in a pharmaceutical preparation, and may be provided in unit dosage form. In such form the preparation is subdivided into unit doses containing appropriate quantities of the compounds and compositions of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In some embodiments, the GRM, or the cancer chemotherapeutic agent, or both, is administered in one dose. In other embodiments, the GRM, or the cancer chemotherapeutic agent, or both, is administered in more than one dose, e.g., 2 doses, 3 doses, 4 doses, 5 doses, 6 doses, 7 doses, or more. In some cases, the doses are of an equivalent amount. In other cases, the doses are of different amounts. The doses can increase or taper over the duration of administration. The amount will vary according to, for example, the GRM properties and patient characteristics.

Any suitable GRM dose, or cancer chemotherapeutic agent dose, may be used in the methods disclosed herein. The administered dose can be at least about 300 milligrams (mg) per day, or about 600 mg/day, e.g., about 600 mg/day, about 700 mg/day, about 800 mg/day, about 900 mg/day, about 1000 mg/day, about 1100 mg/day, about 1200 mg/day, or more. For example, where the GRA is relacorilant, the GRM dose may be, e.g., 10 mg/day, or 25 mg/day, or 50 mg/day, or 75 mg/day, or 100 mg/day, or 150 mg/day, or 200 mg/day, or 250 mg/day, or 300 mg/day, or 400 mg/day, or 500 mg/day, of relacorilant. For example, where the GRA is mifepristone, the GRM dose may be, e.g., 300 mg/day, or 600 mg/day, or 900 mg/day, or 1200 mg/day of mifepristone. In embodiments, the GRM, or the cancer chemotherapeutic agent, or both, is administered orally. In some embodiments, the GRM, or the cancer chemotherapeutic agent, or both, is administered in at least one dose. In other words, the GRM or the cancer chemotherapeutic agent, or both, can be administered in 1, 2, 3, 4, 5, 6, 7, 8, 9, 10 or more doses. In embodiments, the GRM, or the cancer chemotherapeutic agent, or both, is administered orally in 1, 2, 3, 4, 5, 6, 7, 8, 9, 10 or more doses.

The subject may be administered at least one dose of GRM, or cancer chemotherapeutic agent, or both, in one or more doses over, for example, a 2-48 hour period. In some embodiments, the GRM, or the cancer chemotherapeutic agent, or both, is administered as a single dose. In other embodiments, the GRM, or the cancer chemotherapeutic agent, or both, is administered in more than one dose, e.g. 2 doses, 3 doses, 4 doses, 5 doses, or more doses over a 2-48 hour period, e.g., a 2 hour period, a 3 hour period, a 4 hour period, a 5 hour period, a 6 hour period, a 7 hour period, a 8 hour period, a 9 hour period, a 10 hour period, a 11 hour period, a 12 hour period, a 14 hour period, a 16 hour period, a 18 hour period, a 20 hour period, a 22 hour period, a 24 hour period, a 26 hour period, a 28 hour period, a 30 hour period, a 32 hour period, a 34 hour period, a 36 hour period, a 38 hour period, a 40 hour period, a 42 hour period, a 44 hour period, a 46 hour period or a 48 hour period. In some embodiments, the GRM, or the cancer chemotherapeutic agent, or both, is administered over 2-48 hours, 2-36 hours, 2-24 hours, 2-12 hours, 2-8 hours, 8-12 hours, 8-24 hours, 8-36 hours, 8-48 hours, 9-36 hours, 9-24 hours, 9-20 hours, 9-12 hours, 12-48 hours, 12-36 hours, 12-24 hours, 18-48 hours, 18-36 hours, 18-24 hours, 24-36 hours, 24-48 hours, 36-48 hours, or 42-48 hours.

III. Examples

The following examples are offered to illustrate, but not to limit, the claimed invention.

Example 1

In the following, reference is made to RECIST and RECIST 1.1, which refer to the Response Evaluation Criteria for Solid Tumors. These criteria, first promulgated in 2000, and updated in 2009 (as RECIST 1.1), are generally accepted, and nearly universally used criteria for clinical trials of therapies for solid tumors. See, e.g., Schwartz et al., Eur J Cancer. July; 62: 132-137 (2016). The study described in this Example was performed and evaluated according to these criteria. Detection of the ovarian cancer marker CA-125 was also used, per Gynecologic Cancer Intergroup (GCIG) criteria, in evaluating the patient samples.

Patients

Patients with solid tumors were enrolled in study NCT02762981, a phase 1/2 study of CORT125134 (aka relacorilant) in combination with nab-paclitaxel. The patients were all 18 years of age or older, with advanced or metastatic solid tumors who have disease progression; all patients gave informed consent to participate in this study.

Key inclusion criteria included that the patients be 18 years of age or older, with advanced or metastatic solid tumors who have disease progression; the patients must have been treated with up to three prior lines of therapy in the advanced setting (previous treatment with nab-paclitaxel was allowed); the patients must have an ECOG-PS (Eastern Cooperative Oncology Group Performance Status) of 0-1; must have adequate renal, hepatic, and bone marrow function; and must have measurable or evaluable disease.

For patients enrolled in a specific dose-finding pancreatic cohort, the key inclusion criteria also included: histologically confirmed diagnosis of pancreatic adenocarcinoma; CA19-9 (or CEA, CA-125 in non-CA 19-9 elevated tumors) measured within 14 days prior to first dose of study drug; and Metastatic (non-irradiated) lesion that is measurable by RECIST 1.1. (Patients with pancreatic neuroendocrine tumors, lymphoma of the pancreas, or ampullary cancer were not eligible for this specific cohort.)

Key exclusion criteria further included: Requirement for treatment with chronic or frequently used oral corticosteroids for medical conditions or illnesses (eg, rheumatoid arthritis, immunosuppression after organ transplantation).

Figure 2:
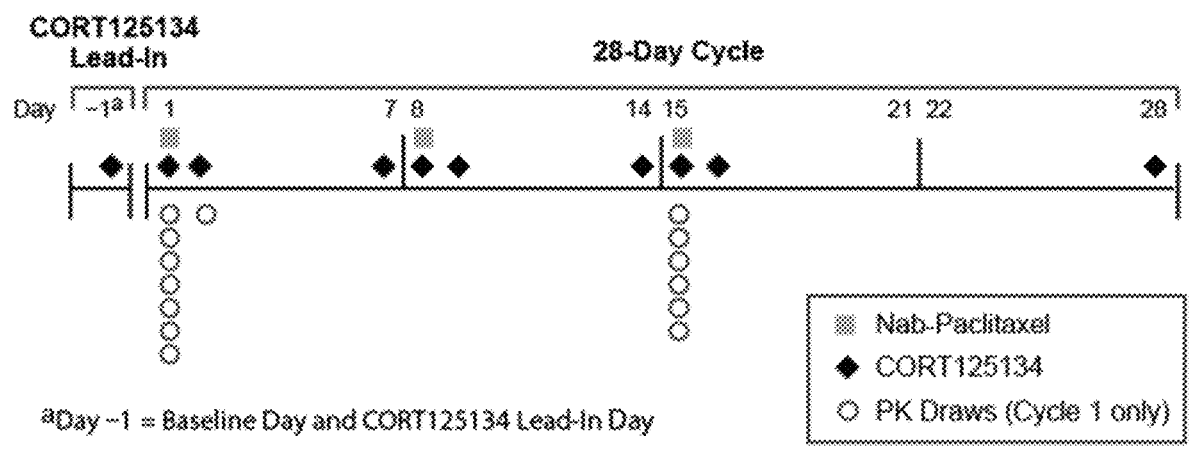
FIG. 2: Segment II Intermittent-Dosing Regimen

Patients received one or more cycles of treatments as describe schematically in FIGS. 1 and 2. The treatment schedules of each 28-day cycle are shown in those figures. Patients in Segment I of the study received continuous dosing of relacorilant ("CORT125134"); that is, relacorilant was administered to the patients on a daily basis. Patients in Segment II of the study received intermittent dosing of relacorilant ("CORT125134"); that is, relacorilant was administered to the patients on those days indicated by the diamond symbols, but not on other days. The first cycle of treatment is termed "cycle 1" (abbreviated as "C1"), the second cycle as "cycle 2" ("C2"), and so forth. The days of each cycle are numbered; thus, day 1 of cycle one is "C1D1" and day 15 of cycle 1 is "C1D15". Thus, the days of relacorilant administration to patients in cycle 1 of Segment II of the study are C1D-1, C1D1, C1D2, C1D7, C1D8, C1D9, C1D14, C1D15, C1D16, and C1D28 (as shown in FIG. 2, where day-1 is the baseline day, during which the patients received the "lead-in" dose of relacorilant). Relacorilant dosing followed the same schedule during subsequent cycles of treatment.

Tumor Assessments

Tumor assessments were performed at screening, end of cycle 2, and every 6-8 weeks thereafter with confirmation of tumor response performed as needed per RECIST (version 1.1). Ovarian, fallopian tube, or primary peritoneal cancer tumors also included CA-125 assessment and response per GCIG criteria. Patients were dosed with relacorilant daily (see FIG. 1) or intermittently (see FIG. 2), and nab-paclitaxel was administered on a 28-day cycle.

FIG. 1 illustrates the dosing schedule for cancer patients receiving both nab-paclitaxel ("Nab-Pac") and relacorilant ("CORT125134"), showing Segment I of the clinical experimentation, in which cancer patients received nab-paclitaxel ("Nab-Pac") and relacorilant pursuant to a Continuous-Dosing Regimen, consisting of two phases, a Dose-Finding phase and Dose-Extension phase. The schematic diagram illustrates the initial phase ("Part 1: Dose Finding") and the subsequent phase ("Part 2: Dose-Extension"). In this study, cancer patients received nab-paclitaxel intermittently, and, once relacorilant was administered following the nab-paclitaxel lead-in period, the cancer patients also received daily relacorilant. The Dose Finding phase began with "Nab-Pac Lead-In", in which patients received nab-paclitaxel on Day 1 (indicated by the square symbol), and had eight blood draws on Day 1, and a single blood draw on Day 2 (indicated by the open circle symbols). Blood obtained from these blood draws was analyzed and stored as detailed in the text below. The "Nab-Pac Lead-In" portion of the regimen was followed by the "CORT125134 Lead-In" phase, which began daily administration of relacorilant (also known as CORT125134). The daily relacorilant administration began on Day 1 of the CORT125134 Lead-In phase (a further blood draw was obtained on that day as well), and continued daily through day 7 of that "lead-in" phase (and further on a daily basis for 28 days after day 7 of the "lead-in"). Relacorilant administration is indicated by the solid diamond symbols. Further blood draws were obtained on Day 7 of the "lead-in" phase as well (indicated by the open circles). Following the 7 days of nab-paclitaxel Lead-In, and following the 7 days of CORT125134 Lead-In that followed that nab-paclitaxel Lead-In, a "28-Day Cycle" of administration of both nab-paclitaxel (on days 1, 8, and 15 of the 28-day cycle, indicated by the square symbols) and relacorilant (daily administration on days 1 through 28, as indicated by the diamond symbols) was performed. The open circles indicate blood draws.

In the second phase shown in FIG. 1 ("Part 2: Dose Extension"), patients received relacorilant on days 1 through 7 of the "CORT125134 Lead-In" of the Dose Extension study. Following this 7 days of daily relacorilant, a further "28-Day Cycle" began, in which the patients received nab-paclitaxel on Day 1, Day 8, and Day 15 of the 28-Day cycle, while continuing to receive daily relacorilant on days 1 through 28 of this 28-Day cycle. Blood was drawn on Day 1, Day 8, and Day 15 as indicated by the open circles.

FIG. 2 illustrates the dosing schedule for cancer patients receiving both nab-paclitaxel ("Nab-Pac") and relacorilant ("CORT125134") according to an Intermittent Dosing Regime, showing Segment II of the clinical study. In this study, cancer patients received relacorilant on Day-1 (which served as the Baseline Day and the relacorilant lead-in day). Following Day-1, a 28-Day cycle began, in which cancer patients received nab-paclitaxel intermittently, and received relacorilant intermittently. The cancer patients received relacorilant on Days 1 and 2, on Days 7-9, on Days 14-16, and on Day 28 (as indicated by the filled diamond symbols). The cancer patients received nab-paclitaxel on Day 1, on Day 8, and on Day 15 (as indicated by the square symbols). Blood was drawn on Day 1, Day 8, and Day 15 as indicated by the open circles.

Specimen Collection

Blood was collected at baseline, prior to administration of relacorilant or nab-paclitaxel. Blood was also drawn in the morning, pre-dose, on cycle 1, day 15. Blood (in the amount of 2.5 milliLiters (mL)) was drawn into a PAXGene blood RNA tube (Qiagen) using a butterfly needle. The tube was sealed and gently inverted 10 times. The tube was frozen in dry ice and stored at −80° C. until RNA extraction.

RNA Isolation and Quantification

Paired baseline and cycle 1, day 15 (C1D15) specimens were thawed and processed in the same batch. RNA was isolated using the PAXgene Blood RNA kit (Qiagen) using the protocol recommended by the manufacturer. RNA yield was quantified using a NanoDrop ND-2000 spectrophotometer (ThermoFisher Scientific). RNA was assessed using a custom 33-gene panel after mRNA sample preparation and hybridization using NanoString nCounter XT Assay, following the operation and maintenance instructions for the NanoString prep station and digital analyzer. Specific RNA transcripts were quantified using a Nanostring nCounter FLEX instrument (NanoString Technologies) and analyzed using nSolver 3.0. (Nanostring Technologies, Seattle Wash., USA).

Data Normalization and Analysis

Housekeeping gene pairwise correlations were determined using nSolver 3.0 (NanoString Technologies). Test genes were normalized to the housekeeping genes HPRT1, PPIB, TRAP1, EEF1A1, and TBP. Change from baseline was calculated using the RNA counts at baseline and cycle 1, day 15 as follows:

Change from Baseline=(C1D15−baseline)/(baseline)

Results

Housekeeping Genes Selection

The glucocorticoid receptor controls the expression of many genes, so it is critical that GR-independent housekeeping genes are selected. Pairwise correlation coefficients were determined using the raw counts of the 9 candidate housekeeping genes ACTA, GAPDH, FPGS, HPRT1, PPIB, TRAP1, RPLPO, EEF1A1, and TBP. The subset including HPRT1, PPIB, TRAP1, EEF1A1, and TBP were selected as true housekeeping genes due to consistent pairwise correlation coefficients greater than 0.87.

Normalized Counts of GR-Responsive Genes

Figure 3:
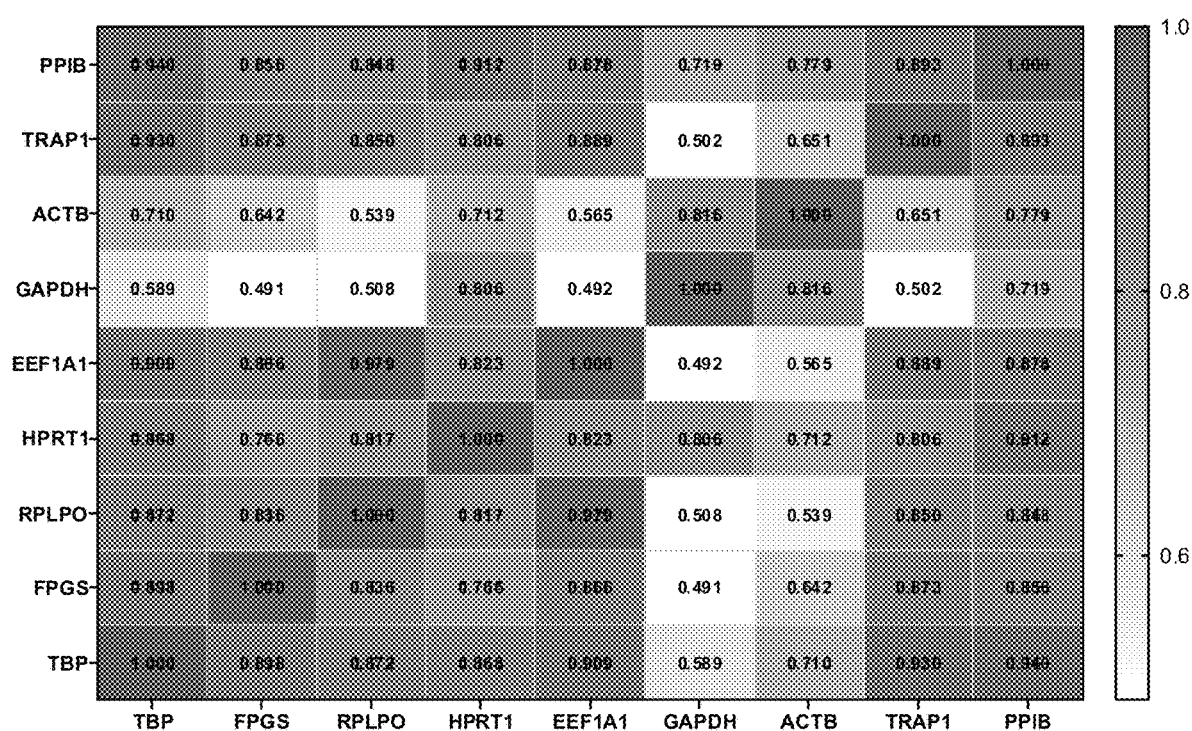
FIG. 3: Pairwise correlations in raw counts between candidate housekeeping genes

Pairwise correlations between candidate housekeeping genes is shown in FIG. 3. The darkness of the hue of each cell in the figure gives an indication of the positive magnitude of the correlation (thus, the darkest hues are found on the diagonal, as each gene expression level shows maximal correlation (1.0) with itself). These correlations were based on raw counts (mRNA expression levels). After normalization to GR-independent housekeeping genes, the remaining 24 genes in the Nanostring panel were analyzed. These genes were pre-selected based on literature and Corcept studies (NCT03335956, data on file at Corcept) suggesting they are induced by synthetic or endogenous corticosteroids. These genes are not expected to be affected by nab-paclitaxel (Maranville et al., 2014). A full list of assessed genes is provided in Table 1.

TABLE 1

Genes Analyzed in This Study

| Common name | Accession | HUGO name | NSID |
| --- | --- | --- | --- |
| ACTB | NM_001101.2 | ACTB | NM_001101.2:1010 |
| B2M | NM_004048.2 | B2M | NM_004048.2:25 |
| cIAP2 | NM_182962.2 | BIRC3 | NM_182962.2:275 |
| DUSP1 | NM_004417.2 | DUSP1 | NM_004417.2:987 |
| EEF1A1 | NM_001402.5 | EEF1A1 | NM_001402.5:790 |
| FKBP4 | NM_002014.3 | FKBP4 | NM_002014.3:310 |
| FKBP5 | NM_001145775.1 | FKBP5 | NM_001145775.1:540 |
| FPGS | NM_001018078.1 | FPGS | NM_001018078.1:633 |
| GAPDH | NM_002046.5 | GAPDH | NM_002046.5:350 |
| GATA-3 | NM_001002295.1 | GATA3 | NM_001002295.1:1691 |
| GSK3b | NM_002093.2 | GSK3B | NM_002093.2:925 |
| HPRT1 | NM_000194.1 | HPRT1 | NM_000194.1:240 |
| HSP-90 | NM_001017963.2 | HSP90AA1 | NM_001017963.2:1655 |
| IL10 | NM_000572.2 | IL10 | NM_000572.2:230 |
| IL6 | NM_000600.3 | IL6 | NM_000600.3:364 |
| MCL-1 | NM_021960.3 | MCL1 | NM_021960.3:1260 |
| NF-kappaB | NM_003998.2 | NFKB1 | NM_003998.2:1675 |
| PEPCK | NM_002591.2 | PCK1 | NM_002591.2:1870 |
| Per1 | NM_002616.2 | PER1 | NM_002616.2:4365 |
| PIK3CG | NM_002649.2 | PIK3CG | NM_002649.2:2125 |
| POMC | NM_000939.2 | POMC | NM_000939.2:1092 |
| PPIB | NM_000942.4 | PPIB | NM_000942.4:272 |
| COX2 | NM_000963.3 | PTGS2 | NM_000963.3:450 |
| PTX-3 | NM_002852.3 | PTX3 | NM_002852.3:1152 |
| RGS-2 | NM_002923.1 | RGS2 | NM_002923.1:855 |
| RPLPO | NM_001002.3 | RPLPO | NM_001002.3:250 |
| SGK1 | NM_005627.2 | SGK1 | NM_005627.2:1790 |
| SOCS-1 | NM_003745.1 | SOCS1 | NM_003745.1:1025 |
| STAT1 | NM_139266.1 | STAT1 | NM_139266.1:455 |
| STAT3 | NM_003150.3 | STAT3 | NM_003150.3:2060 |
| TBP | NM_001172085.1 | TBP | NM_001172085.1:587 |
| TGFB1 | NM_000660.3 | TGFB1 | NM_000660.3:1260 |
| TRAP1 | NM_016292.2 | TRAP1 | NM_016292.2:1293 |

Figure 4:
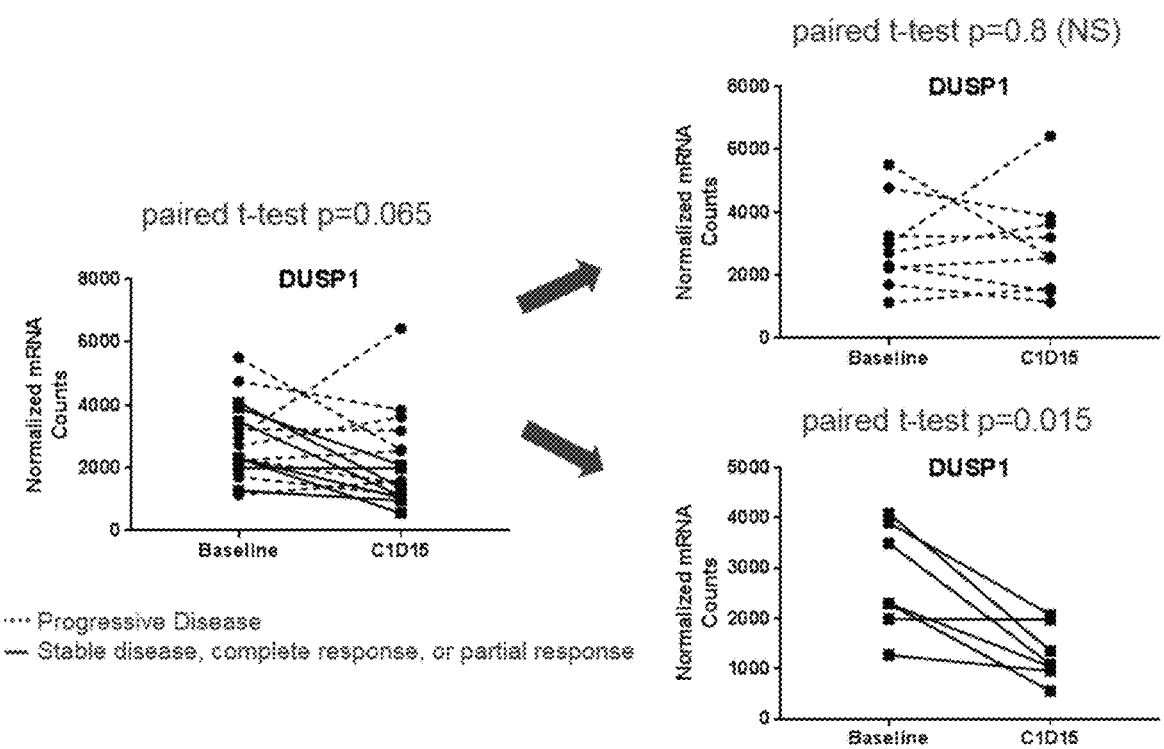
FIG. 4: Normalized DUSP1 mRNA counts at baseline and C1D15 in all patients and patient sub-sets.

To determine the effect of relacorilant on the expression levels of these genes, the counts at cycle 1, day 15 were compared to the counts as baseline. As shown in FIG. 4 for DUSP1 mRNA expression levels, some (nine) patients suffered progressive disease (shown in the graph at upper right of the figure) but several (seven) patients received benefit, experiencing stable, partial, or complete response to the combined nab-paclitaxel and relacorilant treatment.

When all patients were analyzed, the normalized mRNA counts for the gene DUSP1 (FIG. 4) were not significantly different between baseline and cycle 1, day 15 (paired t-test p=0.065). However, within patients experiencing benefit, as defined by stable disease (SD), partial response (PR), or complete response (CR), there was a significant decrease in DUSP1 counts from baseline to cycle 1, day 15 (paired t-test p=0.015). This decrease was not observed in the patients who did not experience a benefit, as defined by progressive disease. Baseline DUSP1 levels, independent of levels at cycle 1, day 15, were not different between patients with progressive disease and patients who benefited from therapy (data not shown). Thus, it appears that decreasing DUSP1 mRNA expression levels after combined nab-paclitaxel and relacorilant treatment are indicative of patient benefit.

Figure 5:
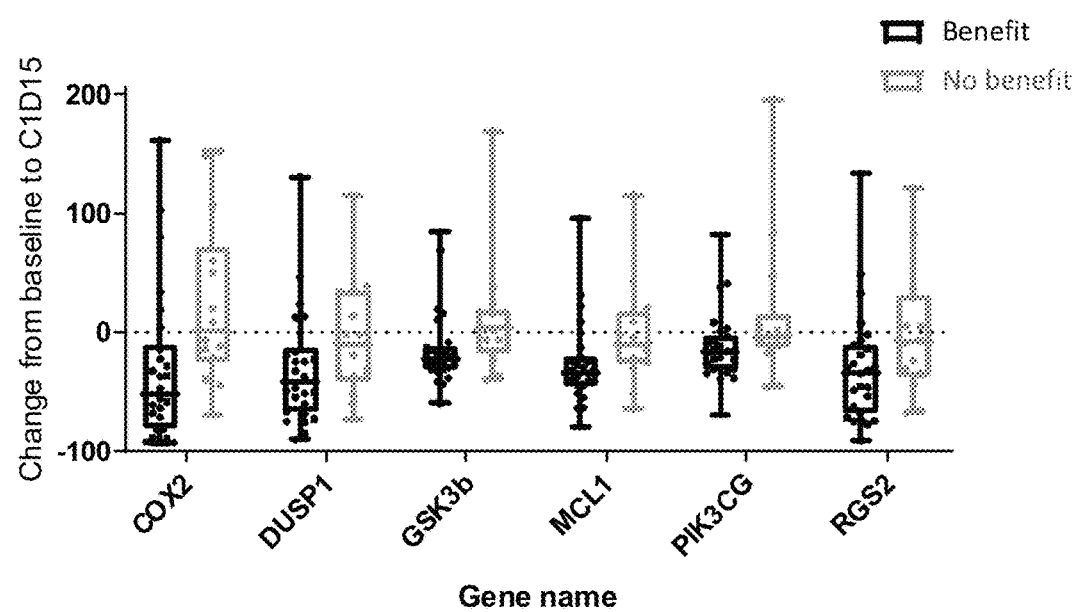
FIG. 5: Genes with a significant change from baseline in patients who benefited from relacorilant+nab-paclitaxel.
Figure 6A:
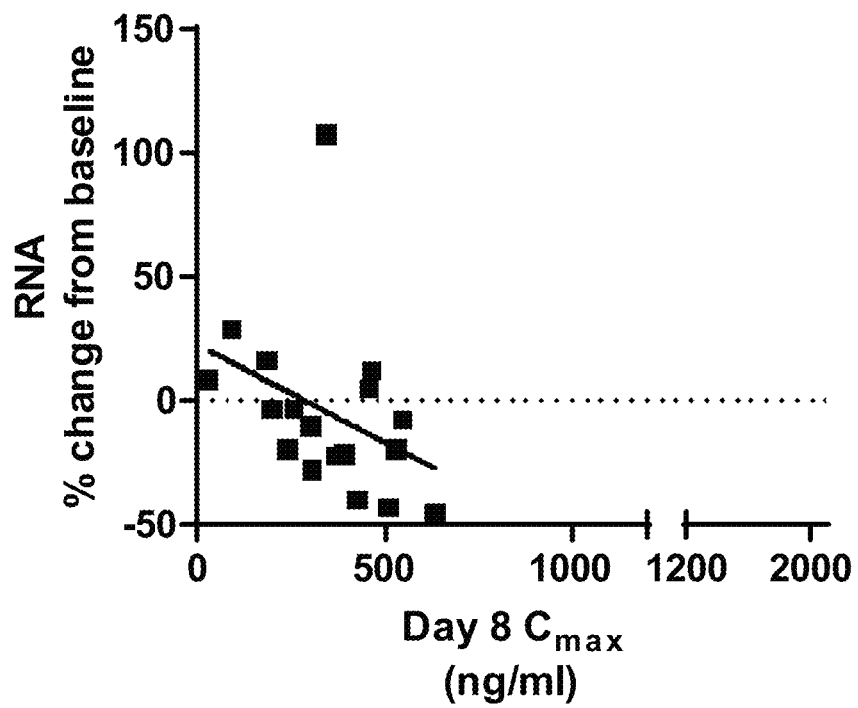
FIG. 6A. Pharmacokinetic:Pharmacodynamic (PK:PD) relationships. The average change from baseline to C1D15 for 10 GR-induced RNAs is plotted as a function of relacorilant $C_{max}$ for continuous relacorilant dosing. Segment I (6A, 6B) is continuous relacorilant dosing while Segment II (6C, 6D) is intermittent.
Figure 6B:
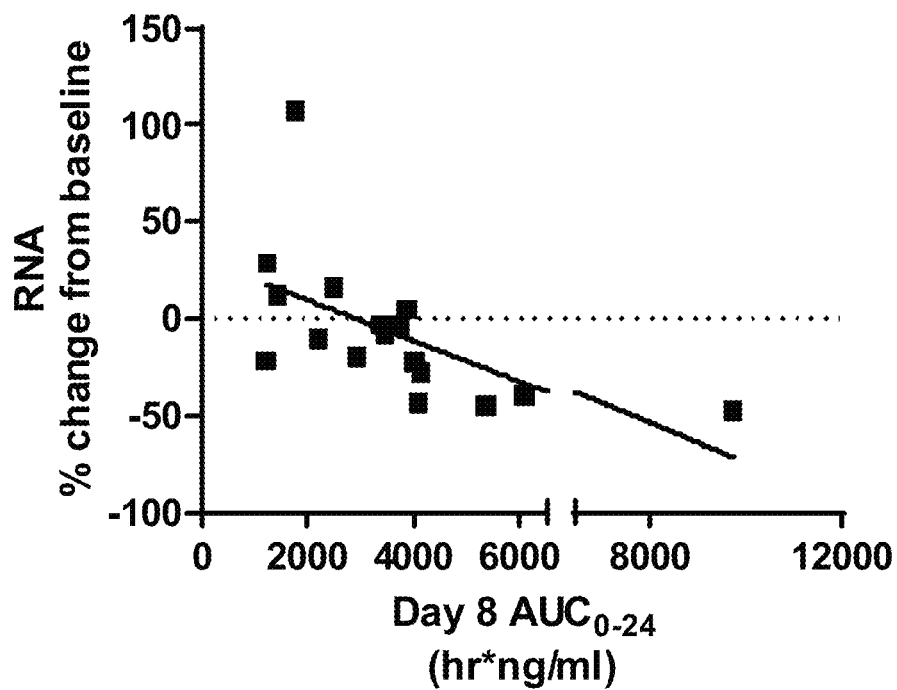
FIG. 6B. Pharmacokinetic:Pharmacodynamic (PK:PD) relationships. The average change from baseline to C1D15 for 10 GR-induced RNAs is plotted as a function of relacorilant $AUC_{0-24}$ for continuous relacorilant dosing.
Figure 6C:
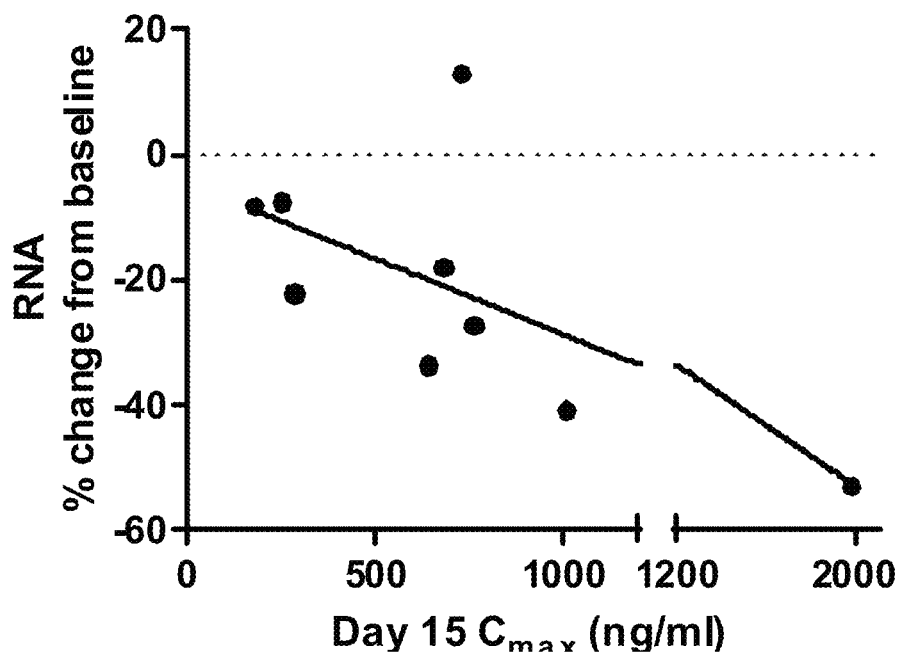
FIG. 6C. Pharmacokinetic:Pharmacodynamic (PK:PD) relationships. The average change from baseline to C1D15 for 10 GR-induced RNAs is plotted as a function of relacorilant $C_{max}$ for intermittent relacorilant dosing.
Figure 6D:
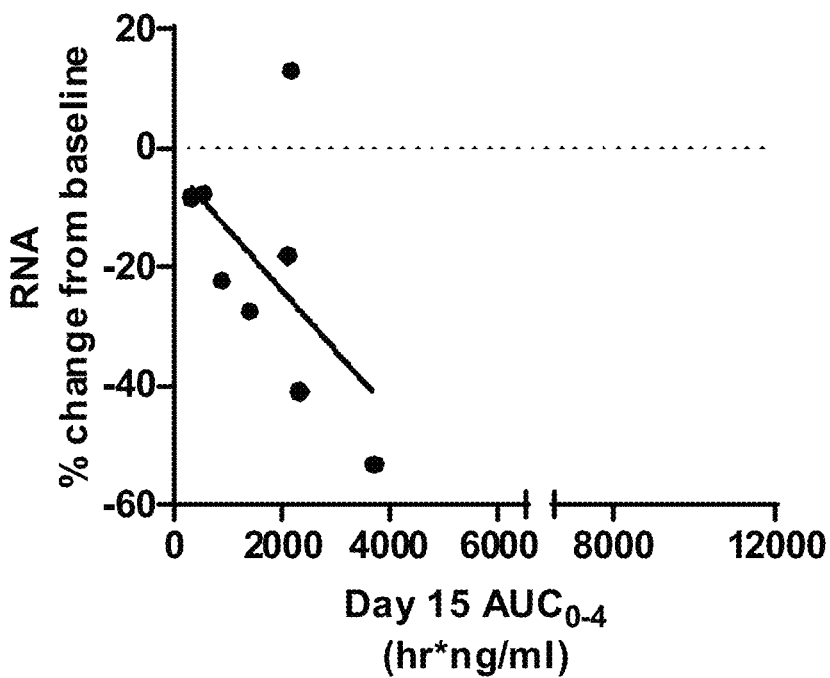
FIG. 6D. Pharmacokinetic:Pharmacodynamic (PK:PD) relationships. The average change from baseline to C1D15 for 10 GR-induced RNAs is plotted as a function of relacorilant $AUC_{0-24}$ for intermittent relacorilant dosing.

Given the observation that DUSP1 levels decrease in the patients who benefited from therapy, change from baseline was calculated for all measured genes and in all matched samples in this study. A subset of genes was identified in which mRNA expression was found to be significantly suppressed in the patients who benefit from therapy as compared to the patients with progressive disease (FIG. 5). No change from baseline (where 1.0 is no change from baseline) in the expression levels of these genes was observed in patients experiencing progressive disease. The p-values shown for each gene are Mann-Whitney p-values that represent the difference in change from baseline between the patients with progressive disease compared to the patients who benefited from therapy.

Relacorilant is known to reduce or block cortisol activation of glucocorticoid receptors (GR); the expression levels of many genes is affected by GR activation; levels of the genes COX2, DUSP1, GSK3b, MCL-1, PIK3CG, RGS-2, SGK1, and STAT3 are affected by GR activation, and were measured in patients receiving relacorilant. Many patients receiving relacorilant had better-than-expected outcomes (stable disease (SD), complete response CR), or partial response (PR)) and so appeared to derive benefit from relacorilant treatment. FIG. 5 compares the expression of several genes in patients who derived benefit from relacorilant treatment, to those patients who did not derive benefit from relacorilant treatment. As shown in FIG. 5, the expression levels of levels COX2, DUSP1, GSK3b, MCL-1, PIK3CG, RGS-2, SGK1, and STAT3 (as measured by mRNA levels) decreased as compared to baseline in those patients who derived benefit from relacorilant+nab-paclitaxel treatment. In contrast, patients whose cancer progressed did not exhibit decreased levels of the genes COX2, DUSP1, GSK3b, MCL-1, PIK3CG, RGS-2, SGK1.

Thus, a decrease in mRNA expression level of other genes, in addition to DUSP1, is indicative of patient benefit, as shown in FIG. 5. Thus, decreases in mRNA expression levels of the following genes are indicative of patients who are likely to benefit from combined treatment with nab-paclitaxel and relacorilant: COX2; DUSP1; GSK3b; MCL-1; PIK3CG; RGS-2; SGK1; and STAT3. Similarly, these results also indicate that patients in whom mRNA expression levels of these genes does not decrease are likely not to benefit from combined treatment with nab-paclitaxel and relacorilant.

Conclusions

Identifying patients likely to respond to a specific therapy improves the efficiency of clinical trials and avoids unnecessary exposure of patients to non-beneficial therapies. This study assessed the effect of relacorilant, a selective glucocorticoid receptor modulator, on the transcription of genes known to be induced by synthetic or endogenous glucocorticoid receptor agonists. Relacorilant suppressed a subset of genes in the patients who benefited from therapy. These same genes were not altered in patients who experience progressive disease. This observation suggests a possible difference in endogenous cortisol activity (sometimes called "cortisol tone" or "functional hypercortisolism") that is enriched in the patients likely to benefit from combined therapy comprising administration of relacorilant and nab-Paclitaxel. Baseline levels of these transcripts did not identify patients likely to benefit. Instead, the change from baseline after relacorilant dosing can be used to identify patients likely to benefit from therapy with relacorilant and nab-Paclitaxel.

Example 2

The previous Example, Example 1, describes a method for identifying cancer patients likely to benefit from therapy including relacorilant, a nonsteroidal selective glucocorticoid receptor (GR) modulator, by measuring gene expression in whole blood of 33 genes. The gene expression pharmacodynamic (PD) data were analyzed against the pharmacokinetic (PK) parameters to establish a PK:PD relationship. A correlation of gene suppression by relacorilant with exposure ($C_{max}$ or AUC) to relacorilant was also observed. Terms and methods used in this Example 2, and not otherwise defined, are the same as those terms and methods used as described in Example 1.

The present example, Example 2, examines a larger set containing 800 genes. Analysis of this larger gene set identified additional genes that may be useful in identifying cancer patients likely to benefit from therapy including relacorilant. Additionally, the genes suppressed by relacorilant were compared to the genes induced by a single dose of 25 mg prednisone. The overlap between the genes induced by prednisone and suppressed in patients who benefited from relacorilant+nab-paclitaxel was significant ($p<1\times10^{-30}$). Such overlap suggests that relacorilant antagonizes the transcription of genes are agonized by prednisone.

These observations strengthen the evidence that the genes identified are indeed affected by relacorilant, are glucocorticoid-receptor controlled genes, and could be useful in identifying patients likely to respond to therapies containing relacorilant. These findings also suggest that the benefit observed in patients treated with relacorilant plus chemotherapy are due to relacorilant and not, solely, chemotherapy.

Calculations

For FIG. 6, the normalized counts of 10 GR-controlled genes were averaged. Change from baseline of these averaged values was calculated per patient using the formula:

Percent change from baseline=((average value at C1D15)−(average value at baseline))/(average value at baseline)*100

Gene set enrichment statistics were calculated using the program available at the URL:
Nemates.org/MA/progs/overlap_stats_prog.html RNA Isolation and Quantification RNA was assessed using a custom 800-gene panel after mRNA sample preparation and hybridization using NanoString nCounter Assay, following the operation and maintenance instructions for the NanoString prep station and digital analyzer. The 800 gene panel was comprised of the Nanostring IO360™ panel plus the following 10 custom probes:

TABLE 2

Further Genes Analyzed in This Study

| Common Name | Accession | HUGO Gene Name | Accession |
|---|---|---|---|
| ESYT1 | NM_015292.2 | ESYT1 | NM_015292.2:1385 |
| FKBP5 | NM_001145775.1 | FKBP5 | NM_001145775.1:540 |
| GSK3B | NM_002093.2 | GSK3B | NM_002093.2:925 |
| IL12A | NM_000882.2 | IL12A | NM_000882.2:775 |
| IPO7 | NM_006391.1 | IPO7 | NM_006391.1:2325 |

TABLE 2-continued

Further Genes Analyzed in This Study

| Common Name | Accession | HUGO Gene Name | Accession |
|---|---|---|---|
| (IMPORTIN 7) | | | |
| MCL1 | NM_021960.3 | MCL1 | NM_021960.3:1260 |
| NR3C1 | NM_001018077.1 | NR3C1 | NM_001018077.1:2822 |
| PER1 | NM_002616.2 | PER1 | NM_002616.2:4365 |
| RGS2 | NM_002923.1 | RGS2 | NM_002923.1:855 |
| GILZ | NM_198057.2 | TSC22D3 | NM_198057.2:1400 |

Data Normalization and Analysis

Housekeeping gene pairwise correlations were determined using advanced analysis in nSolver 3.0 (NanoString Technologies). Test genes were normalized to the housekeeping genes selected by geNORM.

Pharmacokinetic Assessments and Calculations

Relacorilant and nab-paclitaxel levels (concentrations) in plasma were measured using standard methods (e.g., Liquid Chromatography mass spectroscopy/mass spectroscopy (LC-MS/MS)).

Results

Correlation of gene suppression with relacorilant exposure or $C_{max}$

To determine if transcriptional changes observed in whole blood were a function of circulating relacorilant levels, the pharmacodynamic (PD) effects were compared the exposure or $C_{max}$ pharmacokinetic (PK) parameters. The values for 10 related glucocorticoid-controlled genes were averaged for each specimen, and then the change from baseline to cycle 1 day 15 for each average was calculated. For NCT02762981 segment 1 (continuous relacorilant), the PK parameters at cycle 1 day 8 were determined. For NCT02762981 segment 2 (intermittent relacorilant), the PK parameters for cycle 1 day 15 were determined. FIG. 1 shows that the exposure (AUC) and $C_{max}$ for relacorilant are correlated with the average suppression of these 10 genes. A similar analysis conducted with the AUC and Cmax for paclitaxel showed no correlation (data not shown). For this analysis, PK outliers with out-of-range AUC and $C_{max}$ values are not shown.

In FIG. 6, Pharmacokinetic-Pharmacodynamic relationships in NCT02762981 are shown. FIGS. 6A and 6B show the PK:PD relationship in Segment I and FIGS. 6C and 6D show the PK:PD relationship in Segment 2. In FIG. 6A, the average change from baseline to C1D15 for 10 GR-induced RNAs is plotted as a function of relacorilant $C_{max}$ for continuous relacorilant dosing. Segment I (6A, 6B) is continuous relacorilant dosing while Segment II (6C, 6D) is intermittent. (GR-induced means that the expression of the subject RNA is increased in the presence of glucocorticoid, such as the prednisone used in these experiments.) FIG. 6B shows the average change from baseline to C1D15 for 10 GR-induced RNAs is plotted as a function of relacorilant $AUC_{0-24}$ for continuous relacorilant dosing. FIG. 6C shows the average change from baseline to C1D15 for 10 GR-induced RNAs is plotted as a function of relacorilant $C_{max}$ for intermittent relacorilant dosing. FIG. 6D shows the average change from baseline to C1D15 for 10 GR-induced RNAs is plotted as a function of relacorilant $AUC_{0-24}$ for intermittent relacorilant dosing.

Figure 7A:
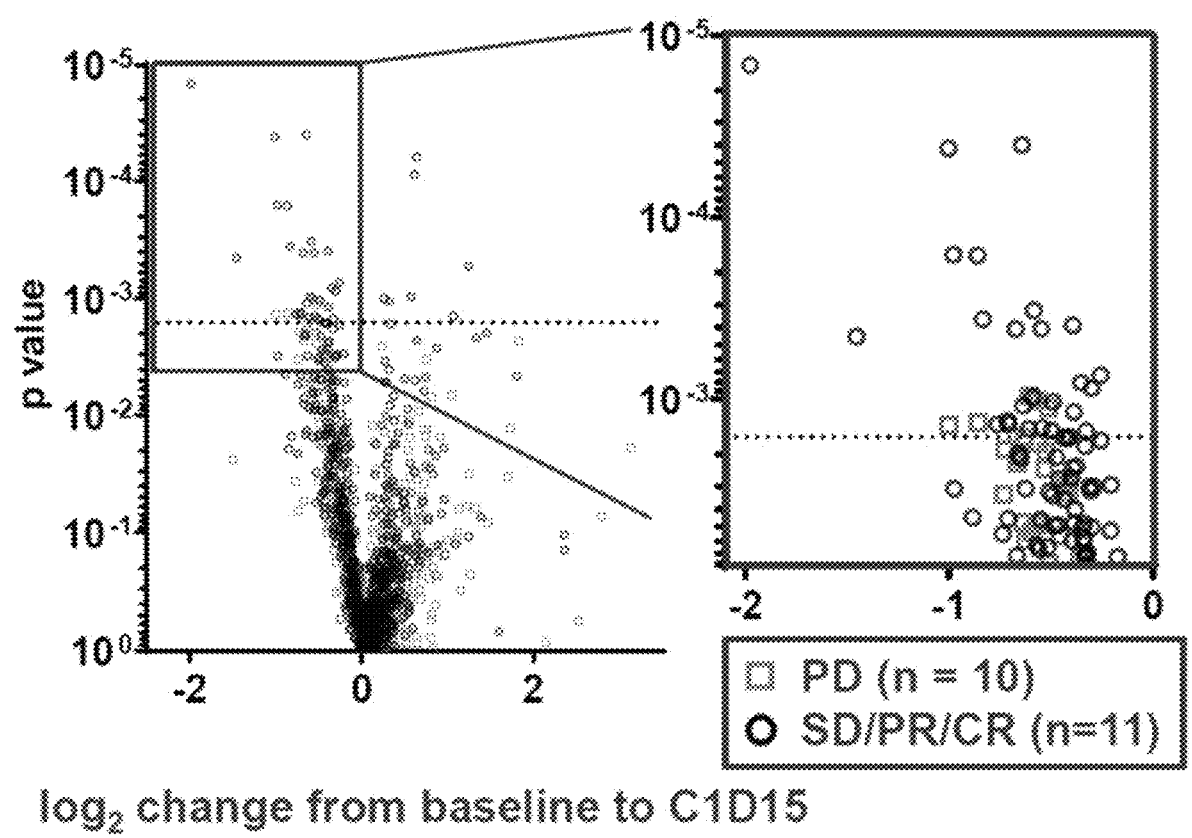
FIG. 7A. Overview of whole blood gene expression fold change.

Identification of Genes Upregulated by Prednisone and Suppressed in Patients Who Benefited from Relacorilant Therapy Previous findings suggested that GR controlled genes modulated by relacorilant plus nab-paclitaxel in patients who benefited (stable disease (SD), partial response (PR), or complete response (CR)). Thus, the patients with progressive disease (PD) were analyzed separately from the patients who benefited from therapy. The study included 21 paired samples from NCT02762981 analyzed at baseline and Cycle 1 Day 15. Of those 21 patients, 10 experienced progressive disease and 11 experienced benefit from therapy. As a comparator, 3 healthy subjects were assessed pre- or 4-hr-post-prednisone alone. A summary of the fold changes and respective p-value is shown in FIG. 7A. Gene expression was measured using mRNA levels.

FIG. 7A provides an overview of whole blood gene expression fold change; the figure shows that transcriptional effects of relacorilant+nab-paclitaxel (Abx) are pronounced in patients with SD, PR, or CR but not PD. (Where SD indicates stable disease, PR indicates partial response, CR indicates complete response, and PD indicates progressive disease.) The transcriptional changes in whole blood from baseline to C1D15 were compared between patients and separated by best overall response. Inset details genes down-regulated in SD/PR/CR (92 genes) versus PD (30 genes) patients. The dotted line represents and adjusted p-value of 0.05. These measurements allow for differentiation between patients in whom relacorilant has a beneficial effect (i.e., SD, PR, or CR, shown with circles) and those whose disease progressed (PD, shown with squares) despite the treatment. Determining whether or not some or all of these genes are downregulated by relacorilant treatment provides a basis for identifying patients likely to benefit from treatments with relacorilant combined with cancer chemotherapy.

Figure 7B:
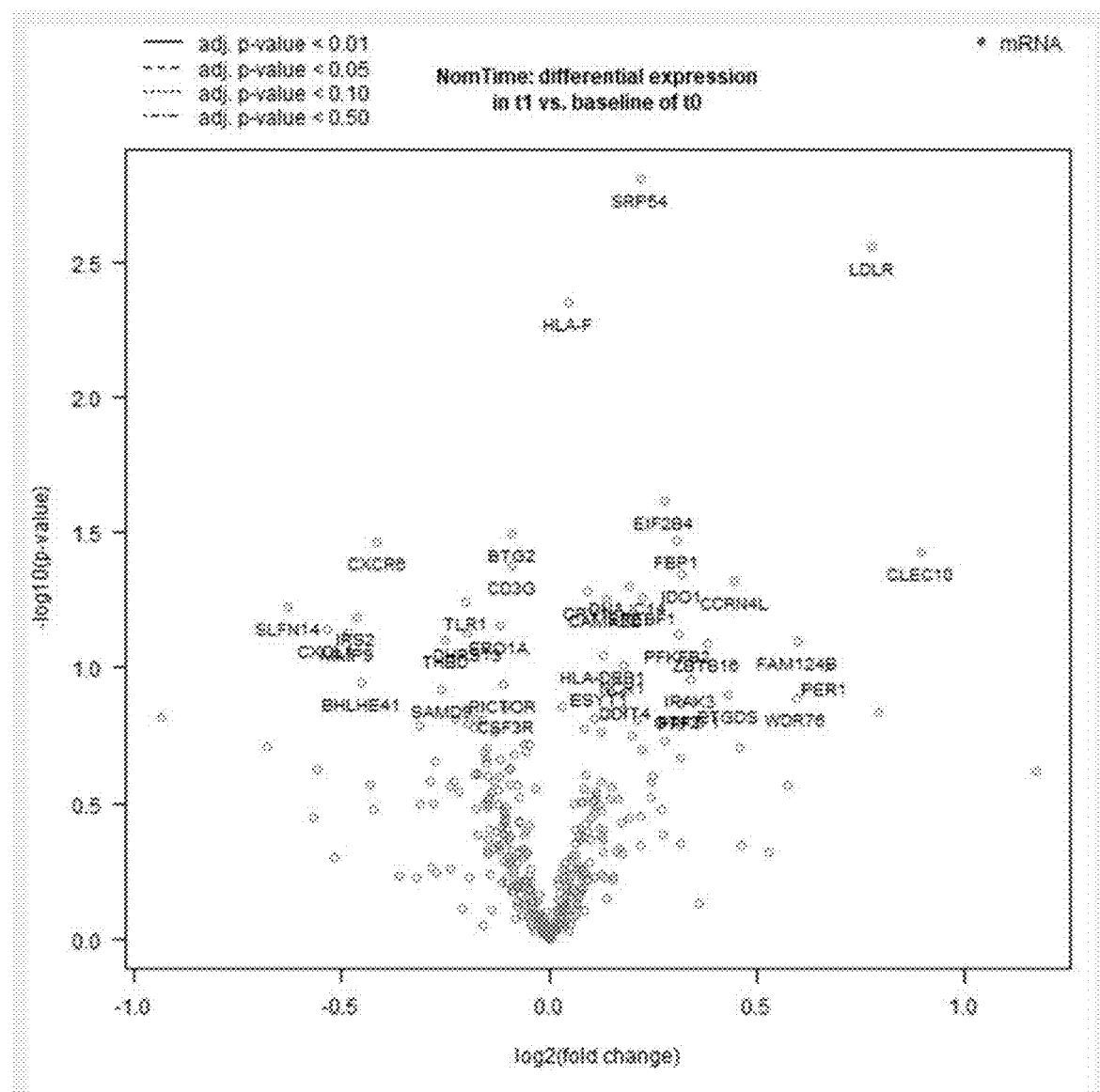
FIG. 7B. Overview of whole blood gene expression fold change due to enzalutamide (an androgen receptor antagonist).

Enzalutamide is an androgen receptor antagonist used in the treatment of hormone-sensitive cancers such as prostate cancer. In contrast to the significant changes in gene expression shown in FIG. 7A, 28 days of enzalutamide treatment administered to human cancer patients did not result in any significant changes (as compared to baseline levels) in gene expression levels in these patients (see FIG. 7B). The small circular markers indicate the change in gene expression for individual genes. None of the gene expression levels changes following enzalutamide (as compared to baseline levels) reach significance (all p-values are greater than 0.5).

Figure 8:
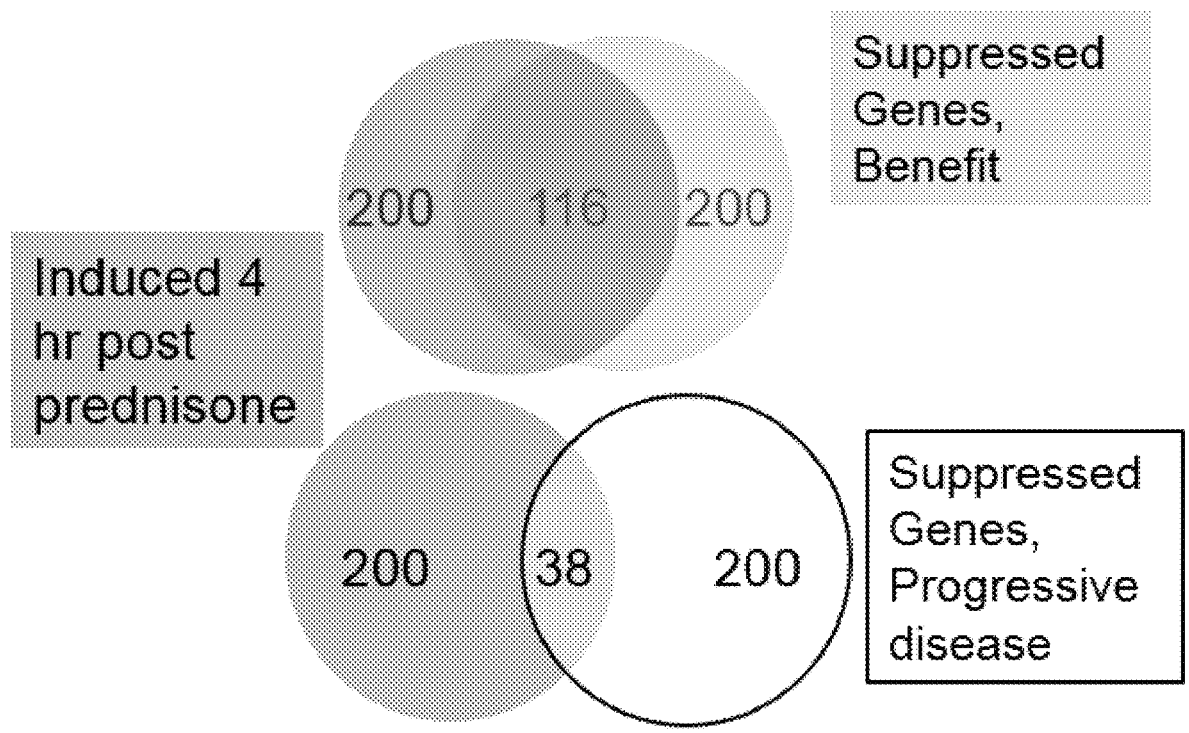
FIG. 8. Comparison of genes induced by prednisone (dark grey, left) to genes suppressed by relacorilant+nab-paclitaxel (right) in patients who benefited (light grey, top) or had progressive disease (white, bottom).

Comparison of Genes Upregulated by Prednisone and Suppressed after Treatment with Relacorilant To determine if the suppressed genes observed in FIG. 7A were controlled by the glucocorticoid receptor (GR), relacorilant+nab-paclitaxel suppressed genes were compared to genes induced by prednisone. The 200 genes with the largest induction post prednisone were compared to the 200 genes with the largest suppression following relacorilant+nab-paclitaxel. Gene enrichment analysis was conducted by determining the number of overlapping genes within each 200 gene set (FIG. 8). There was a significant enrichment of genes shared in the sets induced by prednisone and suppressed by relacorilant in patients who benefited (116 genes, 2.2-fold enrichment, $p=3\times10^{-30}$). The overlap between genes induced by prednisone and suppressed by relacorilant in patients with progressive disease was less than expected if the genes were identified at random (38 genes, 0.7-fold enrichment).

FIG. 8. Comparison of genes induced by prednisone (dark grey, left) to genes suppressed by relacorilant+nab-paclitaxel (right) in patients who benefited (light grey, top) or had progressive disease (white, bottom). Glucocorticoid-induced genes are suppressed by relacorilant+nab-paclitaxel. Transcriptional changes were measured 4 hours post dose with 25 mg prednisone alone in a separate study. Top 200 genes with the largest change from baseline were compared.

A significant overlap in genes induced by prednisone and suppressed in relacorilant+nab-paclitaxel was observed only in the patients with a best overall response of SD, PR, or CR.
Identification of Gene Signature to Identify Patients Who Benefit from Relacorilant+Nab-Paclitaxel In Example, 1, a set of genes that was suppressed only in the patients who benefited from relacorilant+nab-paclitaxel was reported. A similar analysis was conducted from the 800-gene panel reported in FIG. 7. The fold change from baseline to cycle 1 day 15 for 50 genes was calculated. Because the 800 gene panel included both glucocorticoid receptor antagonist induced and suppressed genes, a correction was applied to the induced genes. The predictive value was compared between the top 50 genes from the 800 gene panel and the top 10 genes from the 33 gene panel (FIG. 9A).

For this analysis, the change from baseline for each gene was calculated and the geometric mean across the 10-50 genes was determined per patient.

Figure 9A:
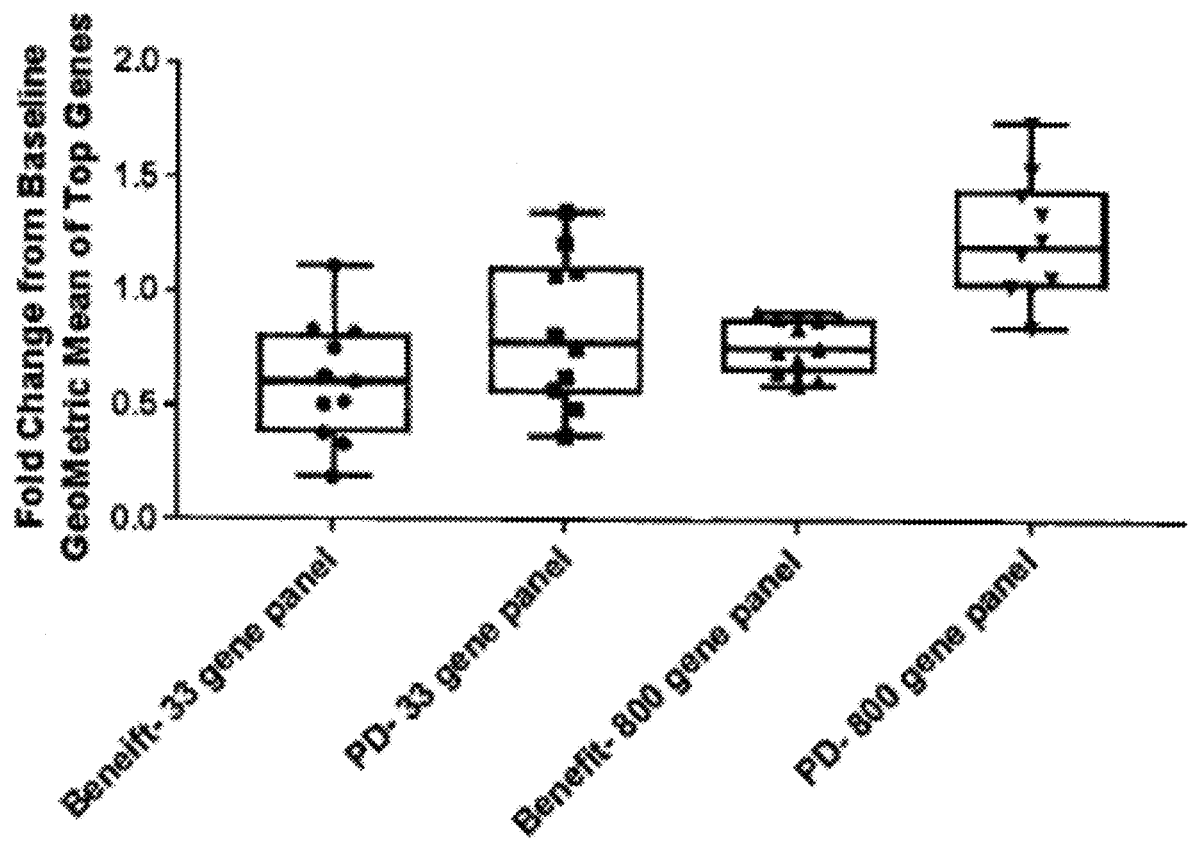
FIG. 9A. Identification of a superior set of genes capable of identifying patients who benefit from relacorilant. The 10 genes identified from the 33 gene panel (left) are compared to the 50 genes identified from the 800 gene panel (right).
Figure 9B:
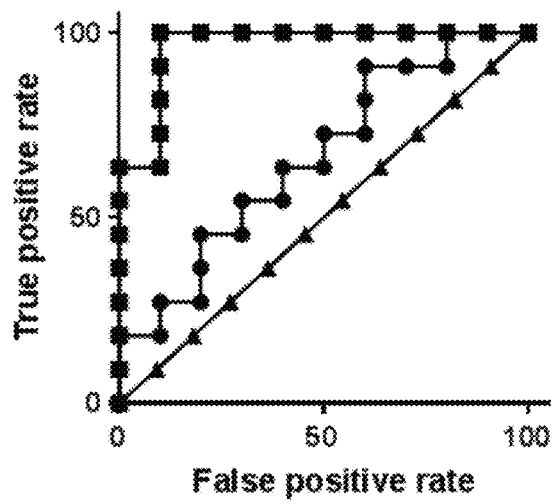
FIG. 9B. A receiver operator curve shows the superior true positive rate and false positive rate of the 8-gene panel derived from the 800 gene set. Squares represent the 50 genes panel derived from the 800 gene set, circles represent the 10 gene panel derived from the earlier 33 gene set, and triangle represent unity. The HUGO gene names for the 50 genes identified from the 800 gene panel are listed in Table 2.

FIGS. 9A and 9B. Identification of a superior set of genes capable of identifying patients who benefit from relacorilant. FIG. 9A shows the 10 genes identified from the 33 gene panel (left) are compared to the 50 genes identified from the 800 gene panel (right). FIG. 9B shows a receiver operator curve demonstrating the superior true positive rate and false positive rate of the 8-gene panel derived from the 800 gene set. Squares represent the 50 genes panel derived from the 800 gene set, circles represent the 10 gene panel derived from the earlier 33 gene set, and triangle represent unity. The HUGO gene names for the 50 genes identified from the 800 gene panel are listed in Table 3.

TABLE 3

50 Genes for which whole blood RNA change post-therapy differed in patients with progressive disease versus patients with benefit

| Common name | Accession | HUGO name | NSID |
|---|---|---|---|
| APC | NM_001127510.2 | APC | NM_001127510.2:462 |
| BID | NM_001196.3 | BID | NM_001196.3:1604 |
| CCL5 | NM_002985.2 | CCL5 | NM_002985.2:277 |
| CCR5 | NM_000579.3 | CCR5 | NM_000579.3:366 |
| CD27 | NM_001242.4 | CD27 | NM_001242.4:326 |
| CD300A | NM_001256841.1 | CD300A | NM_001256841.1:371 |
| CD3E | NM_000733.3 | CD3E | NM_000733.3:233 |
| CD3G | NM_000073.2 | CD3G | NM_000073.2:404 |
| CD40LG | NM_000074.2 | CD40LG | NM_000074.2:1225 |
| CEACAM3 | NM_001277163.2 | CEACAM3 | NM_001277163.2:807 |
| CLEC4E | NM_014358.3 | CLEC4E | NM_014358.3:1392 |
| CLEC7A | NM_197954.2 | CLEC7A | NM_197954.2:55 |
| COL6A3 | NM_004369.3 | COL6A3 | NM_004369.3:3293 |
| COX2 | NM_000963.3 | PTGS2 | NM_000963.3:450 |
| CXCL1 | NM_001511.3 | CXCL1 | NM_001511.3:743 |
| CXCL2 | NM_002089.1 | CXCL2 | NM_002089.1:435 |
| CXCR3 | NM_001142797.1 | CXCR3 | NM_001142797.1:654 |
| CXCR6 | NM_006564.1 | CXCR6 | NM_006564.1:97 |
| EDN1 | NM_001955.2 | EDN1 | NM_001955.2:770 |
| EIF2B4 | NM_001034116.1 | EIF2B4 | NM_001034116.1:1258 |
| ENTPD1 | NM_001098175.1 | ENTPD1 | NM_001098175.1:1418 |
| ESYT1 | NM_015292.2 | ESYT1 | NM_015292.2:1385 |
| F2RL1 | NM_005242.4 | F2RL1 | NM_005242.4:1388 |
| FBP1 | NM_001127628.1 | FBP1 | NM_001127628.1:488 |
| FCGR3A/B | NM_000570.4 | FCGR3B | NM_000570.4:255 |
| FCGRT | NM_004107.4 | FCGRT | NM_004107.4:1260 |
| GIMAP6 | NR_024115.1 | GIMAP6 | NR_024115.1:2175 |
| GOT2 | NM_002080.3 | GOT2 | NM_002080.3:674 |
| GZMK | NM_002104.2 | GZMK | NM_002104.2:634 |
| ICAM2 | NM_000873.3 | ICAM2 | NM_000873.3:415 |
| ICAM3 | NM_002162.3 | ICAM3 | NM_002162.3:1225 |
| IL10RA | NM_001558.2 | IL10RA | NM_001558.2:150 |
| IL32 | NM_004221.4 | IL32 | NM_004221.4:358 |
| IL7R | NM_002185.3 | IL7R | NM_002185.3:1355 |
| ITGA6 | NM_001316306.1 | ITGA6 | NM_001316306.1:1982 |
| KLRB1 | NM_002258.2 | KLRB1 | NM_002258.2:85 |
| LCK | NM_005356.4 | LCK | NM_005356.4:1723 |
| LDHB | NM_001174097.2 | LDHB | NM_001174097.2:1200 |
| MRE11 | NM_001330347.1 | MRE11 | NM_001330347.1:2169 |
| MYC | NM_002467.3 | MYC | NM_002467.3:1615 |
| RELN | NM_005045.3 | RELN | NM_005045.3:988 |
| RICTOR | NM_001285439.1 | RICTOR | NM_001285439.1:117 |
| RPL7A | NM_000972.2 | RPL7A | NM_000972.2:657 |
| SELP | NM_003005.3 | SELP | NM_003005.3:120 |
| THBD | NM_000361.2 | THBD | NM_000361.2:1674 |
| TMEM173 | NM_198282.1 | TMEM173 | NM_198282.1:725 |
| TNFRSF9 | NM_001561.5 | TNFRSF9 | NM_001561.5:567 |
| TNKS | NM_003747.2 | TNKS | NM_003747.2:1948 |
| TP53 | NM_000546.2 | TP53 | NM_000546.2:1330 |
| TREM1 | NM_001242589.2 | TREM1 | NM_001242589.2:101 |

Table 3 above lists the top 50 genes from the 800 gene panel. These 50 genes show a superior ability to distinguish patients who benefit from those with progressive disease as compared to the 10 gene set derived from the original 33 gene panel. The PK:PD relationships described here provide further evidence that the observed gene changes are due to relacorilant and not nab-paclitaxel. The observation that GR-controlled genes are suppressed in patients who benefit provides further evidences that the benefits are due, at least in part, to relacorilant. The superior ability of the top 50 genes from the 800 gene panel to distinguish patients who benefit from those with progressive disease as compared to the 10 gene set derived from the original 33 gene panel confirm and extend the findings of Example 1. Together, these new findings support our previous hypothesis and claims.

Subsets of the 50 genes listed in Table 3 may prove useful in identifying patients likely to respond to treatment. Examples of such subsets include the subsets listed in columns A through E of Table 4. It will be understood that other subsets of the 50 genes listed in Table 3 may be used to identify patients likely to respond to treatment, and may be useful for identifying patients likely to respond to treatment.

TABLE 4

Five Exemplary Subsets of the 50 Genes of Table 3

| Column A | Column B | Column C | Column D | Column E |
|---|---|---|---|---|
| ICAM3 | IL32 | CXCL2 | EIF2B4 | GZMK |
| TREM1 | EDN1 | FBP1 | MRE11 | CD300A |
| FCGRT | CD3G | CD27 | CD3E | TMEM173 |
| GIMAP6 | CCL5 | TNKS | GOT2 | MYC |
| IL10RA | RICTOR | CD40LG | ICAM2 | ENTPD1 |
| IL7R | BID | CXCR3 | TP53 | CXCR6 |
| CEACAM3 | | LDHB | CLEC7A | RELN |
| COL6A3 | | THBD | COX2 | CXCL1 |
| SELP | | TNFRSF9 | | CLEC4E |
| KLRB1 | | RPL7A | | CCR5 |
| FCGR3A/B | | | | ITGA6 |
| LCK | | | | APC |
| ESYT1 | | | | F2RL1 |

Conclusions

Identifying patients likely to respond to a specific therapy improves the efficiency of clinical trials and avoids unnecessary exposure of patients to non-beneficial therapies. This study assessed the effect of relacorilant, a selective glucocorticoid receptor modulator, on the transcription of genes known to be induced by synthetic or endogenous glucocorticoid receptor agonists.

Example 3 Relacorilant Combined with Chemotherapy Agents Reduces Tumor Volume

The present example, Example 3, provides results of administration of the glucocorticoid receptor modulator relacorilant to cancerous cells. These results demonstrate that relacorilant increases tumor cell sensitivity to chemotherapeutic agents both in vitro and in vivo (xenograft studies). As noted above, relacorilant is a glucocorticoid receptor modulator that potently binds the glucocorticoid receptor and does not bind to the androgen receptor or the progesterone receptor ($K_i > 10$ µM; see, e.g., Hunt et al., J Med Chem. 60(8):3405-3421 (2017)). The MIA PaCa-2 xenograft model uses MIA PaCa-2 cell-line cells (pancreatic tumor cells derived from a pancreatic adenocarcinoma from a 65-year-old Caucasian male patient) engrafted into immunodeficient mice. The ovarian OVCAR-5 cell line is derived from a human epithelial carcinoma of the ovary, and was established from ascitic fluid obtained (prior to cytotoxic treatment) from a female patient with progressive ovarian adenocarcinoma.

Figure 10A:
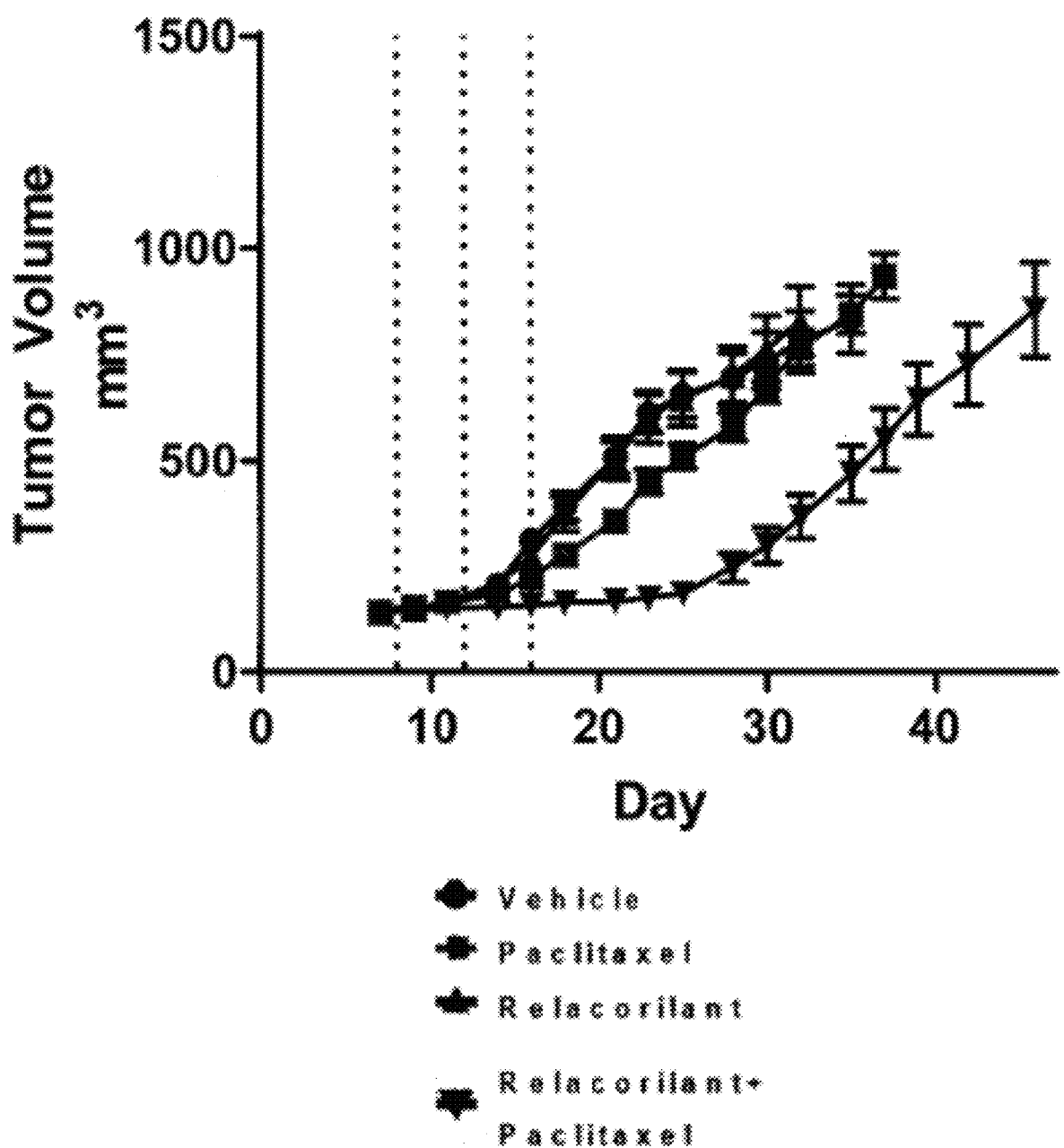
FIG. 10A. Relacorilant sensitizes the MIA PaCa-2 xenograft to paclitaxel. 7.5 mg/kg paclitaxel dosed three times (dashed lines) was ineffective alone. Addition of Relacorilant delayed tumor growth (left, p<0.0001) compared to paclitaxel alone.

FIG. 10A. Relacorilant sensitizes the MIA PaCa-2 xenograft to paclitaxel. Tumor volume of PaCa-2 xenograft tumors implanted in immunodeficient mice is shown as a function of time (days) after implantation in the presence of vehicle (filled circles), paclitaxel (7.5 mg/kg; filled squares), relacorilant alone (upwardly pointing triangles), and relacorilant+7.5 mg/kg paclitaxel (downwardly pointing triangles). 7.5 mg/kg paclitaxel was administered three times (at the days indicated by the dashed vertical lines, indicating days 8, 12, and 16 following tumor implantation into the mice). These doses of paclitaxel were ineffective in delaying tumor growth of the pancreatic tumor cells engrafted in the immunodeficient mice. Addition of relacorilant delayed tumor growth ($p < 0.0001$) compared to paclitaxel alone. Thus, relacorilant restored sensitivity to paclitaxel in the pancreatic MIA PaCa-2 xenograft model.

Figure 10B:
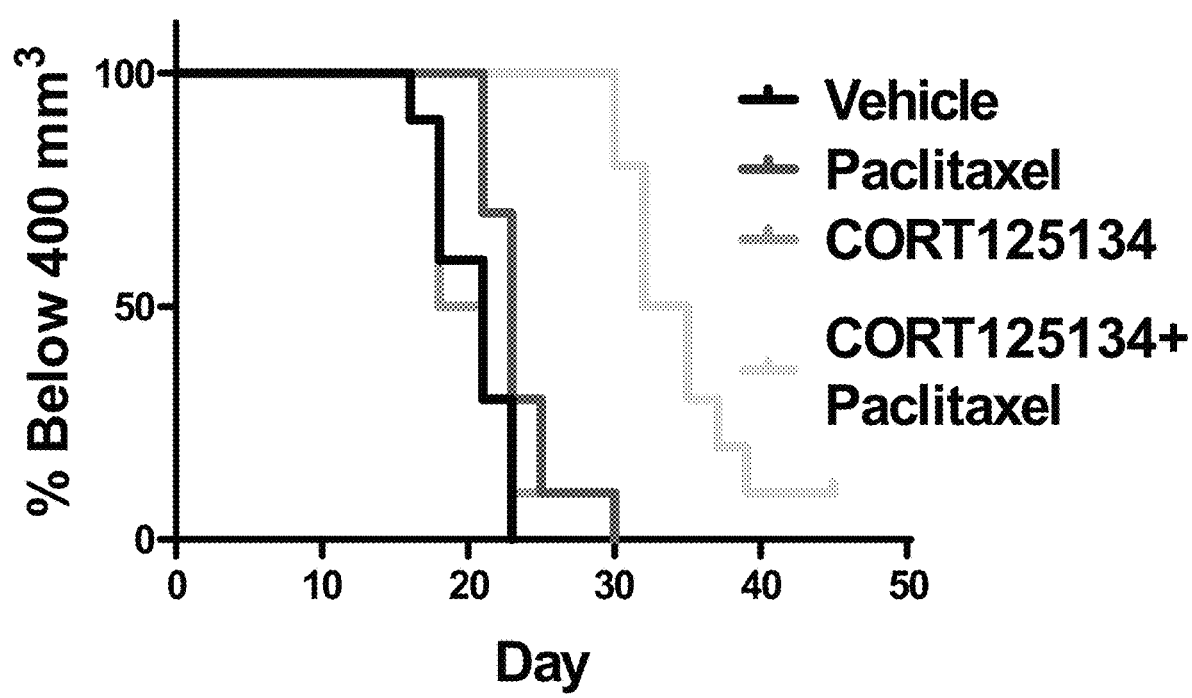
FIG. 10B. Relacorilant with Paclitaxel Reduces MIA PaCa-2 xenograft Tumor Volume.

FIG. 10B. Relacorilant with Paclitaxel Reduces MIA PaCa-2 xenograft Tumor Volume. Initial tumor volume of PaCa-2 xenograft tumors implanted in immunodeficient mice was less than 400 cubic millimeters ($mm^3$). FIG. 10B shows the fraction of xenograft tumors (as %) whose volume remained below 400 $mm^3$ on the days indicated along the horizontal axis. Tumor size progression is thus indicated by lines descending from the top (100%) value. The tumor-bearing mice were treated with vehicle, relacorilant (30 mg/kg every day), paclitaxel (three doses of 7.5 mg/kg paclitaxel, one dose administered on each of the days indicated in FIG. 10A), and the combination relacorilant (30 mg/kg every day) with paclitaxel (7.5 mg/kg doses of paclitaxel each administered on days 8, 12, and 16 post implantation). The two left-most lines indicate tumor sizes over time in mice administered vehicle (DMSO, the darkest line) and in mice administered 300 nM relacorilant alone (lighter gray line, nearly superimposed on the vehicle line). Administration of 7.5 mg/kg paclitaxel dosed three times (on days 8, 12, and 16 after tumor implantation) was ineffective alone in delaying tumor growth of the pancreatic tumor cells engrafted in the immunodeficient mice (dark gray line between the other lines). Addition of 300 nM relacorilant to the paclitaxel doses delayed the time to progression ($p < 0.0001$) compared to paclitaxel alone (right-most light gray line). Xenograft tumor growth was slowed by combined relacorilant+paclitaxel as compared to either paclitaxel alone or relacorilant alone. Relacorilant thus enhanced sensitivity to paclitaxel in the pancreatic MIA PaCa-2 xenograft model.

Figure 11A:
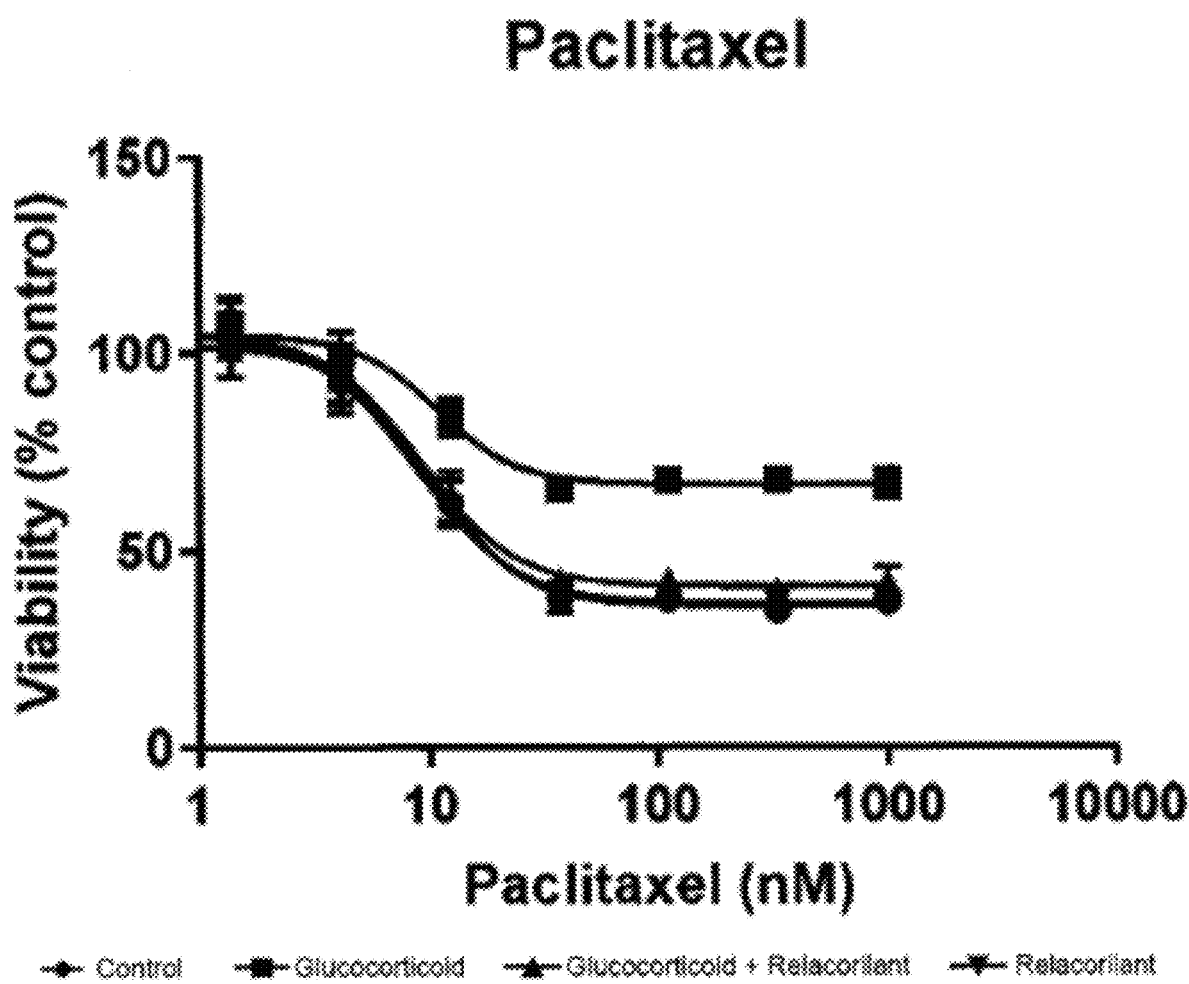
FIG. 11A. Relacorilant restores chemotherapy sensitivity in vitro. Glucocorticoid reduced the maximum effect of paclitaxel in the ovarian OVCAR-5 cell line. Relacorilant restored sensitivity to this agent in the presence of glucocorticoid.

FIG. 11A. Relacorilant restores chemotherapy sensitivity in vitro. Glucocorticoid (100 nM dexamethasone) reduced the maximum effect of paclitaxel in the ovarian OVCAR-5 cell line. Relacorilant restored sensitivity to paclitaxel in the presence of the glucocorticoid.

Figure 11B:
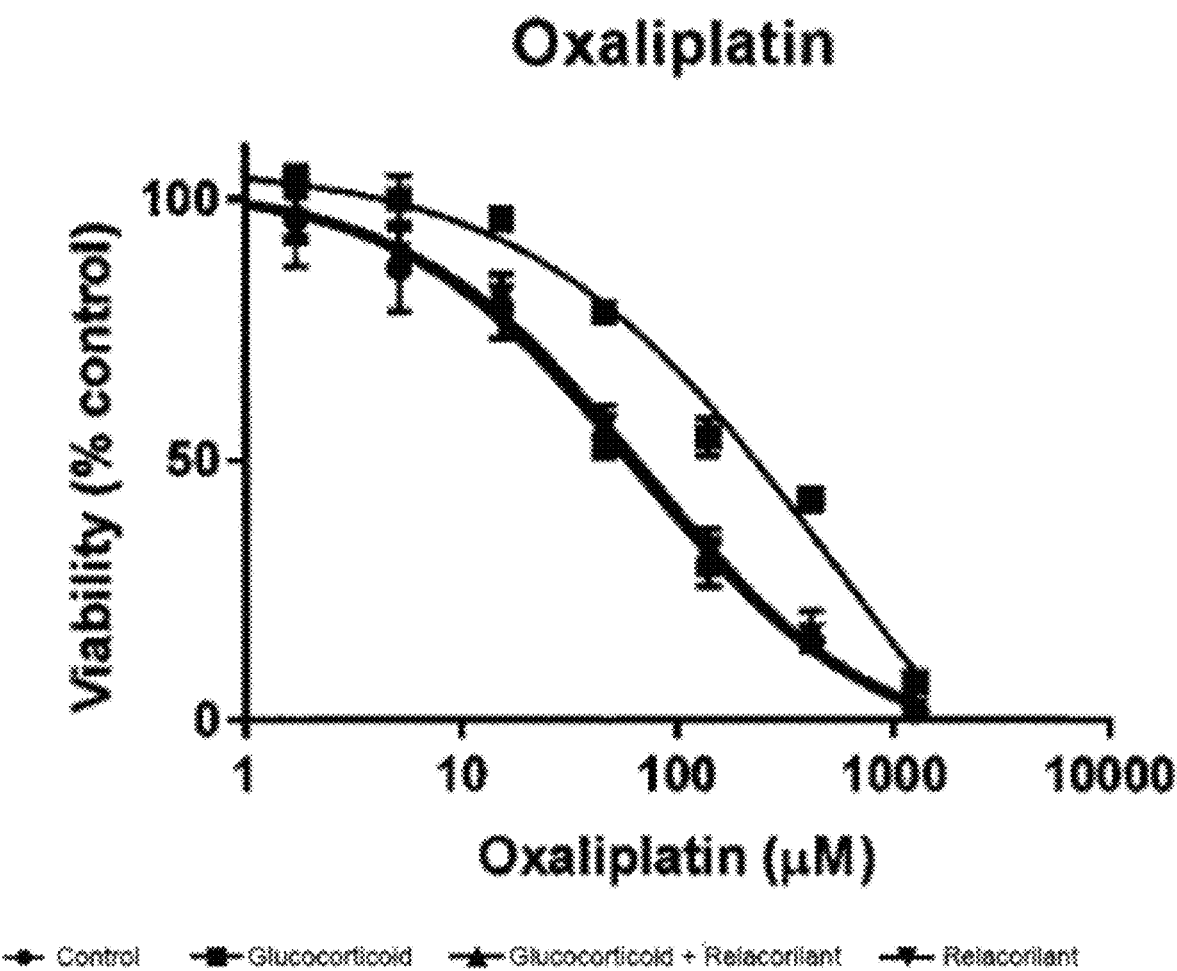
FIG. 11B. Relacorilant restores chemotherapy sensitivity in vitro. Glucocorticoid (100 nM dexamethasone) reduced the half-maximal potency of oxaliplatin in the ovarian OVCAR-5 cell line. Relacorilant restored sensitivity to this agent in the presence of glucocorticoid.

FIG. 11B. Relacorilant restores chemotherapy sensitivity in vitro. Glucocorticoid (100 nM dexamethasone) reduced the half-maximal potency of oxaliplatin in the ovarian OVCAR-5 cell line. Relacorilant restored sensitivity to oxaliplatin in the presence of the glucocorticoid.

Figure 11C:
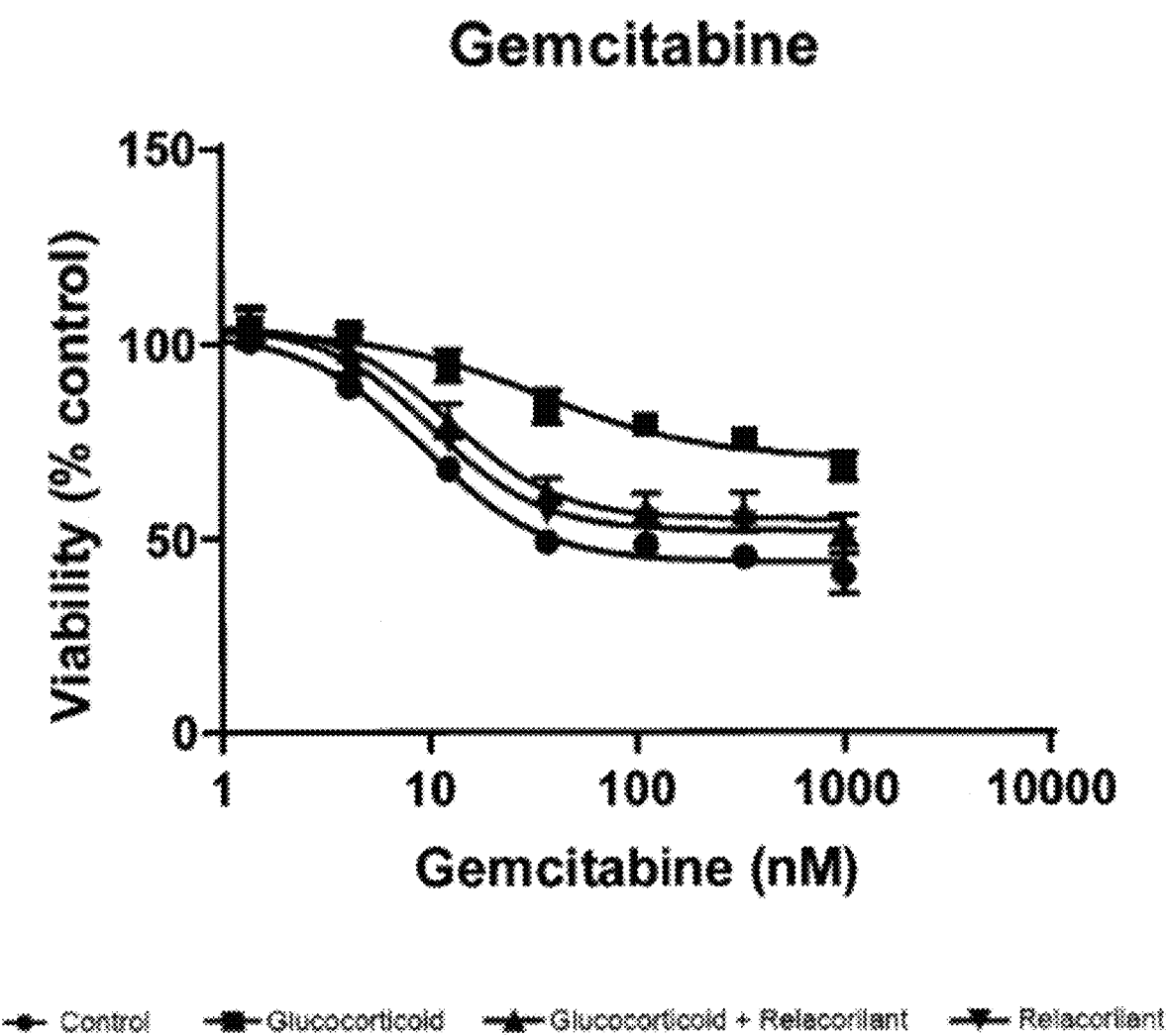
FIG. 11C. Relacorilant restores chemotherapy sensitivity in vitro. Glucocorticoid reduced the maximum effect of gemcitabine in the ovarian OVCAR-5 cell line. Relacorilant restored sensitivity to this agent in the presence of glucocorticoid.

FIG. 11C. Relacorilant restores chemotherapy sensitivity in vitro. Glucocorticoid (100 nM dexamethasone) reduced the maximum effect of gemcitabine in the ovarian OVCAR-5 cell line. Relacorilant restored sensitivity to gemcitabine in the presence of the glucocorticoid.

Figure 12:
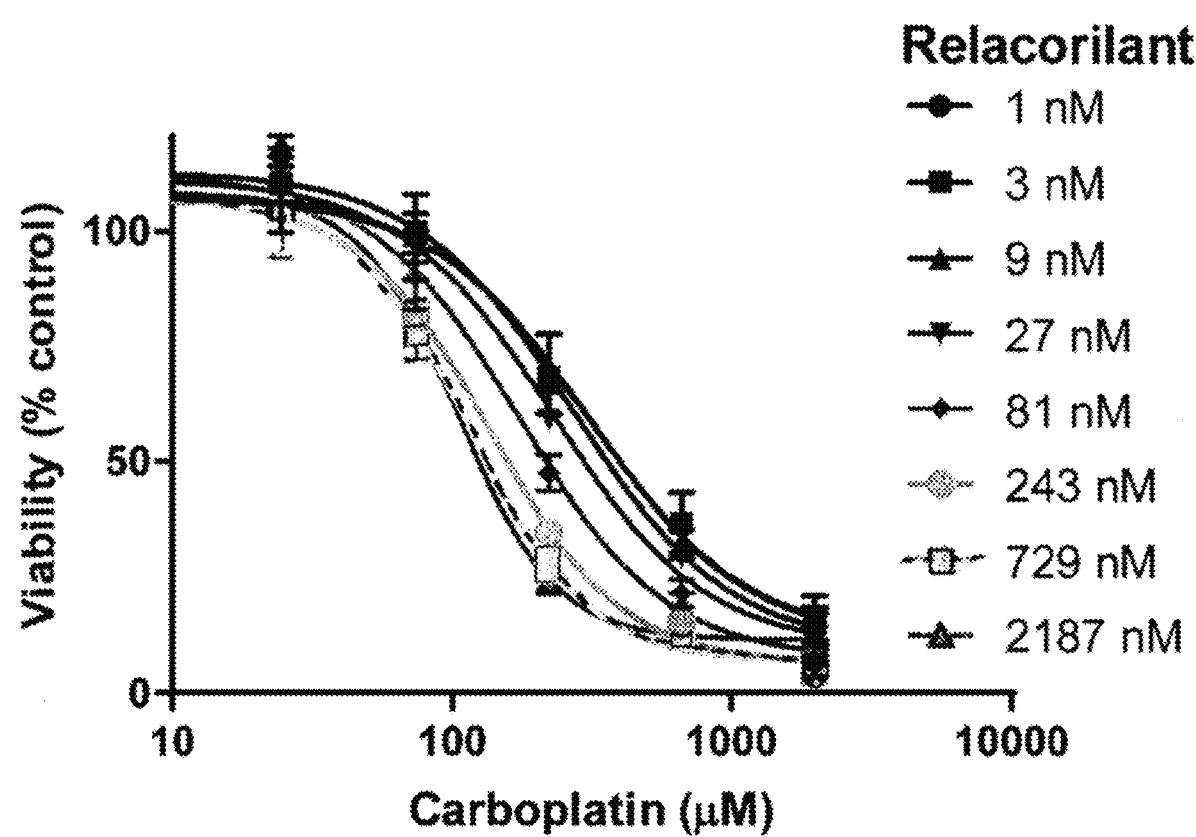
FIG. 12. Potency of carboplatin is dose-dependently increased by Relacorilant in vitro. OVCAR-5 ovarian cells were grown in the presence of glucocorticoid. Carboplatin was titrated against increasing amounts of Relacorilant.

FIG. 12. Potency of carboplatin is dose-dependently increased by relacorilant in vitro. OVCAR-5 ovarian cells were grown in the presence of glucocorticoid (100 nM dexamethasone). Carboplatin was titrated against increasing amounts of relacorilant. The carboplatin effect was dose dependent, with cell viability decreasing as the concentration of carboplatin increased from 1 nM carboplatin to 2187 nM carboplatin.

Example 4 Relacorilant Combined with Chemotherapy Agents Reduces Tumor Volume

The effects of several cancer chemotherapy agents, with and without relacorilant and/or dexamethasone, on cell proliferation in vitro were studied. In the present example, human-derived cancer cell line OVCAR-5 were subjected to treatment with several cancer chemotherapy agents and also relacorilant alone, dexamethasone alone, and the combination of relacorilant and dexamethasone. Dexamethasone increased OVCAR-5 proliferation in the presence of many of the cancer chemotherapy agents; relacorilant was able to inhibit such increased cell proliferation for several cancer chemotherapy agents.

The effects of various chemotherapeutic agents on cell growth of OVCAR-5 human ovarian cancer cells in vitro were studied in the presence and absence of dexamethasone and relacorilant. The amounts of the various chemotherapeutic agents required to inhibit growth of the OVCAR5 human ovarian cancer cell line by fifty percent (IC50) was determined in the presence of dexamethasone, relacorilant, and the combination of dexamethasone and relacorilant. In these experiments, the concentrations of dexamethasone and relacorilant were as follows: 100 nanomolar (nM) dexamethasone; 300 nM relacorilant.

The tumor cells were seeded (4,000 cells plated/well) in a volume of 200 µL/well of FBS-medium (2.5% fetal bovine serum diluted in cell culture medium) in a white polystyrene 96-well microculture plate with or without a fixed dose of dexamethasone or relacorilant. The initial cell density was chosen to be low enough to allow for several population doublings (typically 3 to 5) during the indicated incubation period. The cells were incubated in a humidified incubator at 37° C. with 5% CO2 and 95% air. After 48 hours of incubation, serially diluted test agents in growth medium were added to each well. After 72 hours of culture, the plated cells and Cell Titer-Glo® (Promega G7571) reagents were brought to room temperature to equilibrate for 30 minutes. 200 µL of Cell Titer-Glo® reagent was then added to each well, the plate was shaken for two minutes, and then left to equilibrate for ten minutes. The Cell Titer-Glo® cell viability assay uses ATP levels to determine cell numbers. After this equilibration, luminescence was read on the Biotech Synergy II microplate reader. The percent control (% C) of cell growth for each test concentration was calculated relative to untreated wells. All tests were performed in quadruplicate. Individual assay plates were evaluated for appropriate signal and well-to-well variance in the control wells for quality control.

Figure 13:
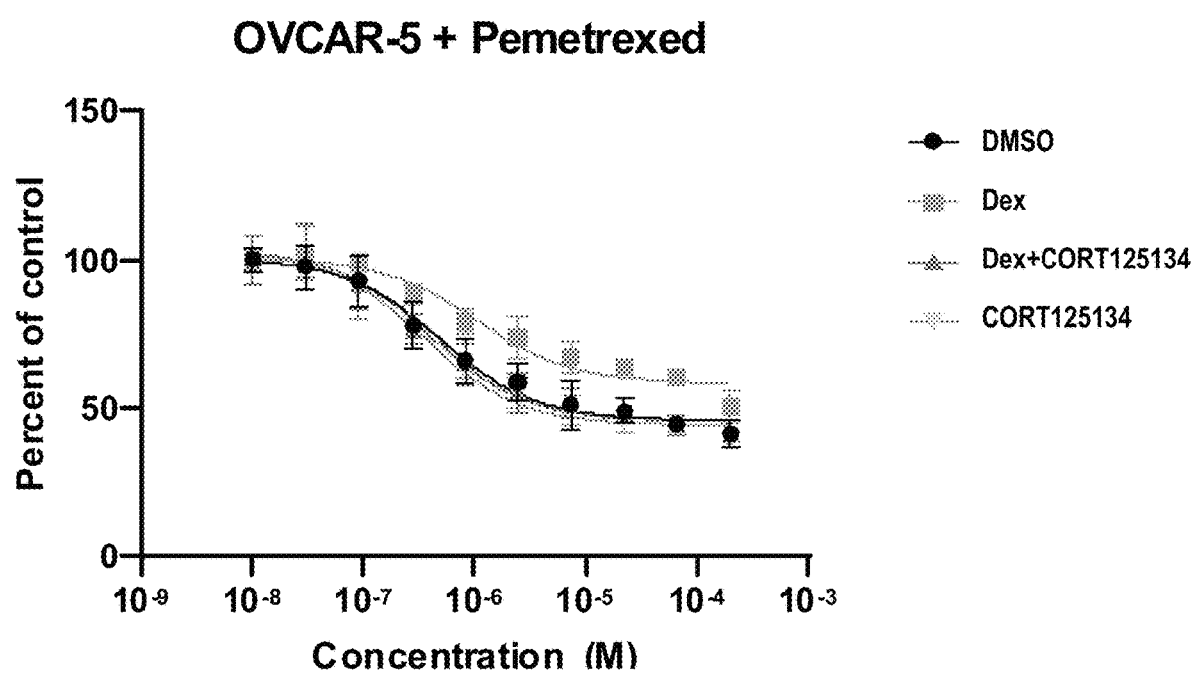
FIG. 13. Relacorilant overcomes the effect of dexamethasone on OVCAR-5 cell survival in the presence of pemetrexed in vitro. Vertical axis shows cell survival as percent of original cell numbers; horizontal axis shows the several concentrations of pemextred to which the OVCAR-5 cells were exposed. Dexamethasone (100 nM) increased cell proliferation (squares) as compared to dimethyl sulfoxide (DMSO) vehicle alone (filled circles). Relacorilant (300 nM) overcame the effect of dexamethasone; OVCAR-5 cell proliferation in the presence of 300 nM relacorilant was similar to that of vehicle (downwardly pointing triangles).
Figure 14:
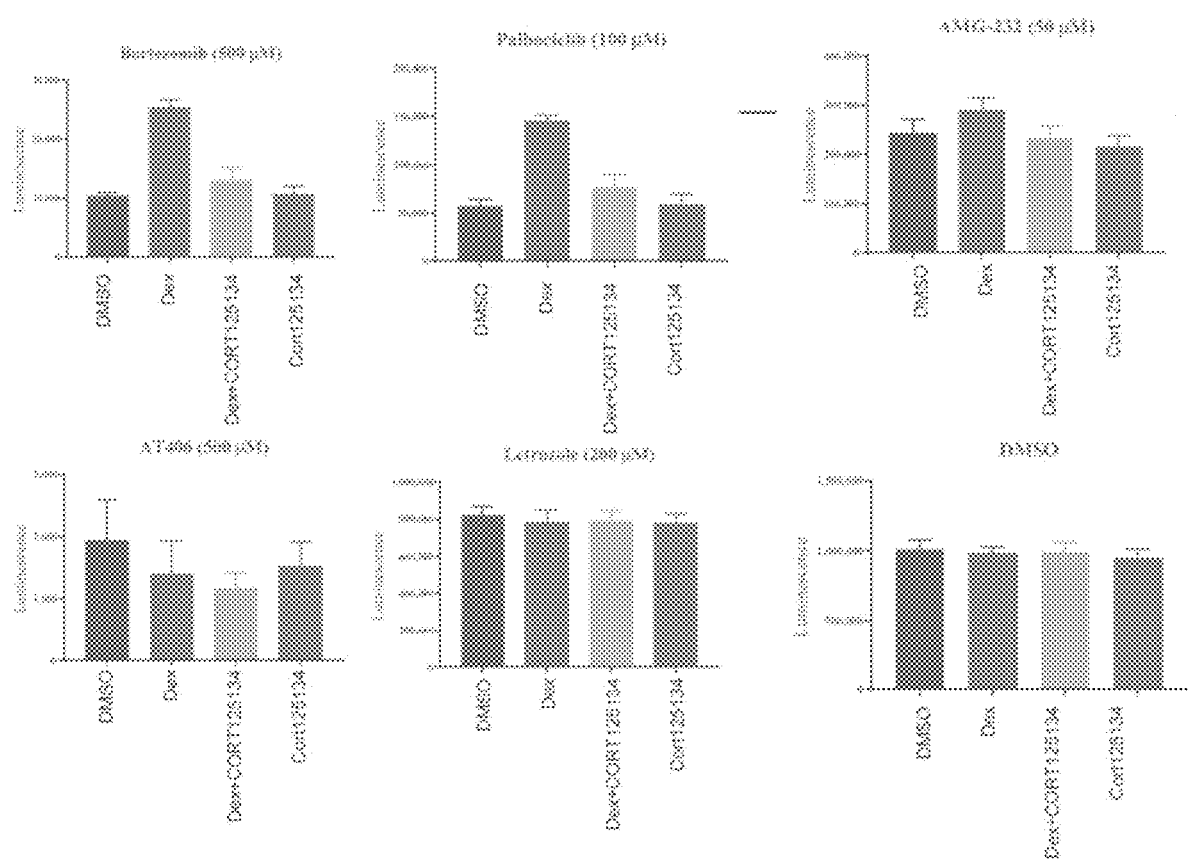
FIG. 14. Relacorilant effects on dexamethasone effects on OVCAR-5 cell growth. This figure shows the effects of relacorilant on OVCAR-5 cell growth in vitro. The vertical scale shows luminosity, which serves as a measure of cell number. The cell numbers in the presence of the indicated concentrations of cancer chemotherapy agents and in vehicle (DMSO), 100 nM dexamethasone (Dex), the combination of 100 nM dexamethasone and 300 nM relacorilant (Dex+CORT125134), and 300 nM relacorilant (CORT125134) are shown. Dexamethasone increased cell numbers in the presence of bortezumib and palbociclib (as compared to vehicle); this increase was opposed by relacorilant.

The results of such tests are reported in FIGS. 13 and 14 and in Table 4.

FIG. 13. Relacorilant overcomes the effect of dexamethasone on OVCAR-5 cell survival in the presence of pemetrexed in vitro. Cell proliferation in the presence of the various concentrations of pemetrexed was increased by 100 nM dexamethasone (squares) as compared to dimethyl sulfoxide (DMSO) vehicle alone (filled circles). OVCAR-5 cell proliferation in the presence of 300 nM relacorilant was similar to that of vehicle (downwardly pointing triangles). Relacorilant antagonized the effect of dexamethasone: cell numbers were similar to those of vehicle for relacorilant administered together with dexamethasone alone (upwardly pointing triangles). The vertical axis shows cell numbers as percent of control (zero or lowest concentration of pemetrexed). The horizontal axis shows pemetrexed concentration.

FIG. 14. Relacorilant effects on dexamethasone effects on OVCAR-5 cell growth. The effects of relacorilant on OVCAR-5 cell growth in vitro are shown in FIG. 14. The vertical scale shows luminosity, which serves as a measure of cell number. The cell numbers in the presence of the indicated concentrations of cancer chemotherapy agents and in vehicle (DMSO), 100 nM dexamethasone (Dex), the combination of 100 nM dexamethasone and 300 nM relacorilant (Dex+CORT125134), and 300 nM relacorilant (CORT125134) are shown for the chemotherapy agents bortezumib (500 µM); palbociclib (100 µM); AMG-232 (50 µM); AT506 (500 µM); letrozole (200 µM); and vehicle (DMSO). In the presence of bortezumib and palbociclib, dexamethasone increased cell numbers as compared to those in vehicle; this increase was opposed by relacorilant.

Several chemotherapeutic agents were tested on OVCAR-5 cells in vitro, providing an indication of these cells' differing responses to dexamethasone and to relacorilant in the presence of different chemotherapeutic agents. Relacorilant reversed the effects of dexamethasone in all cases. The effects of relacorilant on the half-maximal inhibition concentration ($IC_{50}$) of several cancer chemotherapy agents, and the effects of relacorilant on the maximal amount of cell growth inhibition by these agents are provided in Table 5. A rightward shift on graphs such as in FIG. 13 indicates an increase in $IC_{50}$. A leftward shift on the graphs such as in FIG. 13 indicates a decrease in $IC_{50}$. These results are summarized in Table 5 in the column labeled "IC50". In the column labeled "IC50" the symbol "++" indicates that there was a greater than 60% decrease in $IC_{50}$ from the dexamethasone-alone to the relacorilant+dexamethasone treatments; the symbol "+" indicates that there was an about 10% to about 59% decrease in $IC_{50}$ from the dexamethasone-alone to the relacorilant+dexamethasone treatments; and the symbol "−" indicates that there was no decrease, or only an equivocal increase, in $IC_{50}$ from the dexamethasone-alone to the relacorilant+dexamethasone treatments.

In the presence of high chemotherapy concentrations, dexamethasone decreased the maximal toxicity (thus increasing cell viability in the presence of high chemotherapeutic concentrations) and relacorilant reversed this (FIG. 13). The "effect" that is the subject of the column "Max effect" in Table 5 is the increase in maximal cell toxicity caused by addition of relacorilant to the cancer chemotherapeutic agent in the presence of dexamethasone (relacorilant+dexamethasone), as compared to the cancer chemotherapeutic agent plus dexamethasone in the absence of relacorilant ("dexamethasone-alone"). In the column labeled "Max effect" the symbol "++" indicates that there was a consistent increase of 40% or greater in toxicity at high doses of chemotherapeutic from the dexamethasone-alone to the relacorilant+dexamethasone treatments; the symbol "+" indicates that there was a consistent increase in toxicity of about 0% to about 40% at high doses of chemotherapeutic from the dexamethasone-alone to the relacorilant+dexamethasone treatments; and the symbol "−" indicates that there was no increase, or only an inconsistent increase, in toxicity at high doses of chemotherapeutic from the dexamethasone-alone to the relacorilant+dexamethasone treatments.

TABLE 5

| Agent | IC50 | Max effect |
| --- | --- | --- |
| Eribulin | ++ | ++ |
| Vinorelbine | + | ++ |
| Plinabulin | − | ++ |
| Venetoclax | + | − |
| Lapatinib | + | − |
| Doxorubicin | + | + |
| Etoposide | + | − |
| Pemetrexed | ++ | + |
| cisplatin | + | + |
| Erlotinib | − | + |
| Pazopanib | NA | + |
| Tamoxifen | − | − |
| 5-FU | + | − |
| Irinotecan | + | − |
| CHIR-99021 (GSK3) | − | − |
| GSK650394 (SGK) | − | − |
| Olaparib | − | − |
| Chloroquine | − | + |
| Trametinib | − | − |

IC50:

++ >60% decrease in $IC_{50}$ from the dexamethasone-alone to the relacorilant + dexamethasone treatments;

+ ~10-59% decrease in $IC_{50}$ from the dexamethasone-alone to the relacorilant + dexamethasone treatments;

− no decrease or equivocal decrease in IC50 from the dexamethasone-alone to the relacorilant + dexamethasone treatments.

Max effect:

++ consistent >40% increase in toxicity at high doses of chemotherapeutic from the dexamethasone-alone to the relacorilant + dexamethasone treatments;

+ consistent ~0-40% increase in toxicity at high doses of chemotherapeutic from the dexamethasone-alone to the relacorilant + dexamethasone treatments;

− no increase or inconsistent increase in toxicity high doses of chemotherapeutic from the dexamethasone-alone to the relacorilant + dexamethasone treatments.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

We claim:

1. A method of treating cancer in a cancer patient identified as likely to benefit from treatment with both a glucocorticoid receptor modulator (GRM) and a cancer chemotherapy agent, the method comprising:

A) Identifying a cancer patient likely to benefit from combined GRM and cancer chemotherapy treatment by a method comprising determining a decrease in expression level of a gene following treatment with a GRM, said identifying comprising:

Measuring a first expression level of at least one gene in a sample obtained from said patient;

Administering an effective amount of the GRM relacorilant, (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone (also termed "CORT125134"), which has the following structure:

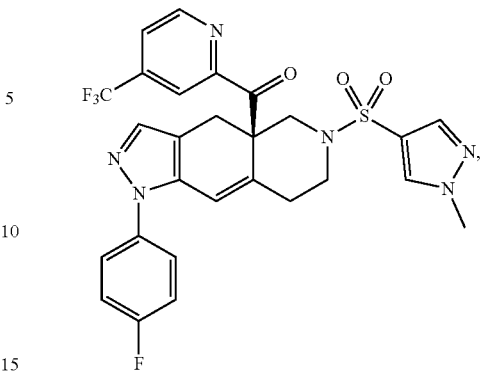

to said patient; then

Measuring a second expression level of said at least one gene in a sample obtained from said patient;

Comparing said first expression level with said second expression level; and

Identifying the cancer patient as being likely to benefit from combined relacorilant and cancer chemotherapy treatment if said first expression level is greater than said second expression level; and B) Administering both a said relacorilant and a cancer chemotherapy agent to the cancer patient identified as being likely to benefit from combined relacorilant and cancer chemotherapy treatment, Whereby said cancer is treated in the cancer patient identified as likely to benefit from treatment with both relacorilant and a cancer chemotherapy agent.

2. The method of claim 1, wherein said expression levels of said at least one gene are measured in a blood sample obtained from the patient.

3. The method of claim 1, wherein said expression levels of said at least one gene are mRNA levels.

4. The method of claim 1, wherein said at least one gene is selected from the group of genes consisting of APC, CLEC4E, ENTPD1, ICAM3, RELN, BID, CLEC7A, ESYT1, IL10RA, RICTOR, CCL5, COL6A3, F2RL1, IL32, RPL7A, CCR5, COX2, FBP1, IL7R, SELP, CD27, CXCL1, FCGR3A/B, ITGA6, THBD, CD300A, CXCL2, FCGRT, KLRB1, TMEM173, CD3E, CXCR3, GIMAP6, LCK, TNFRSF9, CD3G, CXCR6, GOT2, LDHB, TNKS, CD40LG, EDN1, GZMK, MRE11, TP53, CEACAM3, EIF2B4, ICAM2, MYC, and TREM1.

5. The method of claim 1, wherein said at least one gene is selected from the group of genes consisting of ICAM3, TREM1, FCGRT, GIMAP6, IL10RA, IL7R, CEACAM3, and COL6A3.

6. The method of claim 1, wherein said at least one gene is selected from the group of genes consisting of IL32, EDN1, CD3G, CCL5, RICTOR, and BID.

7. The method of claim 1, wherein said at least one gene is selected from the group of genes consisting of CXCL2, FBP1, CD27, TNKS, CD40LG, CXCR3, LDHB, THBD, TNFRSF9, and RPL7A.

8. The method of claim 1, wherein said at least one gene is selected from the group of genes consisting of EIF2B4, MRE11, CD3E, GOT2, ICAM2, TP53, CLEC7A, and COX2.

9. The method of claim 1, wherein said at least one gene is selected from the group of genes consisting of GZMK, CD300A, TMEM173, MYC, ENTPD1, CXCR6, RELN, CXCL1, CLEC4E, CCR5, ITGA6, APC, and F2RL1.

10. The method of claim 4, wherein the expression levels of at least two of said genes are measured, and wherein said relacorilant and said cancer chemotherapy agent are administered to the patient if the first expression levels of the two genes are greater than the second expression levels of the two genes.

11. The method of claim 5, wherein the expression levels of at least two of said genes are measured, and wherein said relacorilant and said cancer chemotherapy agent are administered to the patient if the first expression levels of the two genes are greater than the second expression levels of the two genes.

12. The method of claim 6, wherein the expression levels of at least two of said genes are measured, and wherein said relacorilant and said cancer chemotherapy agent are administered to the patient if the first expression levels of the two genes are greater than the second expression levels of the two genes.

13. The method of claim 7, wherein the expression levels of at least two of said genes are measured, and wherein said relacorilant and said cancer chemotherapy agent are administered to the patient if the first expression levels of the two genes are greater than the second expression levels of the two genes.

14. The method of claim 8, wherein the expression levels of at least two of said genes are measured, and wherein said relacorilant and said cancer chemotherapy agent are administered to the patient if the first expression levels of the two genes are greater than the second expression levels of the two genes.

15. The method of claim 9, wherein the expression levels of at least two of said genes are measured, and wherein said relacorilant and said cancer chemotherapy agent are administered to the patient if the first expression levels of the two genes are greater than the second expression levels of the two genes.

16. The method of claim 1, wherein the expression levels of at least three genes are measured, and wherein said relacorilant and said cancer chemotherapy agent are administered to the patient if the first expression level of said at least three genes is greater than the first expression level of said at least three genes.

17. The method of claim 16, wherein said at least three genes are selected from within the genes listed in one of the following groups of genes:
 a) the group of genes consisting of ICAM3, TREM1, FCGRT, GIMAP6, IL10RA, IL7R, CEACAM3, and COL6A3;
 b) the group of genes consisting of IL32, EDN1, CD3G, CCL5, RICTOR, and BID;
 c) the group of genes consisting of CXCL2, FBP1, CD27, TNKS, CD40LG, CXCR3, LDHB, THBD, TNFRSF9, and RPL7A;
 d) the group of genes consisting of EIF2B4, MRE11, CD3E, GOT2, ICAM2, TP53, CLEC7A, and COX2; and
 e) the group of genes consisting of GZMK, CD300A, TMEM173, MYC, ENTPD1, CXCR6, RELN, CXCL1, CLEC4E, CCR5, ITGA6, APC, and F2RL1.

18. The method of claim 1, wherein said cancer chemotherapy agent comprises a taxane.

19. The method of claim 17, wherein said cancer chemotherapy agent comprises a taxane selected from paclitaxel, nab-paclitaxel, docetaxel, larotaxel, tesetaxel, cabazitaxel, and ortataxel.

* * * * *